United States Patent
Feng et al.

(10) Patent No.: US 11,767,296 B2
(45) Date of Patent: Sep. 26, 2023

(54) HETEROARYL COMPOUNDS AS KINASE INHIBITOR

(71) Applicant: FUJIAN HAIXI PHARMACEUTICALS CO., LTD, Fujian (CN)

(72) Inventors: Yan Feng, Fujian (CN); Ruyong Wang, Fujian (CN); Junqing Li, Fujian (CN); Jianjia Zheng, Fujian (CN); Xin Lian, Fujian (CN); Xuan Gong, Fujian (CN); Yueli Fu, Fujian (CN); Xinshan Kang, Fujian (CN)

(73) Assignee: FUJIAN HAIXI PHARMACEUTICALS CO., LTD, Fujian (CN)

( * ) Notice: Subject to any disclaimer, the term of this patent is extended or adjusted under 35 U.S.C. 154(b) by 431 days.

(21) Appl. No.: 16/979,195

(22) PCT Filed: Mar. 13, 2019

(86) PCT No.: PCT/CN2019/078006
§ 371 (c)(1),
(2) Date: Sep. 9, 2020

(87) PCT Pub. No.: WO2019/174601
PCT Pub. Date: Sep. 19, 2019

(65) Prior Publication Data
US 2022/0380312 A1    Dec. 1, 2022

(30) Foreign Application Priority Data

Mar. 15, 2018 (CN) .................. 201810212171.9
Jul. 26, 2018 (CN) .................. 201810835038.9

(51) Int. Cl.
| | | |
|---|---|---|
| *C07D 213/73* | (2006.01) | |
| *C07D 213/22* | (2006.01) | |
| *C07D 241/20* | (2006.01) | |
| *C07D 401/04* | (2006.01) | |
| *C07D 401/12* | (2006.01) | |
| *C07D 401/14* | (2006.01) | |
| *C07D 405/12* | (2006.01) | |
| *C07D 405/14* | (2006.01) | |
| *C07D 409/12* | (2006.01) | |
| *C07D 409/14* | (2006.01) | |
| *C07D 413/12* | (2006.01) | |
| *C07D 417/12* | (2006.01) | |
| *C07D 417/14* | (2006.01) | |

(52) U.S. Cl.
CPC ......... *C07D 213/73* (2013.01); *C07D 213/22* (2013.01); *C07D 241/20* (2013.01); *C07D 401/04* (2013.01); *C07D 401/12* (2013.01); *C07D 401/14* (2013.01); *C07D 405/12* (2013.01); *C07D 405/14* (2013.01); *C07D 409/12* (2013.01); *C07D 409/14* (2013.01); *C07D 413/12* (2013.01); *C07D 417/12* (2013.01); *C07D 417/14* (2013.01)

(58) Field of Classification Search
CPC .. C07D 213/73; C07D 213/22; C07D 241/20; C07D 401/04; C07D 401/12; C07D 401/14; C07D 405/12; C07D 405/14; C07D 409/12; C07D 409/14; C07D 413/12; C07D 417/12; C07D 417/14
See application file for complete search history.

(56) References Cited

FOREIGN PATENT DOCUMENTS

| WO | 2004004720 | * | 1/2004 |
| WO | 2004004720 A1 | | 1/2004 |
| WO | 2004076412 A2 | | 9/2004 |
| WO | 2005002673 | * | 1/2005 |
| WO | 2005002673 A1 | | 1/2005 |

OTHER PUBLICATIONS

International Search Report for PCT/CN2019/078006 dated Jun. 13, 2019, ISA/CN.
W. A. Robinson, et al. Stimulation of Bone Marrow Colony Growth In Vitro by Human Urine, Blood, vol. 33, No. 3, pp. 396-399, Mar. 1969.
Adrienne M. Flanagan, MD, et al. Update on the biologic effects of macrophage colony-stimulating factor, Curr Opin Hematol. 1998, 5:181-5.
J. Schiessinger, et al. Growth Factor signaling by Receptor Tyrosine Kinases, Neuron, vol. 9, 383-391, Sep. 1992.

\* cited by examiner

*Primary Examiner* — D Margaret M Seaman
(74) *Attorney, Agent, or Firm* — Yue (Robert) Xu; Apex Attorneys at Law, LLP

(57) ABSTRACT

Provided herein are compounds of formula (I) having activity on a receptor protein tyrosine kinase, wherein $R^1$, $R^2$, $R^3$, A, Q, Z, X and W are set forth in the description, as well as solvates, hydrates, tautomers or pharmaceutically acceptable salts thereof.

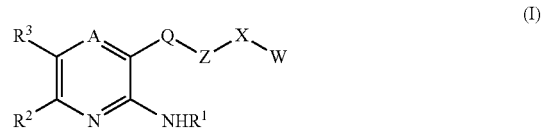

(I)

10 Claims, No Drawings

HETEROARYL COMPOUNDS AS KINASE INHIBITOR

This application is the national phase of International Application No. PCT/CN2019/078006, titled "HETEROARYL COMPOUNDS AS KINASE INHIBITOR", filed on Mar. 13, 2019, which claims the priority of Chinese Patent Application No. 201810212171.9, filed on Mar. 15, 2018 and Chinese Patent Application No. 201810835038.9, filed on Jul. 26, 2018, filed with China National Intellectual Property Administration, and titled with "HETEROARYL COMPOUNDS AS KINASE INHIBITOR", and the disclosures of which are hereby incorporated by reference.

FIELD OF THE INVENTION

The present invention relates to a compound having kinase inhibitory activity and its use in the field of medicine. More specifically, the present invention provides heteroaryl compounds having protein tyrosine kinase activity. The information provided is intended solely to assist the understanding of the reader. None of the information provided nor references cited is admitted to be prior art to the present invention. Each of the references cited is incorporated herein in its entirety and for any purpose.

BACKGROUND OF THE INVENTION

Protein tyrosine kinase can catalyze a variety of substrate proteins tyrosine residues to phosphorylate, and plays an important role in modulating cell growth, proliferation and differentiation. The aberrant kinase activity is associated with many human diseases, including cancer, autoimmune diseases and inflammatory diseases. As a mediator of cell signaling, protein tyrosine kinase can be a potential target of small molecule kinase inhibitors for modulating cell function, which is used for drug design.

One of the prime aspects of PTK activity is their involvement with growth factor receptors. The growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn effect numerous cellular responses, such as cell division (proliferation), cell differentiation, cell growth, and expression of the metabolism of the extracellular microenvironment, etc. For a more complete discussion, see Schiessinger and Ullrich, Neuron, 9:303-391 (1992), which is incorporated by reference, including any drawings, as if fully set forth herein.

The growth factor receptors with PTK activity are known as receptor tyrosine kinase ("RTKs"). They comprise a large family of transmembrane receptors with diverse biological activity. At present, at least 19 distinct subfamilies of RTKs have been identified. An example of these is the subfamily designated the "HER" RTKs, which include EGFR (epithelial growth factor receptor), HER2, HER3 and HER4. These RTKs consist of an extracellular glycosylated ligand binding domain, a transmembrane domain, and an intracellular cytoplasmic catalytic domain that can phosphorylate tyrosine residues on proteins.

Another RTK subfamily consists of insulin receptor (IR), insulin-like growth factor 1 receptor (IGF-1R) and insulin receptor-related receptor (IRR). IR and IGF-1R interact with insulin, IGF-I and IGF-II to form a heterotetramer of two entirely extracellular glycosylated α subunits and two β subunits which cross the cell membrane and which contain the tyrosine kinase domain.

A third RTK subfamily is referred to as the platelet derived growth factor receptor ("PDGFR") group, which includes PDGFR α, PDGFR ρ, Flt 3, c-kit, and c-fms. These receptors consist of glycosylated extracellular domains composed of variable numbers of immunoglobulin-like loops and an intracellular domain wherein the tyrosine kinase domain is interrupted by unrelated amino acid sequences.

Another group which, because of its similarity to the PDGFR subfamily, is sometimes subsumed into the later group is the fetus liver kinase ("flk") receptor subfamily. The group is believed to be made up of kinase insert domain-receptor fetal liver kinase-1 (KDR/FLK-1), flk-1R, flk-4 and fms-like tyrosine kinase (flt-1).

A further member of the tyrosine kinase growth factor receptor family is the fibroblast growth factor ("FGF") receptor subgroup. The group consists of four receptors, FGFR1-4, and seven ligands, FGF1-7. While not yet well defined, it appears that the receptors consist of a glycosylated extracellular domain containing a variable number of immunoglobulin like loops and an intracellular domain in which the tyrosine kinase sequence is interrupted by regions of unrelated amino acid sequences.

Still another member of the tyrosine kinase growth factor receptor family is the vascular endothelial growth factor ("VEGF") receptor subgroup. VEGF is a dimeric glycoprotein similar to PDGF but has different biological functions and target cells specificity in vivo. In particular, VEGF is presently thought to play an essential role in vasculogenesis and angiogenesis.

Still another member of the tyrosine kinase growth factor receptor group is MET, often referred to as c-Met, also known as human hepatocyte growth factor receptor tyrosine kinase (hHGFR). c-Met is thought to play a role in primary tumor growth and metastasis.

A more complete listing of the known RTK subfamilies is described in Plowman et al., DN&P, 7(6): 334-339 (1994), which is incorporated by reference, including any drawings, as if fully set forth herein.

The colony stimulating factor 1 receptor (CSF-1R), also known as macrophage colony stimulating factor receptor (M-CSFR)) and CD115 (differentiation cluster 115), is a cell surface protein encoded by the CSF-1R gene (also known as c-fms) in the human body. c-fms is a III transmembrane receptor protein tyrosine kinase (receptor protein tyrosinekinases, RPTKs), which regulates the key signal transduction cascade reactions that regulate cell growth and proliferation. The receptor consists of five immunoglobulin (IG) domains, one transmembrane domains, and a separate cytoplasmic kinase domain separated by the kinase inserting part.

c-fms was originally a member of the gene family isolated from the Susan McDonough strain of feline sarcoma viruses. The cellular proto-oncogene FMS (c-fms, cellular feline McDonough sarcoma) codes for the receptor of macrophage Colony-Stimulating Factor (M-CSF). c-fms is crucial for the growth and differentiation of monocyte-macrophage lineage, and upon binding of M-CSF to the extracellular domain of c-fms, the receptor dimerizes and transautophosphorylates cytoplasmic tyrosine residues.

M-CSF, originally described by Robinson and co-workers (Blood. 1969, 33:396-9), is a cytokine that controls the production, differentiation and function of macrophages. M-CSF stimulates the differentiation of progenitor cells into mature monocytes and prolongs the survival of monocytes. Furthermore, M-CSF enhances cytotoxicity; superoxide production, phagocytosis, chemotaxis, and secondary cytokine production of additional factors in monocytes and macrophages. Examples of such additional factors include granulocyte colony-stimulating factor (G-CSF), interleukin-6 (IL-6), and interleukin-8 (IL-8). M-CSF stimulates hematopoiesis, promotes the differentiation and proliferation of osteoclast progenitor cells, and has profound effects on lipid metabolism. Furthermore, M-CSF is important in pregnancy. Physiologically, large amounts of M-CSF are produced in the placenta, and M-CSF is believed to plays an essential role in trophoblast differentiation (Motoyoshi, Int J. Hematol. 1998, 67:109-22). The elevated serum levels of M-CSF in early pregnancy may participate in the immunologic mechanisms responsible for the maintenance of the pregnancy (Flanagan & Lader, Curr Opin Hematol. 1998, 5:181-5).

Related to c-fms and c-kit are two kinds of platelet derived growth factor receptors, a (alpha) (i.e., pdgfra) and β (beta) (pdgfrb) (PDGF). The gene coding for pdgfra is located on chromosome 4q11-q12 in the same region of chromosome 4 as the oncogene coding for c-kit. The genes coding for pdgfra and c-fms appear to have evolved from a common ancestral gene by gene duplication, inasmuch as these two genes are tandemly linked on chromosome 5. They are oriented head-to-tail with the 5-prime exon of the c-fms gene located only 500 bp from the last 3-prime exon of the gene coding for pdgfra. The observation that production of M-CSF, the major macrophage growth factor, is increased in tissues during inflammation points out a role for c-fms in diseases, such as for example inflammatory diseases. More particularly, because elevated levels of M-CSF are found in the disease state, modulation of the activity of c-fms can ameliorate disease associated with increased levels of M-CSF.

DETAILED DESCRIPTION OF THE INVENTION

The present invention provides compounds with tyrosine kinase inhibitory activity.

The present invention described compounds comprising at least a compound of Formula (I).

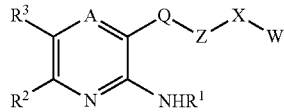

Formula (I)

Wherein:
A is selected from N or $CR^2$;
$R^1$ is selected from H, $C_1$-$C_5$ alkyl, $C_3$-$C_6$ cycloalkyl, $C(O)C_1$-$C_3$ alkyl, $S(O)_2(C_1$-$C_3)$ alkyl or $S(O)_2(C_3$-$C_6)$ cycloalkyl;
$R^2$ is selected from H, halogen, OH, $NR^5R^6$, CN, $C_1$-$C_5$ alkyl;
$R^3$ is selected from H, halogen, $C_6$-$C_{12}$ aryl, 5-12 membered heteroaryl, OH, $NO_2$, CN, $O(C_1$-$C_5)$alkyl, $(C_1$-$C_5)$heteroalkyl, $O(C_3$-$C_6)$cycloalkyl, $O(C_3$-$C_6)$heterocycloalkyl, $(C_1$-$C_3)$alkyl$(C_3$-$C_6)$heterocycloalkyl, $C_2$-$C_5$ alkenyl, $C_2$-$C_5$ alkynyl, $C_3$-$C_7$ cycloalkyl, $C_3$-$C_6$ heterocycloalkyl, $NR^5R^6$, $C(O)R^8$, $P(O)R^8R^9$, $S(O)_n(C_1$-$C_3)$ alkyl or $S(O)_n(C_3$-$C_6)$ cycloalkyl, Wherein n=0, 1 or 2; hydrogens in $R^3$ are optionally substituted by one or more $R^7$ groups independently, and the adjacent $R^7$ groups can join to form a 4-12 membered ring;
Q is selected from $CHR^5CHR^6$, O, $OC(R^5R^6)$, $C(R^5R^6)$, CO, $NR^5C(O)$, $NR^5S(O)_2$, CH=CH, C≡C, $S(O)_n$, $S(O)_n(C_1$-$C_3)$alkyl, wherein n=0, 1 or 2;
Z is selected from $C_6$-$C_{10}$ aryl, 5-10 membered heteroaryl, and each hydrogen on the ring may be substituted by $R^4$;
X is selected from $O(C_0$-$C_3)$alkyl, $NR^5(C_0$-$C_3)$ alkyl, $NR^5C(O)$, $NR^5S(O)_2$, $C(O)NR^5$, $S(O)_2NR^5$, $N(R^5)C(O)N(R^6)$, $N(R^5)C(S)N(R^6)$;
W is selected from $C_6$-$C_{12}$ aryl, 5-12 membered heteroaryl, wherein the hydrogens on the ring may be substituted by one or more $R^7$ groups independently;
$R^4$ is selected from halogen, OH, CN, $O(C_1$-$C_5)$alkyl, $C_1$-$C_5$alkyl;
Each $R^5$ and $R^6$ is independently selected from H, $C_1$-$C_3$ alkyl, $C_3$-$C_6$ cycloalkyl, $C(O)C_1$-$C_3$ alkyl, $S(O)_2(C_1$-$C_3)$alkyl or $S(O)_2(C_3$-$C_6)$cycloalkyl; $R^5$ and $R^6$ can join to form a 3-6 membered ring; or $R^1$ can join with $R^5$ or $R^6$ to form a 5-7 membered ring.
$R^7$ is selected from H, halogen, $C_6$-$C_{12}$ aryl, 5-12 membered heteroaryl, OH, $NO_2$, CN, $(C_1$-$C_5)$alkyl, $O(C_1$-$C_6)$alkyl, $(C_1$-$C_5)$heteroalkyl, $O(C_3$-$C_7)$cycloalkyl, $O(C_3$-$C_6)$heterocycloalkyl. $(C_1$-$C_3)$alkyl$(C_3$-$C_6)$ heterocycloalkyl, $C_2$-$C_5$ alkenyl, $C_2$-$C_5$ alkynyl, $C_3$-$C_6$ cycloalkyl, $C_3$-$C_6$ heterocycloalkyl, $NR^5R^6$, $C(O)R^8$, $P(O)R^8R^9$, $S(O)_n(C_1$-$C_3)$alkyl or $S(O)_n(C_3$-$C_6)$cycloalkyl, wherein n=0, 1 or 2; and the two adjacent $R^7$ groups can join to form a 4-12 membered ring.
$R^8$ and $R^9$ is independently selected from $C_1$-$C_3$ alkyl, $O(C_1$-$C_3)$alkyl, $NR^5R^6$.

In any and all embodiments, substituents may be selected from a subset of the selected items listed. For example, in some implementations, $R^3$ is selected from H or halogen.

In some implementations, $R^3$ is selected from H or halogen; W is selected from phenyl or 5-10 membered heteroaryl, and the hydrogen on the ring may be substituted by one or more $R^7$ groups independently, and the two adjacent $R^7$ can join to form a 5-7 membered ring; and $R^7$ is selected from H, halogen, OH, $NO_2$, CN, $O(C_1$-$C_3)$alkyl, $(C_1$-$C_5)$ heteroalkyl, $O(C_3$-$C_6)$cycloalkyl, $O(C_3$-$C_6)$ heterocycloalkyl, $C_1$-$C_5$ alkyl, alkenyl, alkynyl, $C_3$-$C_6$ cycloalkyl, $C_3$-$C_6$ heterocycloalkyl, $NH_2$, $N((C_1$-$C_2)$alkyl$)_2$, $NH(C_1$-$C_2)$alkyl, $C(O)(C_1$-$C_2)$alkyl, $C(O)O(C_1$-$C_2)$alkyl, $P(O)((C_1$-$C_2)$alkyl$)_2$, $SO_2$ cyclopropyl, $S(O)_n(C_1$-$C_3)$alkyl, wherein n=0, 1 or 2.

In some embodiments, W is selected from phenyl or 5-10 membered heteroaryl, and the hydrogen on the ring may be substituted by one or more $R^7$ groups independently, and one of the substituents must be selected from $NH_2$, $N((C_1$-$C_2)$ alkyl$)_2$, $NH(C_1$-$C_2)$alkyl, $C(O)(C_1$-$C_2)$alkyl, $C(O)O(C_1$-$C_2)$ alkyl, $P(O)((C_1$-$C_2)$alkyl$)_2$, $SO_2$ cyclopropyl, $S(O)_n(C_1$-$C_3)$ alkyl, wherein n=0, 1 or 2, and the two adjacent $R^7$ groups can join to form a 5-7 membered ring; In further implementation, W is selected from phenyl, wherein the hydrogens on the ring may be substituted by one or more $R^7$ groups independently, one of the substituents must be selected from $NH_2$, $N((C_1$-$C_2)$alkyl$)_2$, $NH(C_1$-$C_2)$alkyl, $C(O)(C_1$-$C_2)$alkyl, $C(O)O(C_1$-$C_2)$alkyl, $P(O)((C_1$-$C_2)$alkyl$)_2$, $SO_2$ cyclopropyl, $S(O)_n(C_1$-$C_3)$alkyl, wherein n=0, 1 or 2, and the two adjacent $R^7$ groups can join to form a 5-7 membered ring.

In some embodiments, W is selected from phenyl or 5-10 membered heteroaryl, and the hydrogen on the ring may be substituted by one or more $R^7$ groups independently, and one of the substituents must be selected from $NH_2$, $N((C_1$-$C_2)$ alkyl$)_2$, $NH(C_1$-$C_2)$alkyl, $C(O)(C_1$-$C_2)$alkyl, $C(O)O(C_1$-$C_2)$ alkyl, P(O)((C$_1$-C$_2$)alkyl)$_2$, SO$_2$ cyclopropyl, S(O)$_n$(C$_1$-C$_3$) alkyl, wherein n=0, 1 or 2, and the two adjacent R$^7$ groups can join to form a 5-7 membered ring; R$^3$ is selected from phenyl, 5-10 membered heteroaryl, wherein the hydrogens on the ring may be substituted by halogen, OH, NO$_2$, CN, O(C$_1$-C$_3$)alkyl, (C$_1$-C$_5$)heteroalkyl, O(C$_3$-C$_6$)cycloalkyl, O(C$_3$-C$_6$)heterocycloalkyl, C$_1$-C$_5$ alkyl, CH=CH, C≡C, C$_3$-C$_6$ cycloalkyl, C$_3$-C$_6$ heterocycloalkyl, N((C$_1$-C$_2$)alkyl)$_2$, NH(C$_1$-C$_2$)alkyl, C(O)(C$_1$-C$_2$)alkyl, C(O)O(C$_1$-C$_2$)alkyl, P(O)((C$_1$-C$_2$)alkyl)$_2$, SO$_2$ cyclopropyl, S(O)$_n$(C$_1$-C$_3$) alkyl, wherein n=0, 1 or 2; and the adjacent substituted groups in R$^3$ can join to form a 5-7 membered ring; In further implementation, wherein W is selected from phenyl or 5-10 membered heteroaryl, and the hydrogen on the ring may be substituted by one or more R$^7$ groups independently, and one of the substituents must be selected from NH$_2$, N((C$_1$-C$_2$)alkyl)$_2$, NH(C$_1$-C$_2$)alkyl, C(O)(C$_1$-C$_2$)alkyl, C(O)O(C$_1$-C$_2$)alkyl, P(O)((C$_1$-C$_2$)alkyl)$_2$, SO$_2$ cyclopropyl, S(O)$_n$(C$_1$-C$_3$)alkyl, wherein n=0, 1 or 2, and the two adjacent R$^7$ groups can join to form a 5-7 membered ring; R$^3$ is selected from phenyl, pyrazolyl, pyridyl, wherein the hydrogens on the ring may be substituted by halogen, CN, O(C$_1$-C$_3$)alkyl, C$_1$-C$_3$alkyl, C$_3$-C$_6$cycloalkyl, (C$_1$-C$_5$)heteroalkyl, C$_3$-C$_6$ heterocycloalkyl, N((C$_1$-C$_2$)alkyl)$_2$, NH(C$_1$-C$_2$)alkyl; and the adjacent substituted groups in R$^3$ can join to form a 5-7 membered ring.

In some embodiments, W is selected from phenyl, wherein the hydrogens on the ring may be substituted by one or more R$^7$ groups independently, one of the substituents must be selected from NH$_2$, N((C$_1$-C$_2$)alkyl)$_2$, NH(C$_1$-C$_2$)alkyl, C(O)(C$_1$-C$_2$)alkyl, C(O)O(C$_1$-C$_2$)alkyl, P(O)((C$_1$-C$_2$)alkyl)$_2$, SO$_2$ cyclopropyl, S(O)$_n$(C$_1$-C$_3$)alkyl, wherein n=0, 1 or 2, and the two adjacent R$^7$ groups can join to form a 5-7 membered ring; R$^3$ is selected from phenyl, 5-10 membered heteroaryl, wherein the hydrogens on the ring may be substituted by halogen. OH, NO$_2$, CN, O(C$_1$-C$_3$)alkyl, (C$_1$-C$_5$)heteroalkyl, O(C$_3$-C$_6$)cycloalkyl, O(C$_3$-C$_6$)heterocycloalkyl, C$_1$-C$_5$ alkyl, CH=CH, C≡C, C$_3$-C$_6$ cycloalkyl, C$_3$-C$_6$ heterocycloalkyl, N((C$_1$-C$_2$)alkyl)$_2$, NH(C$_1$-C$_2$)alkyl, C(O)(C$_1$-C$_2$)alkyl, C(O)O(C$_1$-C$_2$)alkyl, P(O)((C$_1$-C$_2$)alkyl)$_2$, SO$_2$ cyclopropyl, S(O)$_n$(C$_1$-C$_3$)alkyl, wherein n=0, 1 or 2; and the adjacent substituted groups in R$^3$ can join to form a 5-7 membered ring; In further implementation, W is selected from phenyl, wherein the hydrogens on the ring may be substituted by one or more R$^7$ groups independently, one of the substituents must be selected from NH$_2$, N((C$_1$-C$_2$)alkyl)$_2$, NH(C$_1$-C$_2$)alkyl, C(O)(C$_1$-C$_2$)alkyl, C(O)O(C$_1$-C$_2$)alkyl, P(O)((C$_1$-C$_2$)alkyl)$_2$, SO$_2$ cyclopropyl, S(O)$_n$(C$_1$-C$_3$)alkyl, wherein n=0, 1 or 2, and the two adjacent R$^7$ groups can join to form a 5-7 membered ring; R$^3$ is selected from phenyl, pyrazolyl, pyridyl, wherein the hydrogens on the ring may be substituted by halogen, CN, O(C$_1$-C$_3$)alkyl, C$_1$-C$_3$alkyl, C$_3$-C$_6$ cycloalkyl, (C$_1$-C$_5$)heteroalkyl, C$_3$-C$_6$ heterocycloalkyl, N((C$_1$-C$_2$)alkyl)$_2$, NH(C$_1$-C$_2$)alkyl; and the adjacent substituted groups in R$^3$ can join to form a 5-7 membered ring.

In some embodiments, A is selected from N; R$^3$ is selected from H or halogen; W is selected from phenyl or 5-10 membered heteroaryl, and the hydrogen on the ring may be substituted by one or more R$^7$ groups independently, and the two adjacent R$^7$ can join to form 5-7 membered ring; and R$^7$ is selected from H, halogen, OH, NO$_2$, CN, O(C$_1$-C$_3$)alkyl, (C$_1$-C$_5$)heteroalkyl, O(C$_3$-C$_6$)cycloalkyl, O(C$_3$-C$_6$) heterocycloalkyl, C$_1$-C$_5$ alkyl, alkenyl, alkynyl, C$_3$-C$_6$ cycloalkyl, C$_3$-C$_6$ heterocycloalkyl, NH$_2$, N((C$_1$-C$_2$)alkyl)$_2$, NH(C$_1$-C$_2$) alkyl, C(O)(C$_1$-C$_2$)alkyl, C(O)O(C$_1$-C$_2$)alkyl, P(O)((C$_1$-C$_2$) alkyl)$_2$, SO$_2$ cyclopropyl, S(O)$_n$(C$_1$-C$_3$)alkyl, wherein n=0, 1 or 2.

In some embodiments, A is selected from N; W is selected from phenyl, wherein the hydrogens on the ring may be substituted by one or more R$^7$ groups independently, one of the substituents must be selected from NH$_2$, N((C$_1$-C$_2$)alkyl)$_2$, NH(C$_1$-C$_2$)alkyl, C(O)(C$_1$-C$_2$)alkyl, C(O)O(C$_1$-C$_2$)alkyl, P(O)((C$_1$-C$_2$)alkyl)$_2$, SO$_2$ cyclopropyl, S(O)$_n$(C$_1$-C$_3$) alkyl, wherein n=0, 1 or 2, and the two adjacent R$^7$ groups can join to form a 5-7 membered ring; R$^3$ is selected from phenyl, 5-10 membered heteroaryl, wherein the hydrogens on the ring may be substituted by halogen, OH, NO$_2$, CN, O(C$_1$-C$_3$)alkyl, (C$_1$-C$_5$)heteroalkyl, O(C$_3$-C$_6$)cycloalkyl, O(C$_3$-C$_6$)heterocycloalkyl, C$_1$-C$_5$alkyl, CH=CH, C≡C, C$_3$-C$_6$ cycloalkyl, C$_3$-C$_6$ heterocycloalkyl, N((C$_1$-C$_2$)alkyl)$_2$, NH(C$_1$-C$_2$)alkyl, C(O)(C$_1$-C$_2$)alkyl, C(O)O(C$_1$-C$_2$) alkyl, P(O)((C$_1$-C$_2$)alkyl)$_2$, SO$_2$ cyclopropyl, S(O)$_n$(C$_1$-C$_3$) alkyl, wherein n=0, 1 or 2; and the adjacent substituted groups in R$^3$ can join to form a 5-7 membered ring; In further implementation, A is selected from N; W is selected from phenyl, wherein the hydrogens on the ring may be substituted by one or more R$^7$ groups independently, one of the substituents must be selected from NH$_2$, N((C$_1$-C$_2$) alkyl)$_2$, NH(C$_1$-C$_2$)alkyl, C(O)(C$_1$-C$_2$)alkyl, C(O)O(C$_1$-C$_2$) alkyl, P(O)((C$_1$-C$_2$)alkyl)$_2$, SO$_2$ cyclopropyl, S(O)$_n$(C$_1$-C$_3$) alkyl, wherein n=0, 1 or 2, and the two adjacent R$^7$ groups can join to form a 5-7 membered ring; R$^3$ is selected from phenyl, pyrazolyl, pyridyl, wherein the hydrogens on the ring may be substituted by halogen, CN, O(C$_1$-C$_3$)alkyl, C$_1$-C$_3$alkyl, C$_3$-C$_6$cycloalkyl, (C$_1$-C$_5$)heteroalkyl, C$_3$-C$_6$ heterocycloalkyl, N((C$_1$-C$_2$)alkyl)$_2$, NH(C$_1$-C$_2$)alkyl; and the adjacent substituted groups in R$^3$ can join to form a 5-7 membered ring;

A preferred embodiment of the above-listed embodiments has a compound represented by the formula (Ia):

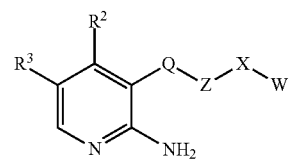

Formula (Ia)

Wherein:
R$^2$ is selected from H, halogen. OH, NR$^5$R$^6$, CN, C$_1$-C$_5$ alkyl;
Q is selected from CHR$^5$CHR$^6$, O, OC(R$^5$R$^6$), C(R$^5$R$^6$), CO, NR$^5$C(O), NR$^5$S(O)$_2$, CH=CH, C≡C, S(O)$_n$, S(O)$_n$(C$_1$-C$_3$)alkyl, wherein n=0, 1 or 2;
Z is selected from phenyl or pyridyl, wherein the hydrogens on the ring may be substituted by R$^4$;
X is selected from O(C$_0$-C$_3$)alkyl, NR$^5$(C$_0$-C$_3$)alkyl, NR$^5$C(O), NR$^5$S(O)$_2$, C(O)NR$^5$, S(O)$_2$NR$^5$, N(R$^5$)C(O)N(R$^6$), N(R$^5$)C(S)N(R$^6$);
R$^4$ is selected from halogen, OH, CN, O(C$_1$-C$_5$)alkyl, C$_1$-C$_5$ alkyl;
Each R$^5$ and R$^6$ is independently selected from H, C$_1$-C$_3$ alkyl, or R$^5$ and R$^6$ can join to form a 3-6 membered ring:
In some implementations of this preferred embodiment, R$^2$ is selected from H; in some further implementations, R$^2$ is selected from H; Z is selected from phenyl or pyridyl, wherein the hydrogens on the ring may be substituted by one or more R⁴ groups independently, and R⁴ is selected from halogen, OH, CN, O(C₁-C₃)alkyl, C₁-C₃ alkyl;

In some implementations of this preferred embodiment, Z is selected from phenyl or pyridyl, wherein the hydrogens on the ring may be substituted by one or mom R⁴ groups independently, and R⁴ is selected from halogen, OH, CN, O(C₁-C₃)alkyl, C₁-C₃ alkyl; In some further implementations, Z is selected from phenyl or pyridyl, wherein the hydrogens on the ring may be substituted by one or more R⁴ groups independently, and R⁴ is selected from halogen, OH, CN, O(C₁-C₃)alkyl, C₁-C₃ alkyl; Q is selected from OC(R⁵R⁶), and each R⁵ and R⁶ is independently selected from H, C₁-C₃ alkyl, or R⁵ and R⁶ can join to form a 3-6 membered ring; In the further implementation, Z is selected from phenyl or pyridyl, wherein the hydrogens on the ring may be substituted by one or more R⁴ groups independently, and R⁴ is selected from halogen, OH, CN, O(C₁-C₃)alkyl, C₁-C₃ alkyl; Q is selected from OC(R⁵R⁶), one of R⁵ and R⁶ is dydrogen, the other is selected from C₁-C₃ alkyl;

In some embodiments of this preferred embodiment, R² is selected from H; Z is selected from phenyl or pyridyl, wherein the hydrogens on the ring may be substituted by one or more R⁴ groups independently, and R⁴ is selected from halogen, OH, CN, O(C₁-C₃)alkyl, C₁-C₃ alkyl. In some further embodiments, R² is selected from H; Z is selected from phenyl or pyridyl, wherein the hydrogens on the ring may be substituted by one or more R⁴ groups independently, and R⁴ is selected from halogen, OH, CN, O(C₁-C₃)alkyl, C₁-C₃ alkyl; Q is selected from OC(RR), and each R⁵ and R⁶ is independently selected from H, C₁-C₃ alkyl, or R⁵ and R⁶ can join to form a 3-6 membered ring; In a further implementation, R² is selected from H; Z is selected from phenyl or pyridyl, wherein the hydrogens on the ring may be substituted by one or more R⁴ groups independently, and R⁴ is selected from halogen, OH, CN, O(C₁-C₃)alkyl, C₁-C₃ alkyl; Q is selected from OC(R⁵R⁶), one of R⁵ and R⁶ is dydrogen, the other is selected from C₁-C₃ alkyl:

In some embodiments of this preferred embodiment, X is selected from OCH₂, NHCH₂, NHC(O), NHS(O)₂, C(O)NH, S(O)₂NH, NHC(O)NH, NHC(S)NH. In some further embodiments, X is selected from NHC(O), C(O)NH, NHC(O)NH, NHC(O)NH, NHC(S)NH.

In some implementations of this preferred embodiment, Z is selected from phenyl or pyridyl, wherein the hydrogens on the ring may be substituted by one or more R⁴ groups independently, and R⁴ is selected from halogen, OH, CN, O(C₁-C₃)alkyl, C₁-C₃ alkyl; X is selected from OCH₂, NHCH₂, NHC(O), NHS(O)₂, C(O)NH, S(O)₂NH, NHC(O)NH, NHC(S)NH; In some further implementations, Z is selected from phenyl or pyridyl, wherein the hydrogens on the ring may be substituted by one or more R⁴ groups independently, and R⁴ is selected from halogen, OH, CN, O(C₁-C₃)alkyl, C₁-C₃ alkyl; Q is selected from OC(R⁵R⁶), and each R⁵ and R⁶ is independently selected from H, C₁-C₃ alkyl, or R⁵ and R⁶ can join to form a 3-6 membered ring; X is selected from OCH₂, NHCH₂, NHC(O), NHS(O)₂, C(O)NH, S(O)₂NH, NHC(O)NH, NHC(S)NH; In the further implementation, Z is selected from phenyl or pyridyl, wherein the hydrogens on the ring may be substituted by one or more R⁴ groups independently, and R⁴ is selected from halogen, OH, CN, O(C₁-C₃)alkyl, C₁-C₃ alkyl; Q is selected from OC(R⁵R⁶), one of R⁵ and R⁶ is dydrogen, the other is selected from C₁-C₃ alkyl; X is selected from OCH₂, NHCH₂, NHC(O), NHS(O)₂, C(O)NH, S(O)₂NH, NHC(O)NH, NHC(S)NH.

In some embodiments of this preferred embodiment, R² is selected from H; Z is selected from phenyl or pyridyl, wherein the hydrogens on the ring may be substituted by one or more R⁴ groups independently, and R⁴ is selected from halogen, OH, CN, O(C₁-C₃)alkyl, C₁-C₃ alkyl; X is selected from NHC(O). C(O)NH, NHC(O)NH, NHC(S)NH. In some further embodiments. R² is selected from H; Z is selected from phenyl or pyridyl, wherein the hydrogens on the ring may be substituted by one or more R⁴ groups independently, and R⁴ is selected from halogen, OH, CN, O(C₁-C₃)alkyl, C₁-C₃ alkyl; Q is selected from OC(R⁵R⁶), and each R⁵ and R⁶ is independently selected from H, C₁-C₃ alkyl, or R⁵ and R⁶ can join to form a 3-6 membered ring; X is selected from NHC(O), C(O)NH, NHC(O)NH, NHC(S)NH. In a further implementation, R² is selected from H; Z is selected from phenyl or pyridyl, wherein the hydrogens on the ring may be substituted by one or more R⁴ groups independently, and R⁴ is selected from halogen, OH, CN, O(C₁-C₃)alkyl, C₁-C₃ alkyl; Q is selected from OC(R⁵R⁶), one of R⁵ and R⁶ is dydrogen, the other is selected from C₁-C₃ alkyl; X is selected from NHC(O), C(O)NH, NHC(O)NH, NHC(S)NH.

The compound described above is further preferably a compound of the formula (Ib):

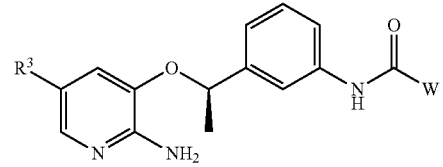

formula (Ib)

Wherein:
R³ is selected from H, halogen, C₆-C₁₀ phenyl, 5-10 membered heteroaryl, C₃-C₆ heteroalkyl; the hydrogens in R³ are optionally substituted by one or more R⁷ groups independently, and the adjacent R⁷ groups can join to form a 5-7 membered ring;
W is selected from C₆-C₁₀ aryl, 5-10 membered heteroaryl, wherein the hydrogens on the rings may be substituted by one or more R⁷ groups independently;
R⁷ is selected from H, halogen, OH, NO₂, CN, O(C₁-C₃)alkyl, (C₁-C₅)heteroalkyl, O(C₃-C₆)cycloalkyl, O(C₃-C₆)heterocycloalkyl, C₁-C₅ alkyl, C=C, C≡C, C₃-C₆ cycloalkyl, C₃-C₆ heterocycloalkyl, NR⁵R⁶, C(O)(C₁-C₂)alkyl, C(O)O(C₁-C₂)alkyl, P(O)((C₁-C₂)alkyl)₂, SO₂ cyclopropyl, S(O)ₙ(C₁-C₃)alkyl, wherein n=0, 1 or 2; and the two adjacent R⁷ groups can join to form a 5-7 membered ring;
Each R⁵ and R⁶ is independently selected from H, C₁-C₃ alkyl, C₃-C₆ cycloalkyl, C(O)C₁-C₃ alkyl, S(O)₂(C₁-C₃)alkyl or S(O)₂(C₃-C₆)cycloalkyl; or R⁵ and R⁶ is combined together to form a 3-6 membered ring;

In some embodiments, R³ in the formula (Ib) is selected from H, halogen; W is selected from phenyl or 5-10 membered heteroaryl, wherein the hydrogens on the ring may be substituted by one or more R⁷ groups independently, and the two adjacent R⁷ groups can join to form a 5-7 membered ring; R⁷ is selected from halogen, OH, NO₂, CN, O(C₁-C₃) alkyl, (C₁-C₅) heteroalkyl, O(C₃-C₆)cycloalkyl, O(C₃-C₆) heterocycloalkyl, C₁-C₅ alkyl, C=C, C≡C, C₃-C₆ cycloalkyl, C₃-C₆ heterocycloalkyl, N((C₁-C₂)alkyl)₂, NH(C₁-C₂) alkyl, C(O)(C₁-C₂)alkyl, C(O)O(C₁-C₂)alkyl, P(O)((C₁-C₂) alkyl)₂, SO₂ cyclopropyl, S(O)ₙ(C₁-C₃)alkyl, wherein n=0, 1 or 2.

In some embodiments, $R^3$ in the formula (Ib) is selected from phenyl, 5-10 membered heteroaryl, $C_3$-$C_6$ heterocycloalkyl, wherein the hydrogens on the ring may be substituted by halogen, OH, $NO_2$, CN, $O(C_1$-$C_3)$alkyl, $(C_1$-$C_5)$ heteroalkyl, $O(C_3$-$C_6)$cycloalkyl, $O(C_3$-$C_6)$ heterocycloalkyl, $C_1$-$C_5$ alkyl, C=C, C≡C, $C_3$-$C_6$ cycloalkyl, $C_3$-$C_6$ heterocycloalkyl, $N((C_1$-$C_2)$alkyl$)_2$, $NH(C_1$-$C_2)$alkyl, $C(O)(C_1$-$C_2)$alkyl, $C(O)O(C_1$-$C_2)$alkyl, $P(O)((C_1$-$C_2)$alkyl$)_2$, $SO_2$ cyclopropyl, $S(O)_n(C_1$-$C_3)$alkyl, wherein n=0, 1 or 2; W is selected from phenyl or 5-10 membered heteroaryl, wherein the hydrogens on the ring may be substituted by one or more $R^7$ groups independently, and one of the substituted groups should be selected from $NH_2$, $N((C_1$-$C_2)$alkyl$)_2$, $NH(C_1$-$C_2)$alkyl, $C(O)(C_1$-$C_2)$alkyl, $C(O)O(C_1$-$C_2)$alkyl, $P(O)((C_1$-$C_2)$alkyl$)_2$, $SO_2$ cyclopropyl, $S(O)_n(C_1$-$C_3)$alkyl, wherein n=0, 1 or 2, and the adjacent groups in $R^7$ or W can join to form a 5-7 membered ring; In some further embodiments, $R^3$ is selected from phenyl, pyrazolyl, pyridyl, wherein the hydrogens on the ring may be substituted by halogen, CN, $O(C_1$-$C_3)$alkyl, $C_1$-$C_3$ alkyl, $C_3$-$C_6$ cycloalkyl, $(C_1$-$C_5)$heteroalkyl, $C_3$-$C_6$ heterocycloalkyl, $N((C_1$-$C_2)$alkyl$)_2$, $NH(C_1$-$C_2)$alkyl; and the adjacent substituted groups in $R^3$ can join to form a 5-7 membered ring. In still further embodiments, $R^3$ is selected from pyrazolyl, pyridyl, wherein the hydrogens on the ring may be substituted by halogen. CN, $C_1$-$C_3$ alkyl, $C_3$-$C_6$ cycloalkyl, $(C_1$-$C_5)$ heteroalkyl, $C_3$-$C_6$ heterocycloalkyl, and the adjacent substituted groups on $R^3$ can join to form a 5-7 membered ring.

In some embodiments, $R^3$ in the formula (Ib) is selected from phenyl, pyrazolyl, pyridyl, wherein the hydrogens on the ring may be substituted by halogen, CN, $O(C_1$-$C_3)$alkyl, $C_1$-$C_3$ alkyl, $C_3$-$C_6$cycloalkyl, $(C_1$-$C_3)$heteroalkyl, $C_3$-$C_6$ heterocycloalkyl, $N((C_1$-$C_2)$alkyl$)_2$, $NH(C_1$-$C_2)$alkyl; and the adjacent substituted groups in $R^3$ can join to form a 5-7 membered ring; W is selected from phenyl, wherein the hydrogens on the ring is substituted by one or more $R^7$ groups independently, and one of the substituted groups should be selected from $N((C_1$-$C_2)$alkyl$)_2$, $C(O)(C_1$-$C_2)$ alkyl, $C(O)O(C_1$-$C_2)$ alkyl, $P(O)((C_1$-$C_2)$alkyl$)_2$, $SO_2$ cyclopropyl, $S(O)_n(C_1$-$C_3)$ alkyl, wherein n=0, 1 or 2, and the adjacent substituted groups in W can join to form a 5-7 membered ring. In some further embodiments, $R^3$ is selected from pyrazolyl, pyridyl, wherein the hydrogens on the ring may be substituted by halogen, CN, $C_1$-$C_3$ alkyl, $C_3$-$C_6$ cycloalkyl, $(C_1$-$C_5)$ heteroalkyl, $C_3$-$C_6$ heterocycloalkyl, and the adjacent substituted groups on $R^3$ can join to form a 5-7 membered ring; W is selected from phenyl, wherein the hydrogens on the ring is substituted by one or more $R^7$ groups independently, and one of the substituted groups should be selected from $N((C_1$-$C_2)$alkyl$)_2$, $C(O)(C_1$-$C_2)$ alkyl, $C(O)O(C_1$-$C_2)$ alkyl, $P(O)((C_1$-$C_2)$alkyl$)_2$, $SO_2$ cyclopropyl, $S(O)_n(C_1$-$C_3)$ alkyl, wherein n=0, 1 or 2, and the adjacent substituted groups in W can join to form a 5-7 membered ring.

More specifically, the preferred compounds of the invention are selected from any one of the following compounds:

N-(3-(((2-amino-5-chloropyridin-3-yl)oxy)methyl)phenyl)-3-methylbenzamide

N-(3-(((2-amino-5-chloropyridin-3-yl)oxy)methyl)phenyl)-3-fluorobenzamide

N-(3-(((2-amino-5-chloropyridin-3-yl)oxy)methyl)phenyl)-3-chlorobenzamide

N-(3-(((2-amino-5-chloropyridin-3-yl)oxy)methyl)phenyl)-2-fluoro-5-methylbenzamide N-(3-(((2-amino-5-chloropyridin-3-yl)oxy)methyl)phenyl)-2-fluorobenzamide N-(3-(((2-amino-5-chloropyridin-3-yl)oxy)methyl)phenyl)benzamide N-(3-(((2-amino-5-chloropyridin-3-yl)oxy)methyl)phenyl)-5-fluoro-2-methylbenzamide N-(3-(((2-amino-5-chloropyridin-3-yl)oxy)methyl)phenyl)-5-methylnicotinamide N-(3-(((2-amino-5-chloropyridin-3-yl)oxy)methyl)phenyl)-5-fluoronicotinamide N-(3-(((2-amino-5-chloropyridin-3-yl)oxy)methyl)phenyl)-5-chloronicotinamide (S)—N-(3-(1-((2-amino-5-chloropyridin-3-yl)oxy)ethyl)phenyl)-3-methylbenzamide (S)—N-(3-(1-((2-amino-5-chloropyridin-3-yl)oxy)ethyl)phenyl)-3-chlorobenzamide (S)—N-(3-(1-((2-amino-5-chloropyridin-3-yl)oxy)ethyl)phenyl)-2-fluoro-5-methylbenzamide (S)—N-(3-(1-((2-amino-5-chloropyridin-3-yl)oxy)ethyl)phenyl)-2-chloro-5-methylbenzamide (S)—N-(3-(1-((2-amino-5-chloropyridin-3-yl)oxy)ethyl)phenyl)-3-methoxybenzamide (S)—N-(3-(1-((2-amino-5-chloropyridin-3-yl)oxy)ethyl)phenyl)-5-chloronicotinamide (S)—N-(3-(1-((2-amino-5-chloropyridin-3-yl)oxy)ethyl)phenyl)-5-methylnicotinamide (S)—N-(3-(1-((2-amino-5-chloropyridin-3-yl)oxy)ethyl)phenyl)-3-cyanobenzamide (S)—N-(3-(1-((2-amino-5-chloropyridin-3-yl)oxy)ethyl)phenyl)-3-(trifluoromethoxy)benz amide (S)—N-(3-(1-((2-amino-5-chloropyridin-3-yl)oxy)ethyl)phenyl)-3-(trifluoromethyl)benzamide (S)—N-(3-(1-((2-amino-5-chloropyridin-3-yl)oxy)ethyl)phenyl)-2-chloro-3-methylbenzamide (S)—N-(3-(1-((2-amino-5-chloropyridin-3-yl)oxy)ethyl)phenyl)-2,3-dichlorobenzamide (S)—N-(3-(1-((2-amino-5-chloropyridin-3-yl)oxy)ethyl)phenyl)-2,5-dichlorobenzamide (S)—N-(3-(1-((2-amino-5-chloropyridin-3-yl)oxy)ethyl)phenyl)-3,4-dichlorobenzamide (S)—N-(3-(1-((2-amino-5-chloropyridin-3-yl)oxy)ethyl)phenyl)benzo[d][1,3]dioxole-5-carboxamide (S)—N-(3-(1-((2-amino-5-chloropyridin-3-yl)oxy)ethyl)phenyl)-3-bromobenzamide (S)—N-(3-(1-((2-amino-5-chloropyridin-3-yl)oxy)ethyl)phenyl)-3-cyclopropylbenzamide (S)—N-(3-(1-((2-amino-5-chloropyridin-3-yl)oxy)ethyl)phenyl)-3-ethynylbenzamide (R)—N-(3-(1-((2-amino-5-chloropyridin-3-yl)oxy)ethyl)phenyl)-3-methylbenzamide (R)—N-(3-(1-((2-amino-5-chloropyridin-3-yl)oxy)ethyl)phenyl)-2-chloro-5-methylbenzamide (R)—N-(3-(1-((2-amino-5-chloropyridin-3-yl)oxy)ethyl)phenyl)-3-methoxybenzamide (R)—N-(3-(1-((2-amino-5-chloropyridin-3-yl)oxy)ethyl)phenyl)-3-cyanobenzamide (R)—N-(3-(1-((2-amino-5-chloropyridin-3-yl)oxy)ethyl)phenyl)-2,5-dichlorobenzamide (R)—N-(3-(1-((2-amino-5-chloropyridin-3-yl)oxy)ethyl)phenyl)-3-ethynylbenzamide (R)—N-(3-(1-((2-amino-5-chloropyridin-3-yl)oxy)ethyl)phenyl)-3-(methylsulfonyl)benzamide (R)—N-(3-(1-((2-amino-5-chloropyridin-3-yl)oxy)ethyl)phenyl)-3-(isopropylsulfonyl)benzamide (R)—N-(3-(1-((2-amino-5-chloropyridin-3-yl)oxy)ethyl)phenyl)-3-(cyclopropylsulfonyl)benzamide (R)—N-(3-(1-((2-amino-5-chloropyridin-3-yl)oxy)ethyl)phenyl)-3-(dimethylphosphoryl)benzamide (R)—N-(3-(1-((2-amino-5-chloropyridin-3-yl)oxy)ethyl)phenyl)-3-(dimethylamino)benzamide
(R)—N-(3-(1-((2-amino-5-chloropyridin-3-yl)oxy)ethyl)phenyl)-5-methylnicotinamide
(R)—N-(3-(1-((2-amino-5-chloropyridin-3-yl)oxy)ethyl)phenyl)-2-fluoro-5-methylbenzamide
(R)—N-(3-(1-((2-amino-5-chloropyridin-3-yl)oxy)ethyl)phenyl)-2-chloro-3-methylbenzamide
(R)—N-(3-(1-((2-amino-5-chloropyridin-3-yl)oxy)ethyl)phenyl)-3-cyclopropylbenzamide
(R)—N-(3-(1-((2-amino-5-chloropyridin-3-yl)oxy)ethyl)phenyl)-3-isopropylbenzamide
(R)—N-(3-(1-((2-amino-5-chloropyridin-3-yl)oxy)ethyl)phenyl)-3-isopropoxybenzamide
(R)—N-(3-(1-((2-amino-5-chloropyridin-3-yl)oxy)ethyl)phenyl)-3-(ethylsulfonyl)benzamide
(R)—N-(3-(1-((2-amino-5-chloropyridin-3-yl)oxy)ethyl)phenyl)-2-chloro-3-methoxybenzamide
(R)—N-(3-(1-((2-amino-5-chloropyridin-3-yl)oxy)ethyl)phenyl)-3-(1-hydroxycyclopentyl)benzamide
(R)—N-(3-(1-((2-amino-5-chloropyridin-3-yl)oxy)ethyl)phenyl)-4-(methylsulfonyl)benzamide
(R)—N-(3-(1-((2-amino-5-chloropyridin-3-yl)oxy)ethyl)phenyl)-3-(1-hydroxycyclobutyl)benzamide
(R)—N-(3-(1-((2-amino-5-chloropyridin-3-yl)oxy)ethyl)phenyl)-4-methylbenzamide
(R)—N-(3-(1-((2-amino-5-chloropyridin-3-yl)oxy)ethyl)-4-chlorophenyl)-2-chloro-3-meth ylbenzamide
N-(3-((R)-1-((2-amino-5-chloropyridin-3-yl)oxy)ethyl)phenyl)-3-((2-hydroxycyclohexyl) amino)benzamide
(R)—N-(5-(1-((2-amino-5-chloropyridin-3-yl)oxy)ethyl)-2-fluorophenyl)-2-chloro-3-meth ylbenzamide
(R)—N-(3-(1-((2-amino-5-chloropyridin-3-yl)oxy)ethyl)phenyl)-3-(1-hydroxycyclohexyl)benzamide
(R)—N-(3-(1-((2-amino-5-chloropyridin-3-yl)oxy)ethyl)phenyl)-4-((4-methylpiperazin-1-yl)methyl)benzamide
(R)—N-(3-(1-((2-amino-5-chloropyridin-3-yl)oxy)ethyl)phenyl)-3-(4-methylpiperazin-1-yl)benzamide
(R)—N-(3-(1-((2-amino-5-chloropyridin-3-yl)oxy)ethyl)phenyl)-4-(4-methylpiperazin-1-yl)benzamide
(R)—N-(3-(1-((2-amino-5-chloropyridin-3-yl)oxy)ethyl)phenyl)-2-methoxy-5-(methylsulfonyl)benzamide
(R)—N-(3-(1-((2-amino-5-chloropyridin-3-yl)oxy)ethyl)phenyl)-3-((4-methylpiperazin-1-yl)methyl)benzamide
(R)—N-(3-(1-((2-amino-5-chloropyridin-3-yl)oxy)ethyl)phenyl)-3-(cyclopropylsulfonyl)benzamide
(R)—N-(3-(1-((2-amino-5-chloropyridin-3-yl)oxy)ethyl)phenyl)-3-(isopropylsulfonyl)benzamide
(R)—N-(3-(1-((2-amino-5-chloropyridin-3-yl)oxy)ethyl)phenyl)-3-(cyclopentylsulfonyl)benzamide
(R)—N-(3-(1-((2-amino-5-chloropyridin-3-yl)oxy)ethyl)phenyl)quinoline-3-carboxamide
(R)—N-(3-(1-((2-amino-5-chloropyridin-3-yl)oxy)ethyl)phenyl)isoquinoline-6-carboxamide
(R)—N-(3-(1-((2-amino-5-chloropyridin-3-yl)oxy)ethyl)phenyl)quinoline-6-carboxamide
(R)—N-(3-(1-((2-amino-5-chloropyridin-3-yl)oxy)ethyl)phenyl)-3-(pyrrolidin-1-ylsulfonyl)benzamide
(R)—N-(3-(1-((2-amino-5-chloropyridin-3-yl)oxy)ethyl)phenyl)-5-cyclopropylnicotinamide
(R)—N-(5-(1-((2-amino-5-chloropyridin-3-yl)oxy)ethyl)pyridin-3-yl)-2-chloro-3-methylbenzamide
(R)—N-(3-(1-((2-amino-5-chloropyridin-3-yl)oxy)ethyl)phenyl)-3-(1-cyanocyclopropyl)benzamide
(R)—N-(3-(1-((2-amino-5-chloropyridin-3-yl)oxy)ethyl)phenyl)-3-cyclobutylbenzamide
(R)—N-(3-(1-((2-amino-5-chloropyridin-3-yl)oxy)ethyl)phenyl)-3-(trifluoromethyl)benzamide
(R)—N-(3-(1-((2-amino-5-chloropyridin-3-yl)oxy)ethyl)phenyl)-3-(pyrrolidin-1-yl)benzamide
(R)—N-(3-(1-((2-amino-5-chloropyridin-3-yl)oxy)ethyl)phenyl)-2,3-dihydrobenzo[b]thiophene-4-carboxamide 1,1-dioxide
(R)—N-(3-(1-((2-amino-5-chloropyridin-3-yl)oxy)ethyl)phenyl)-2,3-dihydrobenzo[b]thiophene-5-carboxamide 1,1-dioxide
(R)—N-(3-(1-((2-amino-5-chloropyridin-3-yl)oxy)ethyl)phenyl)benzo[d][1,3]dioxole-5-carboxamide
(R)—N-(3-(1-((2-amino-5-chloropyridin-3-yl)oxy)ethyl)phenyl)-5-fluoropicolinamide
(R)—N-(3-(1-((2-amino-5-chloropyridin-3-yl)oxy)ethyl)phenyl)-5-methylpicolinamide
(R)—N-(3-(1-((2-amino-5-chloropyridin-3-yl)oxy)ethyl)phenyl)-4-methylpicolinamide
(R)—N-(3-(1-((2-amino-5-chloropyridin-3-yl)oxy)ethyl)phenyl)-4-(trifluoromethyl)picolinamide
(R)—N-(3-(1-((2-amino-5-chloropyridin-3-yl)oxy)ethyl)phenyl)-5-(trifluoromethyl)picolinamide
(R)—N-(3-(1-((2-amino-5-chloropyridin-3-yl)oxy)ethyl)phenyl)-6-(trifluoromethyl)picolinamide
(R)—N-(3-(1-((2-amino-5-chloropyridin-3-yl)oxy)ethyl)phenyl)-4-methyl-3-(methylsulfonyl)benzamide
(R)—N-(5-(1-((2-amino-5-chloropyridin-3-yl)oxy)ethyl)-2-methylphenyl)-3-(trifluoromethyl)benzamide
(R)—N-(3-(1-((2-amino-5-chloropyridin-3-yl)oxy)ethyl)phenyl)-3-(difluoromethyl)benzamide
(R)—N-(3-(1-((2-amino-5-chloropyridin-3-yl)oxy)ethyl)phenyl)-6-methylpicolinamide
(R)—N-(3-(1-((2-amino-5-chloropyridin-3-yl)oxy)ethyl)phenyl)-4-chloro-3-methylbenzamide
(R)—N-(3-(1-((2-amino-5-chloropyridin-3-yl)oxy)ethyl)phenyl)-4-fluoro-3-methylbenzamide
(R)—N-(3-(1-((2-amino-5-chloropyridin-3-yl)oxy)ethyl)phenyl)-3,4-dimethylbenzamide
(R)—N-(3-(1-((2-amino-5-chloropyridin-3-yl)oxy)ethyl)phenyl)-2,3-dihydro-1H-indene-5-carboxamide
(R)—N-(3-(1-((2-amino-5-chloropyridin-3-yl)oxy)ethyl)phenyl)-2,3-dihydrobenzo[b]thiophene-6-carboxamide 1,1-dioxide
(R)—N-(3-(1-((2-amino-5-chloropyridin-3-yl)oxy)ethyl)phenyl)-3-fluoro-5-methylbenzamide
(R)—N-(3-(1-((2-amino-5-chloropyridin-3-yl)oxy)ethyl)phenyl)-3-chloro-5-methylbenzamide
(R)—N-(3-(1-((2-amino-5-chloropyridin-3-yl)oxy)ethyl)phenyl)-3,5-dimethylbenzamide
(R)—N-(5-(1-((2-amino-5-chloropyridin-3-yl)oxy)ethyl)-2-methylphenyl)-3-(methylsulfonyl)benzamide
(R)—N-(3-(1-((2-amino-5-chloropyridin-3-yl)oxy)ethyl)-4-fluorophenyl)-3-(methylsulfonyl)benzamide
(R)—N-(3-(1-((2-amino-5-chloropyridin-3-yl)oxy)ethyl)-4-chlorophenyl)-3-(methylsulfonyl)benzamide
(R)—N-(6-(1-((2-amino-5-chloropyridin-3-yl)oxy)ethyl)pyridin-2-yl)-3-methylbenzamide
(R)—N-(3-(1-((2-amino-5-chloropyridin-3-yl)oxy)ethyl)-4-methylphenyl)-3-(methylsulfonyl)benzamide
(R)—N-(3-(1-((2-amino-5-chloropyridin-3-yl)oxy)ethyl)-2-methylphenyl)-3-(methylsulfonyl)benzamide
(R)—N-(4-(1-((2-amino-5-chloropyridin-3-yl)oxy)ethyl)pyridin-2-yl)-3-methylbenzamide
(R)—N-(5-(1-((2-amino-5-chloropyridin-3-yl)oxy)ethyl)-2-chlorophenyl)-3-(methylsulfonyl)benzamide
(R)—N-(5-(1-((2-amino-5-chloropyridin-3-yl)oxy)ethyl)-2-fluorophenyl)-3-(methylsulfonyl)benzamide (R)—N-(3-(1-((2-amino-5-chloropyridin-3-yl)oxy)ethyl)phenyl)-3-(methylsulfonyl)-4-(trifluoromethyl)benzamide
(R)—N-(3-(1-((2-amino-5-chloropyridin-3-yl)oxy)ethyl)phenyl)benzo[b]thiophene-5-carb oxamide 1,1-dioxide
(R)—N-(3-(1-((2-amino-5-chloropyridin-3-yl)oxy)ethyl)phenyl)benzo[b]thiophene-6-carb oxamide 1,1-dioxide
(R)—N-(3-(1-((2-amino-5-chloropyridin-3-yl)oxy)ethyl)phenyl)-3-(methylsulfonyl)-5-(trifluoromethyl)benzamide
(R)—N-(3-(1-((2-amino-5-chloropyridin-3-yl)oxy)ethyl)phenyl)-3,4-dimethyl-5-(methylsulfonyl)benzamide
(R)—N-(3-(1-((2-amino-5-chloropyridin-3-yl)oxy)ethyl)phenyl)-1,5-dimethyl-1H-pyrazole-3-carboxamide
(R)—N-(3-(1-((2-amino-5-chloropyridin-3-yl)oxy)ethyl)phenyl)-5-methylthiazole-2-carboxamide
(R)—N-(3-(1-((2-amino-5-chloropyridin-3-yl)oxy)ethyl)phenyl)-1-(tert-butyl)-1H-pyrazole-4-carboxamide
(R)—N-(3-(1-((2-amino-5-chloropyridin-3-yl)oxy)ethyl)phenyl)-1-isopropyl-1H-pyrazole-4-carboxamide
(R)—N-(3-(1-((2-amino-5-chloropyridin-3-yl)oxy)ethyl)phenyl)-1-methyl-1H-indazole-6-carboxamide
(R)—N-(3-(1-((2-amino-5-chloropyridin-3-yl)oxy)ethyl)phenyl)benzofuran-6-carboxamide
(R)—N-(3-(1-((2-amino-5-chloropyridin-3-yl)oxy)ethyl)phenyl)-1-methyl-1H-indole-6-carboxamide
(R)—N-(3-(1-((2-amino-5-chloropyridin-3-yl)oxy)ethyl)phenyl)-5-(tert-butyl)isoxazole-3-carboxamide
(R)—N-(3-(1-((2-amino-5-chloropyridin-3-yl)oxy)ethyl)phenyl)-1-methyl-2-oxo-1,2,3,4-tetrahydroquinoline-7-carboxamide
(R)—N-(3-(1-((2-amino-5-chloropyridin-3-yl)oxy)ethyl)phenyl)-1-methyl-1,2,3,4-tetrahydroquinoline-7-carboxamide
(R)—N-(3-(1-((2-amino-5-chloropyridin-3-yl)oxy)ethyl)phenyl)-1-methylindoline-6-carboxamide
(R)—N-(3-(1-((2-amino-5-chloropyridin-3-yl)oxy)ethyl)phenyl)-1-methyl-2-oxoindoline-6-carboxamide
(R)—N-(3-(1-((2-amino-5-chloropyridin-3-yl)oxy)ethyl)phenyl)-1,3-dihydroisobenzofuran-5-carboxamide
(R)—N-(3-(1-((2-amino-5-(1-methyl-1H-pyrazol-4-yl)pyridin-3-yl)oxy)ethyl)phenyl)-3-(methylsulfonyl)benzamide
(R)—N-(3-(1-((2-amino-5-(1-methyl-1H-pyrazol-4-yl)pyridin-3-yl)oxy)ethyl)phenyl)-3-(trifluoromethyl)benzamide
(R)—N-(3-(1-((2-amino-5-(1-methyl-1H-pyrazol-4-yl)pyridin-3-yl)oxy)ethyl)phenyl)-3,4-dimethylbenzamide
(R)—N-(3-(1-((2-amino-5-(1-methyl-1H-pyrazol-4-yl)pyridin-3-yl)oxy)ethyl)phenyl)-3,5-dimethylbenzamide
(R)—N-(3-(1-((2-amino-5-(1-methyl-1H-pyrazol-4-yl)pyridin-3-yl)oxy)ethyl)phenyl)-4-m ethyl-3-(methylsulfonyl)benzamide
(R)—N-(3-(1-((2-amino-5-(1-methyl-1H-pyrazol-4-yl)pyridin-3-yl)oxy)ethyl)phenyl)-2,3-dihydrobenzo[b]thiophene-6-carboxamide 1,1-dioxide
(R)—N-(3-(1-((2-amino-5-(1-methyl-1H-pyrazol-4-yl)pyridin-3-yl)oxy)ethyl)phenyl)-3-cyclopropylbenzamide
(R)—N-(3-(1-((2-amino-5-(1-methyl-1H-pyrazol-4-yl)pyridin-3-yl)oxy)ethyl)phenyl)-3-(methylsulfonyl)-4-(trifluoromethyl)benzamide
(R)—N-(3-(1-((2-amino-5-(1-methyl-1H-pyrazol-4-yl)pyridin-3-yl)oxy)ethyl)phenyl)-3-(methylsulfonyl)-5-(trifluoromethyl)benzamide
(R)—N-(3-(1-((2-amino-5-(1-methyl-1H-pyrazol-4-yl)pyridin-3-yl)oxy)ethyl)phenyl)-3,4-dimethyl-5-(methylsulfonyl)benzamide
(R)—N-(3-(1-((2-amino-5-(1-methyl-1H-pyrazol-4-yl)pyridin-3-yl)oxy)ethyl)phenyl)-3-(dimethylamino)benzamide
(R)—N-(3-(1-((2-amino-5-(1-methyl-1H-pyrazol-4-yl)pyridin-3-yl)oxy)ethyl)phenyl)-3-(dimethylamino)-4-methylbenzamide
(R)—N-(3-(1-((2-amino-5-(1-methyl-1H-pyrazol-4-yl)pyridin-3-yl)oxy)ethyl)phenyl)-3-(methylthio)benzamide
(R)—N-(3-(1-((2-amino-5-(1-methyl-1H-pyrazol-4-yl)pyridin-3-yl)oxy)ethyl)phenyl)-4-(methylthio)benzamide
(R)—N-(3-(1-((2-amino-5-(1-methyl-1H-pyrazol-4-yl)pyridin-3-yl)oxy)ethyl)phenyl)-4-methyl-3-(methylthio)benzamide
(R)—N-(3-(1-((2-amino-5-(1-methyl-1H-pyrazol-4-yl)pyridin-3-yl)oxy)ethyl)phenyl)-2',3'-dihydrospiro[cyclopropane-1,1'-indene]-6'-carboxamide
(R)—N-(3-(1-((2-amino-5-(1-methyl-1H-pyrazol-4-yl)pyridin-3-yl)oxy)ethyl)phenyl)-1-methylindoline-6-carboxamide
(R)—N-(3-(1-((2-amino-5-(1-methyl-1H-pyrazol-4-yl)pyridin-3-yl)oxy)ethyl)phenyl)-4-chloro-3-(dimethylamino)benzamide
methyl (R)-3-((3-(1-((2-amino-5-(1-methyl-1H-pyrazol-4-yl)pyridin-3-yl)oxy)ethyl)phenyl)carbamoyl)benzoate
(R)—N-(3-(1-((2-amino-5-(1-methyl-1H-pyrazol-4-yl)pyridin-3-yl)oxy)ethyl)phenyl)-3-isopropylbenzamide
(R)—N-(3-(1-((2-amino-5-(1-methyl-1H-pyrazol-4-yl)pyridin-3-yl)oxy)ethyl)phenyl)-2,3-dihydro-1H-indene-5-carboxamide
(R)—N-(3-(1-((2-amino-5-(1-methyl-1H-pyrazol-4-yl)pyridin-3-yl)oxy)ethyl)phenyl)-3-ethylbenzamide
(R)—N-(3-(1-((2-amino-5-(1-methyl-1H-pyrazol-4-yl)pyridin-3-yl)oxy)ethyl)phenyl)-5-isopropylnicotinamide
(R)—N-(3-(1-((2-amino-5-(1-methyl-1H-pyrazol-4-yl)pyridin-3-yl)oxy)ethyl)phenyl)-1-methyl-1H-indole-6-carboxamide
(R)—N-(3-(1-((2-amino-5-(1-methyl-1H-pyrazol-4-yl)pyridin-3-yl)oxy)ethyl)phenyl)benzo[b]thiophene-6-carboxamide
(R)—N-(3-(1-((2-amino-5-(1-methyl-1H-pyrazol-4-yl)pyridin-3-yl)oxy)ethyl)phenyl)-3,3-dimethyl-1,3-dihydroisobenzofuran-5-carboxamide
(R)—N-(3-(1-((2-amino-5-(1-methyl-1H-pyrazol-4-yl)pyridin-3-yl)oxy)ethyl)phenyl)-2H-spiro[benzofuran-3,1'-cyclopropane]-5-carboxamide
(R)—N-(3-(1-((2-amino-5-(1-methyl-H-pyrazol-4-yl)pyridin-3-yl)oxy)ethyl)phenyl)-2,3-dihydrobenzofuran-5-carboxamide
(R)—N-(3-(1-((6-amino-[3,3'-bipyridin]-5-yl)oxy)ethyl)phenyl)-3-(methylsulfonyl)benzamide
(R)—N-(3-(1-((6-amino-[3,3'-bipyridin]-5-yl)oxy)ethyl)phenyl)-3-cyclopropylbenzamide
(R)—N-(3-(1-((6-amino-[3,3'-bipyridin]-5-yl)oxy)ethyl)phenyl)-3-(trifluoromethyl)benzamide
(R)—N-(3-(1-((6-amino-[3,3'-bipyridin]-5-yl)oxy)ethyl)phenyl)-3-methylbenzamide
(R)—N-(3-(1-((6-amino-[3,3'-bipyridin]-5-yl)oxy)ethyl)phenyl)-3,4-dimethylbenzamide
(R)—N-(3-(1-((6-amino-[3,3'-bipyridin]-5-yl)oxy)ethyl)phenyl)-3,5-dimethylbenzamide
(R)—N-(3-(1-((6-amino-[3,3'-bipyridin]-5-yl)oxy)ethyl)phenyl)-3-(dimethylamino)benzamide
(R)—N-(3-(1-((6-amino-[3,3'-bipyridin]-5-yl)oxy)ethyl)phenyl)-3-(dimethylamino)-4-methylbenzamide
(R)—N-(3-(1-((6-amino-[3,3'-bipyridin]-5-yl)oxy)ethyl)phenyl)-3-(methylthio)benzamide
(R)—N-(3-(1-((6-amino-[3,3'-bipyridin]-5-yl)oxy)ethyl)phenyl)-1-methylindoline-6-carboxamide (R)—N-(3-(1-((2-amino-5-(1-(piperidin-4-yl)-1H-pyrazol-4-yl)pyridin-3-yl)oxy)ethyl)phenyl)-3-cyclopropylbenzamide
(R)—N-(3-(1-((2-amino-5-(1-cyclopropyl-1H-pyrazol-4-yl)pyridin-3-yl)oxy)ethyl)phenyl)-3-(dimethyl amino)benzamide
(R)—N-(3-(1-((2-amino-5-(1-ethyl-1H-pyrazol-4-yl)pyridin-3-yl)oxy)ethyl)phenyl)-3-(dimethylamino)benzamide
(R)—N-(3-(1-((2-amino-5-(1-methylpiperidin-4-yl)pyridin-3-yl)oxy)ethyl)phenyl)-3-(dimethylamino)benzamide
(R)—N-(3-(1-((2-amino-5-(4-hydroxy-3-methoxyphenyl)pyridin-3-yl)oxy)ethyl)phenyl)-3-(dimethylamino)benzamide
(R)—N-(3-(1-((6-amino-6'-(4-methylpiperazin-1-yl)-[3,3'-bipyridin]-5-yl)oxy)ethyl)phenyl)-3-(dimethylamino)benzamide
(R)—N-(3-(1-((6-amino-[3,4'-bipyridin]-5-yl)oxy)ethyl)phenyl)-3-(dimethylamino)benzamide
N-(3-(1-((2-amino-5-chloropyridin-3-yl)oxy)ethyl)phenyl)-3-methylbenzamide
N-(3-(((5-chloro-2-(methylamino)pyridin-3-yl)oxy)methyl)phenyl)-3-methylbenzamide
N-(3-(((2-aminopyridin-3-yl)oxy)methyl)phenyl)-3-methylbenzamide
5-(((2-amino-5-chloropyridin-3-yl)oxy)methyl)-N-((6-(trifluoromethyl)pyridin-3-yl)methyl)pyridin-2-amine
5-chloro-3-((3-methoxy-4-((4-methoxybenzyl)oxy)benzyl)oxy)pyridin-2-amine
5-chloro-3-(3-methoxy-4-((4-methoxybenzyl)oxy)phenoxy)pyridin-2-amine
N-(3-(((3-amino-6-chloropyrazin-2-yl)oxy)methyl)phenyl)-3-methylbenzamide
5-chloro-3-((3-methoxy-4-((4-methoxybenzyl)oxy)benzyl)oxy)pyrazin-2-amine
5-chloro-3-(3-methoxy-4-((4-methoxybenzyl)oxy)phenoxy)pyrazin-2-amine
5-chloro-3-((6-((4-methoxybenzyl)oxy)pyridin-3-yl)methoxy)pyridin-2-amine
(E)-5-chloro-3-(3-methoxy-4-((4-methoxybenzyl)oxy)styryl)pyridin-2-amine
(E)-N-(3-(2-(2-amino-5-chloropyridin-3-yl)vinyl)phenyl)-3-methylbenzamide
N-(3-(2-(2-amino-5-chloropyridin-3-yl)cyclopropyl)phenyl)-3-methylbenzamide
N-(3-(2-((2-amino-5-chloropyridin-3-yl)oxy)propan-2-yl)phenyl)-3-methylbenzamide
N-(3-(2-((2-amino-5-chloropyridin-3-yl)oxy)propan-2-yl)phenyl)-2-chloro-5-methylbenzamide
N-(3-(2-((2-amino-5-chloropyridin-3-yl)oxy)propan)-2-yl)phenyl)-2,5-dichlorobenzamide
N-(3-(2-((2-amino-5-chloropyridin-3-yl)oxy)propan-2-yl)phenyl)-3-methoxybenzamide
N-(3-(2-((2-amino-5-chloropyridin-3-yl)oxy)propan-2-yl)phenyl)-2-chloro-3-methylbenzamide
N-(3-(2-((2-amino-5-chloropyridin-3-yl)oxy)propan-2-yl)phenyl)-2,5-dichlorobenzamide
N-(3-(1-((2-amino-5-chloropyridin-3-yl)oxy)cyclopropyl)phenyl)-3-methylbenzamide
N-(3-(1-((2-amino-5-chloropyridin-3-yl)oxy)cyclobutyl)phenyl)-3-methylbenzamide
N-(3-(1-((2-amino-5-chloropyridin-3-yl)oxy)cyclopentyl)phenyl)-3-methylbenzamide
N-(3-(1-((2-amino-5-chloropyridin-3-yl)oxy)cyclohexyl)phenyl)-3-methylbenzamide
5-chloro-3-((5-methoxy-6-((4-methoxybenzyl)oxy)pyridin-3-yl)oxy)pyridin-2-amine
5-((2-amino-5-chloropyridin-3-yl)oxy)-N-((6-(trifluoromethyl)pyridin-3-yl)methyl)pyridin-2-amine
4-((4-((2-amino-5-chloropyridin-3-yl)oxy)-2-methoxyphenoxy)methyl)benzonitrile
5-chloro-3-(3-methoxy-4-((4-(trifluoromethyl)benzyl)oxy)phenoxy)pyridin-2-amine
4-(((5-((2-amino-5-chloropyridin-3-yl)oxy)-3-methoxypyridin-2-yl)oxy)methyl)benzonitrile
5-chloro-3-((6-((4-chlorobenzyl)oxy)-5-methoxypyridin-3-yl)oxy)pyridin-2-amine
N-(4-((2-amino-5-chloropyridin-3-yl)oxy)phenyl)-3-methoxybenzamide
N-(4-((2-amino-5-chloropyridin-3-yl)oxy)phenyl)-4-methoxybenzamide
N-(4-((2-amino-5-chloropyridin-3-yl)oxy)phenyl)-4-cyanobenzamide
N-(3-((2-amino-5-chloropyridin-3-yl)oxy)phenyl)-3-methylbenzamide
N-(3-((2-amino-5-chloropyridin-3-yl)oxy)phenyl)-3-methoxybenzamide
N-(3-((2-amino-5-chloropyridin-3-yl)oxy)phenyl)-3-chlorobenzamide
N-(3-((2-amino-5-chloropyridin-3-yl)oxy)phenyl)-3-(trifluoromethoxy)benzamide
N-(3-((2-amino-5-chloropyridin-3-yl)oxy)phenyl)-4-methoxybenzamide
N-(3-((2-amino-5-chloropyridin-3-yl)oxy)phenyl)-3-(methylsulfonyl)benzamide
N-(3-((2-amino-5-chloropyridin-3-yl)oxy)phenyl)-3-(1-hydroxycyclopentyl)benzamide
N-(3-((2-amino-5-chloropyridin-3-yl)oxy)phenyl)-3-cyclopropylbenzamide
N-(3-((2-amino-5-chloropyridin-3-yl)oxy)phenyl)-3-(1-cyanocyclopropyl)benzamide
N-(3-((2-amino-5-chloropyridin-3-yl)oxy)phenyl)-3-(4-methylpiperazin-1-yl)benzamide
N-(5-((2-amino-5-chloropyridin-3-yl)oxy)-2-fluorophenyl)-3-methoxybenzamide
N-(5-((2-amino-5-chloropyridin-3-yl)oxy)-2-chlorophenyl)-3-methoxybenzamide
N-(5-((2-amino-5-chloropyridin-3-yl)oxy)-2-methylphenyl)-3-methoxybenzamide
N-(5-(1-((2-amino-5-chloropyridin-3-yl)oxy)ethyl)-2-fluorophenyl)-3-methoxybenzamide
N-(3-(((2-amino-5-chloropyridin-3-yl)oxy)methyl)-2-fluorophenyl)-3-methoxybenzamide
N-(3-(((2-amino-5-chloropyridin-3-yl)oxy)methyl)-4-fluorophenyl)-3-methoxybenzamide
(R)—N-(3-(1-((5-chloropyridin-3-yl)oxy)ethyl)phenyl)-3-methylbenzamide
(R)—N-(3-(1-((6-chloropyrazin-2-yl)oxy)ethyl)phenyl)-3-(trifluoromethyl)benzamide
(R)-1-(3-(1-((2-amino-5-chloropyridin-3-yl)oxy)ethyl)phenyl)-3-(p-tolyl)urea
(R)-1-(3-(1-((2-amino-5-chloropyridin-3-yl)oxy)ethyl)phenyl)-3-(m-tolyl)urea
1-(3-((2-amino-5-chloropyridin-3-yl)oxy)phenyl)-3-(4-chloro-3-(trifluoromethyl)phenyl) urea
1-(3-((2-amino-5-chloropyridin-3-yl)oxy)phenyl)-3-(m-tolyl)urea
1-(3-((2-amino-5-chloropyridin-3-yl)oxy)phenyl)-3-(p-tolyl)urea
1-(3-((2-amino-5-chloropyridin-3-yl)oxy)phenyl)-3-(4-(methylsulfonyl)phenyl)urea
1-(4-((2-amino-5-chloropyridin-3-yl)oxy)phenyl)-3-(m-tolyl)urea 1-(4-((2-amino-5-chloropyridin-3-yl)oxy)phenyl)-3-(p-tolyl)urea
1-(4-((2-amino-5-chloropyridin-3-yl)oxy)phenyl)-3-(4-chloro-3-(trifluoromethyl)phenyl) urea
1-(4-((2-amino-5-chloropyridin-3-yl)oxy)-2-methylphenyl)-3-(4-chloro-3-(trifluoromethyl)phenyl)urea
1-(4-((2-amino-5-chloropyridin-3-yl)oxy)-3-methylphenyl)-3-(4-chloro-3-(trifluoromethyl)phenyl)urea
1-(4-((2-amino-5-chloropyridin-3-yl)oxy)-3-fluorophenyl)-3-(4-chloro-3-(trifluoromethyl)phenyl)urea
1-(4-((2-amino-5-chloropyridin-3-yl)oxy)-2-fluorophenyl)-3-(4-chloro-3-(trifluoromethyl)phenyl)urea
1-(5-((2-amino-5-chloropyridin-3-yl)oxy)-2-methylphenyl)-3-(p-tolyl)urea
1-(5-((2-amino-5-chloropyridin-3-yl)oxy)-2-chlorophenyl)-3-(p-tolyl)urea
1-(3-((2-amino-5-chloropyridin-3-yl)oxy)phenyl)-3-(4-(dimethylamino)phenyl)urea
1-(3-((2-amino-5-chloropyridin-3-yl)oxy)phenyl)-3-(4-methoxyphenyl)urea
1-(3-((2-amino-5-chloropyridin-3-yl)oxy)phenyl)-3-(2,3-dihydrobenzo[b]thiophen-5-yl)urea
1-(3-((2-amino-5-chloropyridin-3-yl)oxy)phenyl)-3-(benzo[b]thiophen-5-yl)urea
1-(3-((2-amino-5-chloropyridin-3-yl)oxy)phenyl)-3-(1-(tert-butyl)-1H-pyrazol-4-yl)urea
1-(3-((2-amino-5-(1-methyl-1H-pyrazol-4-yl)pyridin-3-yl)oxy)phenyl)-3-(4-chloro-3-(trifluoromethyl)phenyl)urea
1-(3-((2-amino-5-(1-methyl-1H-pyrazol-4-yl)pyridin-3-yl)oxy)phenyl)-3-(p-tolyl)urea
1-(3-((2-amino-5-(1-methyl-1H-pyrazol-4-yl)pyridin-3-yl)oxy)phenyl)-3-(4-(methylsulfonyl)phenyl)urea
1-(4-((2-amino-5-(1-methyl-1H-pyrazol-4-yl)pyridin-3-yl)oxy)phenyl)-3-(4-chloro-3-(trifluoromethyl)phenyl)urea
1-(4-((2-amino-5-(1-methyl-1H-pyrazol-4-yl)pyridin-3-yl)oxy)-2-fluorophenyl)-3-(4-chloro-3-(trifluoromethyl)phenyl)urea
1-(3-((6-amino-[3,3'-bipyridin]-5-yl)oxy)phenyl)-3-(4-chloro-3-(trifluoromethyl)phenyl)u rea
1-(3-((6-amino-[3,3'-bipyridin]-5-yl)oxy)phenyl)-3-(p-tolyl)urea
1-(3-((6-amino-[3,3'-bipyridin]-5-yl)oxy)phenyl)-3-(4-(methylsulfonyl)phenyl)urea
1-(4-((6-amino-[3,3'-bipyridin]-5-yl)oxy)phenyl)-3-(4-chloro-3-(trifluoromethyl)phenyl)u rea
(R)—N-(3-(1-((2-amino-5-(1-methyl-1H-pyrazol-5-yl)pyridin-3-yl)oxy)ethyl)phenyl)-4-(methylthio)benzamide
(R)—N-(3-(1-((2-amino-5-(1-cyclopropyl-1H-pyrazol-4-yl)pyridin-3-yl)oxy)ethyl)phenyl)-4-(methylthio)benzamide
(R)—N-(3-(1-((2-amino-5-(1H-pyrazol-4-yl)pyridin-3-yl)oxy)ethyl)phenyl)-4-(methylthio)benzamide
(R)—N-(3-(1-((2-amino-5-(1-methyl-1H-pyrazol-4-yl)pyridin-3-yl)oxy)ethyl)phenyl)-3-chloro-4-(methylthio)benzamide
(R)—N-(3-(1-((2-amino-5-(1-methyl-1H-pyrazol-4-yl)pyridin-3-yl)oxy)ethyl)phenyl)-3-fluoro-4-(methylthio)benzamide
(R)—N-(3-(1-((2-amino-5-(1-methyl-1H-pyrazol-4-yl)pyridin-3-yl)oxy)ethyl)phenyl)-3-cyano-4-(methylthio)benzamide
(R)—N-(3-(1-((2-amino-5-(1,3-dimethyl-1H-pyrazol-4-yl)pyridin-3-yl)oxy)ethyl)phenyl)-4-(methylthio)benzamide
(R)—N-(3-(1-((2-amino-5-(1-(2-(dimethylamino)-2-oxoethyl)-1H-pyrazol-4-yl)pyridin-3-yl)oxy)ethyl)phenyl)-4-(methylthio)benzamide
(R)—N-(3-(1-((2-amino-5-(3-methyl-1H-pyrazol-4-yl)pyridin-3-yl)oxy)ethyl)phenyl)-4-(methylthio)benzamide
(R)—N1-(3-(1-((2-amino-5-(1-methyl-1H-pyrazol-4-yl)pyridin-3-yl)oxy)ethyl)phenyl)-4-(methylthio)isophthalamide
N-(3-((R)-1-((2-amino-5-(1-methyl-1H-pyrazol-4-yl)pyridin-3-yl)oxy)ethyl)phenyl)-3-(methylsulfinyl)benzamide
N-(3-((S)-1-((2-amino-5-(1-methyl-1H-pyrazol-4-yl)pyridin-3-yl)oxy)ethyl)phenyl)-3-(methylsulfinyl)benzamide
(S)—N-(3-(1-((2-amino-5-(1-methyl-1H-pyrazol-4-yl)pyridin-3-yl)oxy)ethyl)phenyl)-3-(methylsulfonyl)benzamide
(S)—N-(3-(1-((2-amino-5-(1-methyl-1H-pyrazol-4-yl)pyridin-3-yl)oxy)ethyl)phenyl)-3-(dimethylamino)benzamide
(S)—N-(3-(1-((2-amino-5-(1-methyl-1H-pyrazol-4-yl)pyridin-3-yl)oxy)ethyl)phenyl)-3-(dimethylamino)-4-methylbenzamide
(S)—N-(3-(1-((2-amino-5-(1-methyl-1H-pyrazol-4-yl)pyridin-3-yl)oxy)ethyl)phenyl)-3-(methylthio)benzamide
(S)—N-(3-(1-((2-amino-5-(1-methyl-1H-pyrazol-4-yl)pyridin-3-yl)oxy)ethyl)phenyl)-4-methyl-3-(methylthio)benzamide The pharmaceutical composition of the present invention contains at least one effective therapeutic amount of a compound of the above formula (I) and at least one pharmaceutically acceptable excipient, adjuvant or carrier.

The pharmaceutical composition of the invention can be applied to pharmaceutical manufacture.

The method of the present invention for treating abnormal cell growth in a mammal comprising administering to the subject a therapeutically effective amount of a compound of the above formula (I) or a pharmaceutical composition thereof, wherein the abnormal cell growth is preferably tumor.

The present invention is for use in the treatment and prevention of CSF-1R kinase mediated melanoma, ovarian cancer, uterine cancer, breast cancer, colon cancer, gastric cancer, liver cancer and non-small cell lung cancer, comprising administering a therapeutically effective amount to a subject Compound of formula (I) or a pharmaceutical composition thereof.

The compounds and pharmaceutical compositions of the present invention are useful for the preparation of a medicament for treating abnormal cell growth in a mammal, wherein abnormal cell growth is preferably tumor.

The compounds and pharmaceutical compositions of the invention are useful in the manufacture of a medicament for the treatment and prevention of CSF-1R kinase mediated tumor.

The compounds and pharmaceutical compositions of the invention are administered in combination with chemotherapeutic agents, radiation, and/or cancer immunotherapy.

Definitions

Unless otherwise stated, the following terms used in the specification and claims have the meanings discussed below. Variables defined in this section, such as A, R, X, Z and the like, are for reference within this section only, and are not meant to have the save meaning as may be used outside of this definitions section. Further, many of the groups defined herein can be optionally substituted. The listing in this definitions section of typical substituents is exemplary and is not intended to limit the substituents defined elsewhere within this specification and claims.

"$C_m$-$C_n$" refers to the carbon atoms contained in m-n.

"Alkyl" refers to a saturated aliphatic hydrocarbon radical or linker including straight chain and branched chain groups of 1 to 20 carbon atoms, preferably 1 to 12 carbon atoms, more preferably 1 to 8 carbon atoms, or 1 to 6 carbon atoms, or 1 to 4 carbon atoms. "Lower alkyl" refers specifically to an alkyl group with 1 to 4 carbon atoms. Examples of alkyl groups include —$(CH_2)_3$—, methyl, ethyl, propyl, 2-propyl, n-butyl, iso-butyl, tert-butyl, pentyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —$NR^xR^y$, where $R^x$ and $R^y$ are independently selected from the group consisting of hydrogen, alkyl, cycloalkyl, aryl, carbonyl, acetyl, sulfonyl, trifluoromethanesulfonyl and, combined, a five- or six-member heteroalicyclic ring.

"heteroalkyl" include optionally substituted alkyl radicals in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule. Examples include, but are not limited to, —$CH_2$—O—$CH_3$, —$CH_2$—$CH_2$—O—$CH_3$, —$OCH_2$—, —$CH_2$—NH—$CH_3$, —$CH_2$—CH—NH—$CH_3$, —$CH_2$—N$(CH_3)$—$CH_3$, —$NCH_2CH_2$—, —$CH_2$—$CH_2$—NH—$CH_3$, —$CH_2$—CH—N$(CH_3)$—$CH_3$, —$CH_2$—S—CH—$CH_3$, —$CH_2$—$CH_2$—S(O)—$CH_3$, —$CH_2$—CH—S$(O)_2$—$CH_3$. In addition, up to two heteroatoms may be consecutive, such as, by way of example, —CH—NH—$OCH_3$.

"Cycloalkyl" refers to a 3 to 8 member all-carbon monocyclic ring, an all-carbon 5-member/6-member or 6-member/6-member fused bicyclic ring, or a multicyclic fused ring (a "fused" ring system means that each ring in the system shares at least an adjacent carbon atom with each other ring in the system) group wherein one or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. Typical substituent groups include alkyl, aryl, heteroaryl, heteroalicyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, Camido, N-amido, nitro, amino and —$NR^xR^y$, with $R^x$ and $R^y$ as defined above. Illustrative examples of cycloalkyl are derived from, but not limited to, the following:

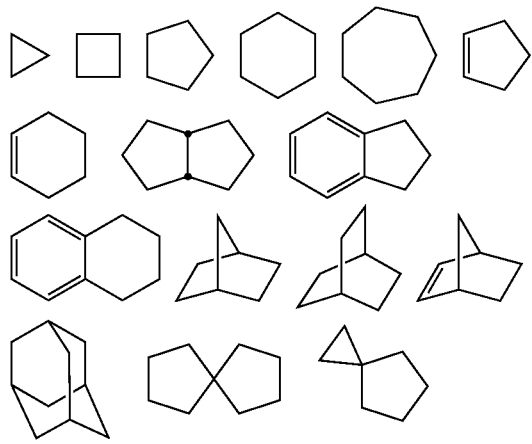

-continued

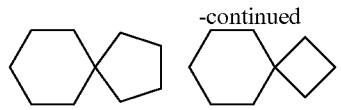

"Cycloalkylalkyl" or "Alkylcycloalkyl" means an alkyl radical, as defined herein, substituted with a cycloalkyl group. Non-limiting cycloalkylalkyl or alkylcycloalkyl groups include cyclopropylmethyl, cyclobutylmethyl, cyclopentylmethyl, cyclohexylmethyl, methylcyclobutyl and the like.

"Alkenyl" refers to an alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like.

"Aryl" refers to an all-carbon monocyclic or fused-ring polycyclic groups of 6 to 12 carbon atoms having a completely conjugated pi-electron system. Examples, without limitation, of aryl groups are phenyl, naphthalenyl and anthracenyl. The aryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, Ocarbamyl, N-carbamyl, O-thiocarbamyl, N-thiocarbamyl, C-amido, N-amido, sulfinyl, sulfonyl, amino and —$NR^xR^y$, with $R^x$ and $R^y$ as defined above.

"Heteroaryl" refers to a monocyclic or fused ring group of 5 to 12 ring atoms containing one, two, three or four ring heteroatoms selected from N, O. and S, the remaining ring atoms being C, and, in addition, having a completely conjugated π-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, tetrazole, triazine, and carbazole. The heteroaryl group may be substituted or unsubstituted. Typical substituents include alkyl, cycloalkyl, halo, trihalomethyl, hydroxy, alkoxy, aryloxy, mercapto, alkylthio, arylthio, cyano, nitro, carbonyl, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino and —$NR^xR^y$ with $R^x$ and $R^y$ as defined above.

A pharmaceutically acceptable heteroaryl is one that is sufficiently stable to be attached to a compound of the invention, formulated into a pharmaceutical composition and subsequently administered to a patient in need thereof.

Examples of typical monocyclic heteroaryl groups include, but are not limited to:

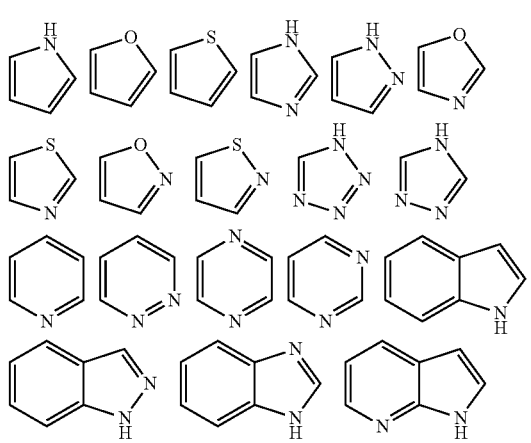

"Heteroalicyclic" or "heterocycle" refers to a monocyclic, fused ring group or spiro having in the ring(s) of 3 to 12 ring atoms, in which one or two ring atoms are heteroatoms selected from N, O, and S(O)$_n$ (wherein is 0, 1 or 2), the remaining ring atoms being C. The rings may also have one or more double bonds. However, the rings do not have a completely conjugated π-electron system. Examples of suitable saturated heteroalicyclic groups include, but are not limited to:

The heterocycle group is optionally substituted with one or two substituents independently selected from halo, lower alkyl, lower alkyl substituted with carboxy, ester hydroxy, or mono or dialkylamino.

"Hydroxy" refers to an —OH group.

"Alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like. The alkyl or cycloalkyl group may be substituted or unsubstituted, and typical substituents include a halogen group and the like. Representative examples include, but are not limited to, trifluoromethoxy, difluoromethoxy, and the like.

"Aryloxy" refers to an —O-aryl or an —O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

"Mercapto" refers to an —SH group.

"Alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

"Arylthio" refers to an —S-aryl or an —S-heteroaryl group, as defined herein. Representative examples include, but are not limited to, phenylthio, pyridinylthio, furanylthio, thienylthio, pyrimidinylthio, and the like and derivatives thereof.

"Acyl" or "carbonyl" refers to a —C(O)R" group, where R" is selected from the group consisting of hydrogen, lower alkyl, trihalomethyl, unsubstituted cycloalkyl, aryl optionally substituted with one or more, preferably one, two, or three substituents selected from the group consisting of lower alkyl, trihalomethyl, lower alkoxy, halo and —NR$^x$R$^y$ groups, heteroaryl (bonded through a ring carbon) optionally substituted with one or more, preferably one, two, or three substitutents selected from the group consisting of lower alkyl, trihaloalkyl, lower alkoxy, halo and —NR$^x$R$^y$ groups and heteroalicyclic (bonded through a ring carbon) optionally substituted with one or more, preferably one, two, or three substituents selected from the group consisting of lower alkyl, trihaloalkyl, lower alkoxy, halo and —NR$^x$R$^y$ groups. Representative acyl groups include, but are not limited to, acetyl, trifluoroacetyl, benzoyl, and the like.

"Aldehyde" refers to an acyl group in which R" is hydrogen.

"Thioacyl" or "thiocarbonyl" refers to a —C(S)R" group, with R" as defined above.

A "thiocarbonyl" group refers to a —C(S)R" group, with R" as defined above.

A "C-carboxy" group refers to a —C(O)OR" group, with R" as defined above.

An "O-carboxy" group refers to a —OC(O)R" group, with R" as defined above.

"Ester" refers to a —C(O)OR" group with R" as defined herein except that R" cannot be hydrogen.

"Acetyl" group refers to a —C(O)CH$_3$ group.

"Halo" group refers to fluorine, chlorine, bromine or iodine, preferably fluorine or chlorine.

"Trihalomethyl" group refers to a methyl group having three halo substituents, such as a trifluoromethyl group.

"Cyano" refers to a —C≡N group.

A "sulfinyl" group refers to a —S(O)R" group wherein, in addition to being as defined above, R" may also be a hydroxy group.

A "sulfonyl" group refers to a —S(O)$_2$R" group wherein, in addition to being as defined above, R" may also be a hydroxy group.

A "Phosphonoyl" group refers to a —P(O)R$_x$R$_y$, group, wherein R$^x$ and R$^y$ is selected from alkyl or alkoxy.

"S-sulfonamido" refers to a —S(O)$_2$NR$^x$R$^y$ group, with R$^x$ and R$^y$ as defined above.

"N-sulfonamido" refers to a —NR$^x$S(O)$_2$R$^y$ group, with R$^x$ and R$^y$ as defined above.

"O-carbamyl" group refers to a —OC(O)NR$^x$R$^y$ group with R$^x$ and R$^y$ as defined above.

"N-carbamyl" refers to an R$_y$OC(O)NR$_x$— group, with R$^x$ and R$^y$ as defined above.

"O-thiocarbamyl" refers to a —OC(S)NR$^x$R$^y$ group with R$^x$ and R$^y$ as defined above.

"N-thiocarbamyl" refers to a R$^y$OC(S)NR$^x$— group, with R$^y$ and R$^x$ as defined above.

"Amino" refers to an —NR$^x$R$^y$ group, wherein R$^x$ and R$^y$ are both hydrogen.

"C-amido" refers to a —C(O)NR$^x$R$^y$ group with R$^x$ and R$^y$ as defined above.

"N-amido" refers to a $R^xC(O)NR^y$ group, with $R^x$ and $R^y$ as defined above.

"-amido-" refers to a —C(O)NR$^y$— group, with $R^x$ and $R_y$ as defined above.

"Nitro" refers to a —NO$_2$ group.

"imine" refers to a —N=C— group.

"Haloalkyl" means an alkyl, preferably lower alkyl, that is substituted with one or more same or different halo atoms, e.g., —CH$_2$Cl, —CF$_3$, —CH$_2$CF$_3$, —CH$_2$CCl$_3$, and the like.

"Hydroxyalkyl" means an alkyl, preferably lower alkyl, that is substituted with one, two, or three hydroxy groups; e.g., hydroxymethyl, 1 or 2-hydroxyethyl. 1,2-, 1,3-, or 2,3-dihydroxypropyl, and the like.

"Aralkyl" means alkyl, preferably lower alkyl, that is substituted with an aryl group as defined above; e.g., —CH$_2$phenyl, —(CH$_2$)$_2$phenyl, —(CH$_2$)$_3$phenyl, CH$_3$CH(CH$_3$)CH$_2$phenyl, and the like and derivatives thereof.

"Heteroaralkyl" group means alkyl, preferably lower alkyl, that is substituted with a heteroaryl group; e.g., —CH$_2$pyridinyl, —(CH$_2$)$_2$pyrimidinyl, —(CH$_2$)$_3$imidazolyl, and the like, and derivatives thereof.

"Monoalkylamino" means a radical —NHR where R is an alkyl or unsubstituted cycloalkyl group; e.g., methylamino. (1-methylethyl)amino, cyclohexylamino, and the like.

"Dialkylamino" means a radical —NRR where each R is independently an alkyl or unsubstituted cycloalkyl group; dimethylamino, diethylamino, (1-methylethyl)-ethylamino, cyclohexylmethylamino, cyclopentylmethylamino, and the like.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arvisulfone, cyano, halo, acyl, nitro, haloalkyl, fluoroalkyl, amino, including mono- and di-substituted amino groups, and the protected derivatives thereof.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

As used herein, the term "pharmaceutically acceptable salt" refers to those salts which retain the biological effectiveness and properties of the parent compound. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

As used herein, when any variable occurs more than one time in a chemical formula, its definition on each occurrence is independent of its definition at every other occurrence. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan. Compounds of Formula I include, but are not limited to optical isomers of compounds of Formula I, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with double bonds. Where compounds of Formula I exist in various tautomeric forms, chemical entities of the present invention include all tautomeric forms of the compound.

Compounds of the present disclosure include, but are not limited to compounds of Formula I, and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used henceforth, the term "compound" encompasses not only the compound itself, but also a pharmaceutically acceptable salt thereof, a solvate thereof, a chelate thereof, a non-covalent complex thereof, a prodrug thereof, and mixtures of any of the foregoing.

As noted above, prodrugs also fall within the scope of chemical entities, for example, ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, and benzoate and like derivatives of functional groups (such as alcohol or amine groups) in the compounds of Formula I.

The present invention compounds can be in the form of composition by oral, inhalation, rectal or parenteral administration administered to patients in need of such treatment. For oral administration, it can be prepared into a solid dosage form such as tablets, powders, granules, capsules, etc., or a liquid dosage form such as aqueous agents, oil-based suspension, syrup, ect. For parenteral administration, the compound/pharmaceutical composition is a solution for injection, an aqueous agent, or an oil-based suspension. Preferably, the dosage form is tablets, coated tablets, capsules, suppositories, nasal sprays and injections, and more preferably, is a oral dosage.

The dosage forms of the compound and pharmaceutically composition disclosed in the invention can be prepared by the conventional methods in pharmaceutical industry. For example, the active ingredient is mixed with one or more excipients, and then formed into the desired dosage form.

EXAMPLES

The present invention is further exemplified, but not limited, by the following examples that illustrate the preparation of compounds of Formula (I) of the present invention.

The following examples are only used to disclose the preferred embodiments of the present invention, to help technicians in the art understand well, but are not used to limit the spirit and scope of the present invention. In the examples of the present invention, the approach or methods or the like is conventional in the art without specification. The compounds of the present invention can be prepared through, but not limited to, one or more of the following general reaction scheme:

Example 1

Synthesis of 2-amino-3-hydrogen-5-chloropyridine

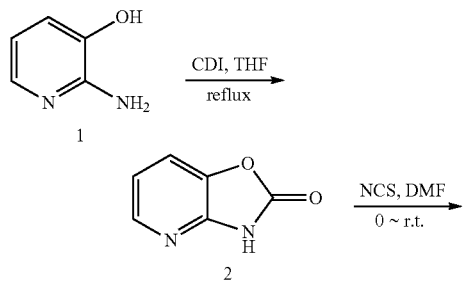

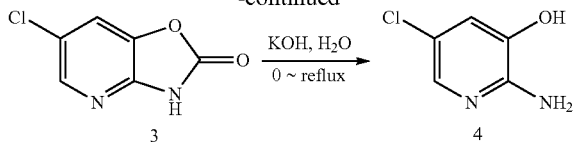

Step 1: To the solution of 2-amino-3-hydrogen-5-chloropyridine (19.8 g, 180.0 mmol) in THF (200 mL) was added N,N'-Carbonyl diimidazole (43.8 g, 270.0 mmol). The mixture was heated to 75° C. and stirred for 16 h. After the reaction was completed, the mixture was purified by column chromatography to give 17.63 g 2,3-dihydropyridino[2,3-d][1,3]azole-2-ketone, yield: 72%.

Step 2: To the solution of 2,3-dihydropyridino[2,3-d][1,3]azole-2-ketone in DMF (90 mL) at 0° C. was added NCS (12.3 g, 91.8 mmol) in DMF (50 mL) dropwise in 60 min. The mixture was warmed to room temperature and react for 3 h. To the reaction mixture was added 150 mL ice water, and stir for 30 min. The solid was collected by filtration to give the desired product (12.0 g).

Step 3: To the solution of 7.7 g KOH in 80 mL ice water is added 6-chlorooxazolo[4,5-b]pyridin-2(3H)-one (11.0 g, 64.5 mmol), the mixture was refluxed for 16 h. Then the mixture was cooled to room temperature, and adjusted to PH~8 with concentrated hydrochloric acid in an ice water bath. The solid was collected by filtration, and washed with water. After drying, 2-amino-3-hydrogen-5-chloropyridine was obtained as yellow solid (5.1 g).

Example 2

Synthesis of 3-((3-aminobenzyl)oxy)-5-chloropyridin-2-amine

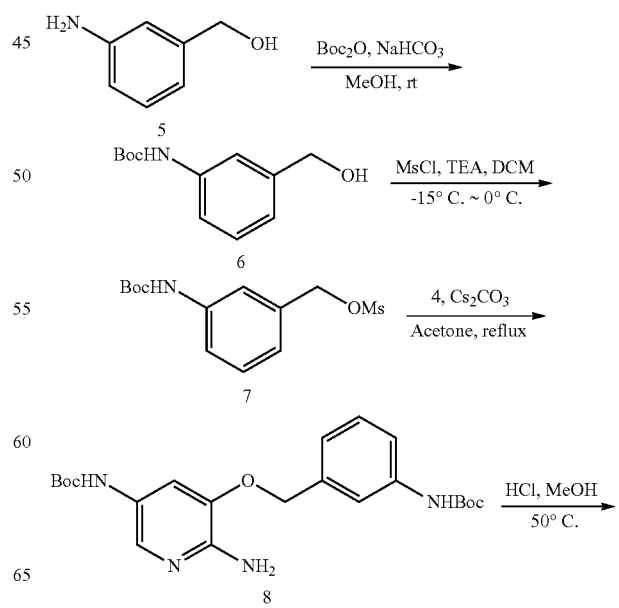

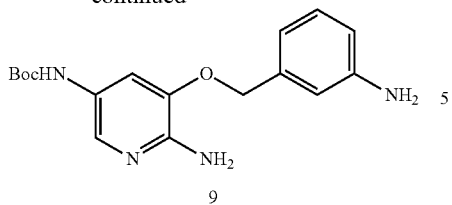

Step 1: To the solution of 3-aminobenzylalcohol (6.2 g, 50.0 mmol), and NaHCO₃ (6.3 g, 75.0 mmol) in 50 mL MeCN is added Boc₂O (13.1 g, 60.0 mmol) dropwise over 30 min. After stir at room temperature for 16 h, the sample was purified by column chromatography to give tert-butyl (3-(hydroxymethyl)phenyl)carbamate 6 as yellow oil (11.8 g).

Step 2: To the solution of 6 (5 g, 22.4 mmol), and TEA (12.54 mL, 89.6 mmol) in DCM (100 mL) was added MsCl (3.47 mL, 44.8 mmol) in DCM (20 mL) dropwise over 20 min at −15° C. under nitrogen atmosphere. The resulting mixture was warmed to 0° C., and stir for 16 h. The reaction mixture was poured into 100 mL water, and stir for 5 min. Collected the organic phase, concentrated in vacuo, and purified by column chromatography to give desired product 7 (1.86 g, 27.6%).

Step 3: To the solvent of acetone (30 mL) was added 7 (1.86 g, 6.18 mmol), 4 (896 mg, 6.18 mmol) and CsCO₃ (2.619 g, 8.03 mmol). The resulting mixture was heated to 60° C. and refluxed for 16 h. The reaction mixture was concentrated in vacuo, purified by column chromatography and dried in vacuo to give yellow solid 8 (810 mg, 37.5%).

Step 4: To the solution of 8 (810 mg, 2.3 mmol) in MeOH (10 mL) was added 12N HCl (0.5 mL). The mixture was stirred at 50° C. for 16 h, then concentrated in vacuo. The residue was mixed with toluene (5 mL), then reconcentrated to dryness in vacuo to give white solid, which is the hydrochloride of 9 (650 mg, 98.3%), LC-MS[M+H]-m/z: 250.

Example 3

Synthesis of Compounds 20-29

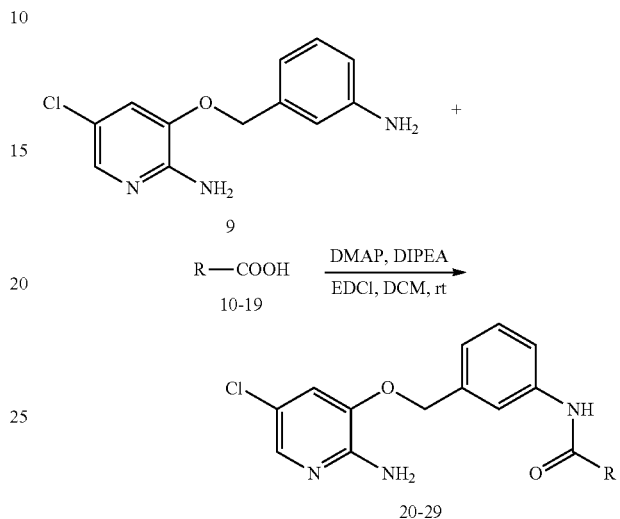

General Experimental Procedures:

To the flask was added 9 (57 mg, 0.2 mmol), R—COOH (1.2 eq, 0.24 mmol), EDCI (58 mg, 0.3 mmol), DMAP (5 mg, 0.04 mmol) in DCM (5 mL) successively, followed by DIPEA (77 mg, 0.6 mmol) with stirring. The resulting mixture was stirred at room temperature for overnight, and purified by column chromatography to give product.

TABLE 1

| Comps. No. | Compound structure | Compound name | MS [M + 1] |
|---|---|---|---|
| 20 | 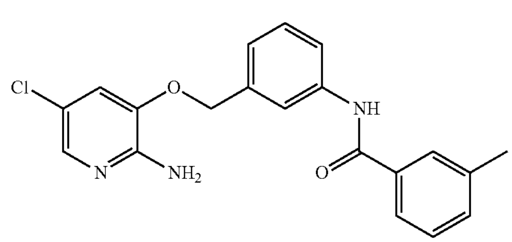 [SMILES: Cc1cccc(C(=O)Nc2cccc(COc3cc(Cl)cnc3N)c2)c1] | N-(3-(((2-amino-5-chloropyridin-3-yl)oxy)methyl)phenyl)-3-methyl-benzamide | 368 |
| 21 | 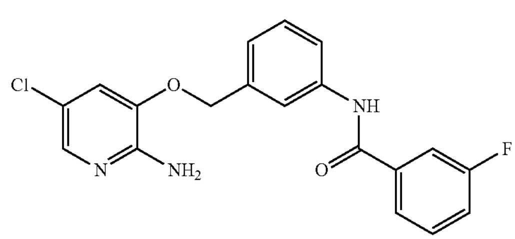 [SMILES: Nc1ncc(Cl)cc1OCc1cccc(NC(=O)c2cccc(F)c2)c1] | N-(3-(((2-amino-5-chloropyridin-3-yl)oxy)methyl)phenyl)-3-fluoro-benzamide | 372 |

TABLE 1-continued

| Comps. No. | Compound structure | Compound name | MS [M + 1] |
|---|---|---|---|
| 22 | 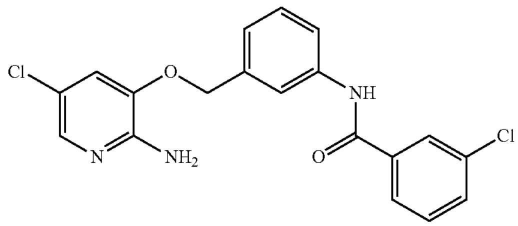 [SMILES: Nc1ncc(Cl)cc1OCc1cccc(NC(=O)c2cccc(Cl)c2)c1] | N-(3-(((2-amino-5-chloropyridin-3-yl)oxy)methyl)phenyl)-3-chlorobenzamide | 388 |
| 23 | 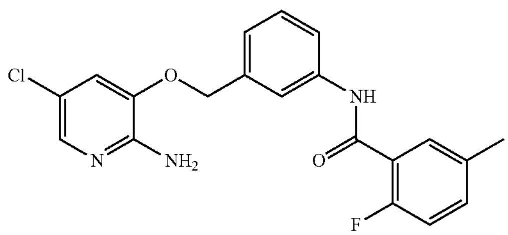 [SMILES: Cc1ccc(F)c(C(=O)Nc2cccc(COc3cc(Cl)cnc3N)c2)c1] | N-(3-(((2-amino-5-chloropyridin-3-yl)oxy)methyl)phenyl)-2-fluoro-5-methylbenzamide | 386 |
| 24 | 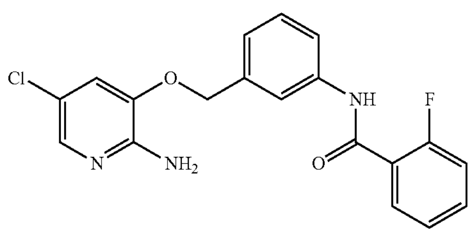 [SMILES: Nc1ncc(Cl)cc1OCc1cccc(NC(=O)c2ccccc2F)c1] | N-(3-(((2-amino-5-chloropyridin-3-yl)oxy)methyl)phenyl)-2-fluorobenzamide | 372 |
| 25 | 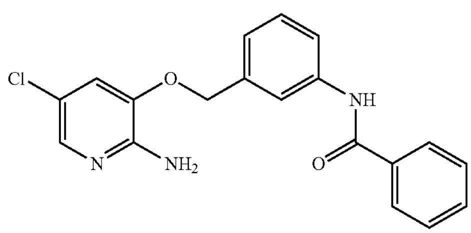 [SMILES: Nc1ncc(Cl)cc1OCc1cccc(NC(=O)c2ccccc2)c1] | N-(3-(((2-amino-5-chloropyridin-3-yl)oxy)methyl)phenyl)benzamide | 354 |
| 26 | 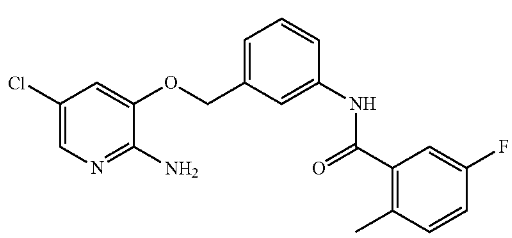 [SMILES: Cc1ccc(F)cc1C(=O)Nc1cccc(COc2cc(Cl)cnc2N)c1] | N-(3-(((2-amino-5-chloropyridin-3-yl)oxy)methyl)phenyl)-5-fluoro-2-methylbenzamide | 386 |
| 27 | 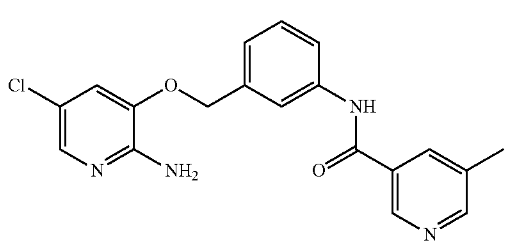 [SMILES: Cc1cncc(C(=O)Nc2cccc(COc3cc(Cl)cnc3N)c2)c1] | N-(3-(((2-amino-5-chloropyridin-3-yl)oxy)methyl)phenyl)-5-methylnicotinamide | 369 |

TABLE 1-continued

| Comps. No. | Compound structure | Compound name | MS [M + 1] |
|---|---|---|---|
| 28 | 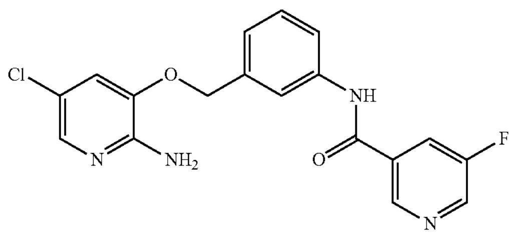 [SMILES: Nc1ncc(Cl)cc1OCc1cccc(NC(=O)c2cncc(F)c2)c1] | N-(3-(((2-amino-5-chloropyridin-3-yl)oxy)methyl)phenyl)-5-fluoro-nicotinamide | 373 |
| 29 | 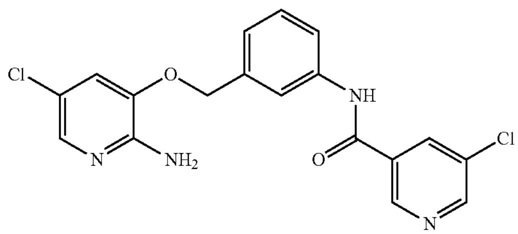 [SMILES: Nc1ncc(Cl)cc1OCc1cccc(NC(=O)c2cncc(Cl)c2)c1] | N-(3-(((2-amino-5-chloropyridin-3-yl)oxy)methyl)phenyl)-5-chloro-nicotinamide | 389 |

Example 4

Synthesis of tert-butyl (S)-(3-(1-hydroxyethyl)phenyl)carbamate

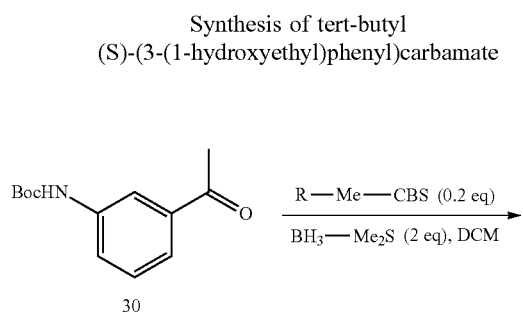

To the dried three-necked flask was added R-methyl-CBS-oxazaborolidine (0.2 eq), BMS (10 M, 2.0 eq) under nitrogen atmosphere. The resulting mixture was diluted with DCM, and stir at 25° C. for 30 min. Then cooled to −30° C., (3-acetylphenyl)tert-butyl carbamate in DCM was added dropwise over 30 min. The mixture was continued to stir for 3 h at −30° C. TLC was used to monitor the reaction. After the reaction was completed, it was quenched by adding MeOH over 30 min. The resulting mixture was stirred at 80° C. for 1 h, then concentrated in vacuo, purified by column chromatography (PE/EA=3:1) and dried in vacuo to give the desired product as colorless oil. LC-MS[M+Na]-m/z: 260.

Example 5

Synthesis of Compounds 54-71

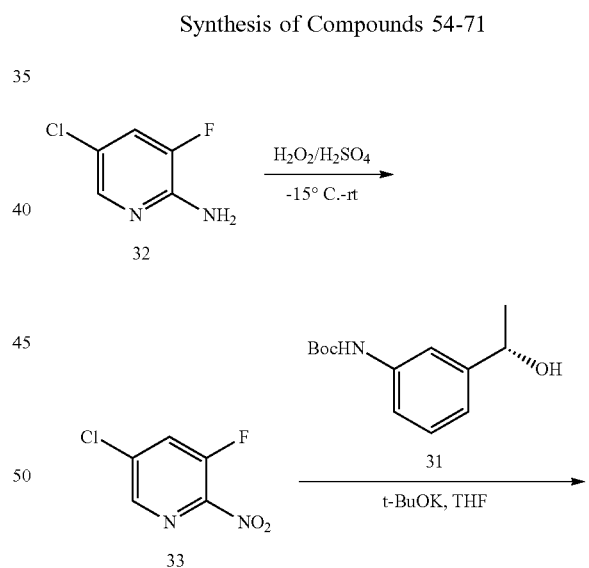

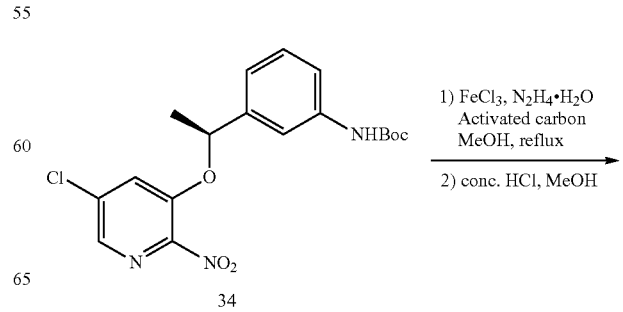

-continued

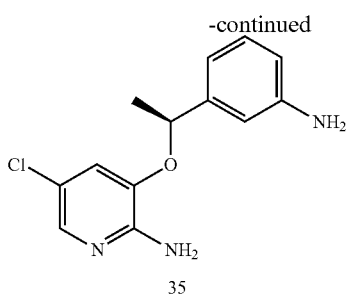

35

R—COOH
36-53

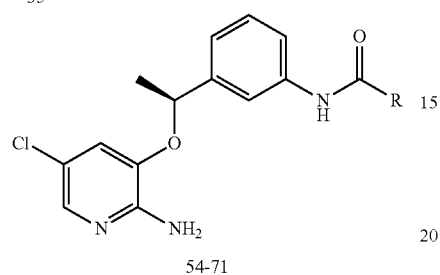

54-71

Step 1: To concentrated sulfuric acid (100 mL) cooled to −10° C. was added 2-amino-3-fluoro-5-chloropyridine (10 g, 68.2 mmol) with stirring. After dissolution, the mixture was continued to stir at −10° C. for 15 min. Then 50 mL 30% hydrogen peroxide solution was added slowly, and the reaction temperature was maintained below 0° C. The mixture was warmed to room temperature and stirred for 72 h, then poured into 500 mL 13% ice brine with stirring and extracted with 200 mL EA for three times. The combined organic extracts were washed with saturated sodium bicarbonate solution until the aqueous phase was alkaline, dried with anhydrous sodium sulfate and concentrated in vacuo. The residue was purified by column chromatography to give the desired product 2-nitro-3-fluoro-5-chloropyridine (2.8 g, 23.3%).

Step 2: To the solution of 31 (1.0 g, 4.2 mmol) in dried THF (10 mL) was added potassium tert-butoxide (517.0 mg. 4.6 mmol), the mixture was stirred at room temperature for 10 min, then added 2-nitro-3-fluoro-5-chloropyridine (741.0 mg, 4.6 mmol), and stirred at room temperature for 1 h. The mixture was quenched by the addition of 10 g silica gel, and purified by column chromatography to give the desired product (1.50 g, 95%).

Step 3: The suspension of 34 (1.50 g, 3.8 mmol), anhydrous ferric chloride (60 mg, 0.38 mmol) and activated carbon (200 mg) in 10 mL MeOH was refluxed for 15 min. Then hydrazine hydrate (80% aqueous solution, 600 mg, 9.5 mmol) was added and the resulting mixture was refluxed for 1 h, poured into 100 mL 13% brine and extracted with 50 mL EA for three times. The combined organic extracts were washed with brine for three times, dried with anhydrous sodium sulfate and concentrated in vacuo to give white solid (1.0 g, 2.5 mmol). The solid was redissolved in 10 mL methanol, and added 1 mL concentrated hydrochloric acid. The resulting mixture was stirred at 50° C. for 3 h, then cooled to room temperature, and concentrated in vacuo. The residue was poured into 100 mL saturated sodium bicarbonate solution, and extracted with 50 mL EA for three times. The combined organic phase was dried with anhydrous sodium sulfate and concentrated to dryness in vacuo to give the desired product as yellow oil (602 mg).

Step 4: Synthesis of compounds 54-71 was similar procedure to the example 3.

TABLE 2

| Comps. No. | Compound structure | Compound name | MS [M + 1] |
|---|---|---|---|
| 54 | 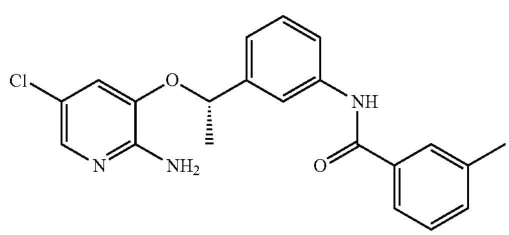 [SMILES: Cc1cccc(C(=O)Nc2cccc([C@H](C)Oc3cc(Cl)cnc3N)c2)c1] | (S)-N-(3-(1-((2-amino-5-chloropyridin-3-yl)oxy)ethyl)-phenyl)-3-methylbenzamide | 382 |
| 55 | 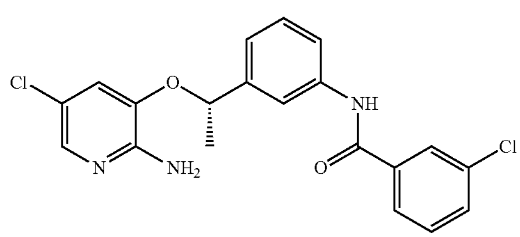 [SMILES: C[C@H](Oc1cc(Cl)cnc1N)c1cccc(NC(=O)c2cccc(Cl)c2)c1] | (S)-N-(3-(1-((2-amino-5-chloropyridin-3-yl)oxy)ethyl)-phenyl)-3-chlorobenzamide | 402 |

TABLE 2-continued

| Comps. No. | Compound structure | Compound name | MS [M + 1] |
|---|---|---|---|
| 56 | 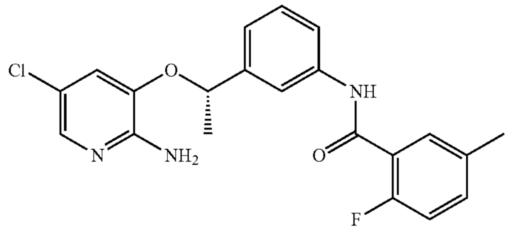 | (S)-N-(3-(1-((2-amino-5-chloropyridin-3-yl)oxy)ethyl)-phenyl)-2-fluoro-5-methylbenzamide | 400 |
| 57 | 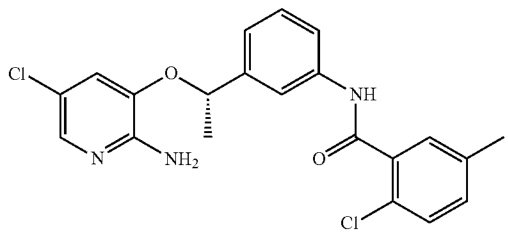 [SMILES: Cc1ccc(Cl)c(C(=O)Nc2cccc([C@H](C)Oc3cc(Cl)cnc3N)c2)c1] | (S)-N-(3-(1-((2-amino-5-chloropyridin-3-yl)oxy)ethyl)-phenyl)-2-chloro-5-methylbenzamide | 416 |
| 58 | 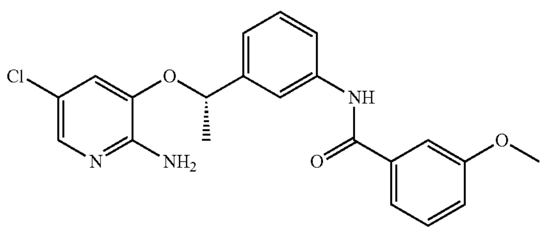 [SMILES: COc1cccc(C(=O)Nc2cccc([C@H](C)Oc3cc(Cl)cnc3N)c2)c1] | (S)-N-(3-(1-((2-amino-5-chloropyridin-3-yl)oxy)ethyl)-phenyl)-3-methoxybenzamide | 398 |
| 59 | 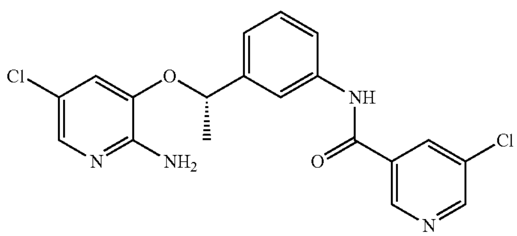 [SMILES: C[C@H](Oc1cc(Cl)cnc1N)c1cccc(NC(=O)c2cncc(Cl)c2)c1] | (S)-N-(3-(1-((2-amino-5-chloropyridin-3-yl)oxy)ethyl)-phenyl)-5-chloronicotinamide | 403 |
| 60 | 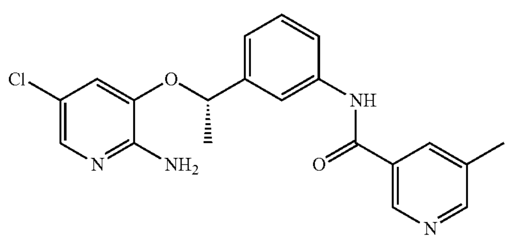 [SMILES: Cc1cncc(C(=O)Nc2cccc([C@H](C)Oc3cc(Cl)cnc3N)c2)c1] | (S)-N-(3-(1-((2-amino-5-chloropyridin-3-yl)oxy)ethyl)-phenyl)-5-methylnicotinamide | 383 |
| 61 | 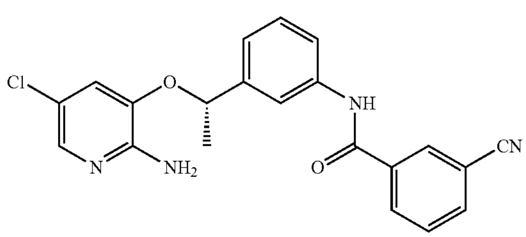 [SMILES: C[C@H](Oc1cc(Cl)cnc1N)c1cccc(NC(=O)c2cccc(C#N)c2)c1] | (S)-N-(3-(1-((2-amino-5-chloropyridin-3-yl)oxy)ethyl)-phenyl)-3-cyanobenzamide | 393 |

TABLE 2-continued

| Comps. No. | Compound structure | Compound name | MS [M + 1] |
|---|---|---|---|
| 62 | 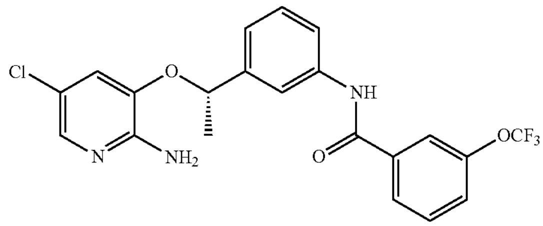 [SMILES: C[C@H](Oc1cc(Cl)cnc1N)c1cccc(NC(=O)c2cccc(OC(F)(F)F)c2)c1] | (S)-N-(3-(1-((2-amino-5-chloropyridin-3-yl)oxy)ethyl)-phenyl)-3-(trifluoromethoxy)-benzamide | 452 |
| 63 | 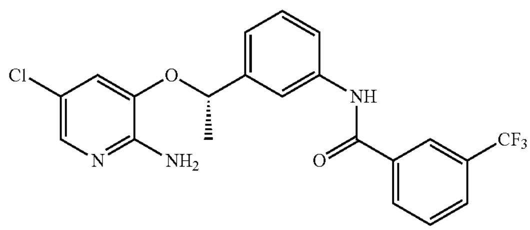 [SMILES: C[C@H](Oc1cc(Cl)cnc1N)c1cccc(NC(=O)c2cccc(C(F)(F)F)c2)c1] | (S)-N-(3-(1-((2-amino-5-chloropyridin-3-yl)oxy)ethyl)-phenyl)-3-(trifluoromethyl)-benzamide | 436 |
| 64 | 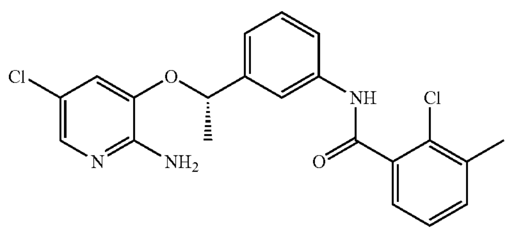 [SMILES: Cc1cccc(C(=O)Nc2cccc([C@H](C)Oc3cc(Cl)cnc3N)c2)c1Cl] | (S)-N-(3-(1-((2-amino-5-chloropyridin-3-yl)oxy)ethyl)-phenyl)-2-chloro-3-methylbenzamide | 416 |
| 65 | 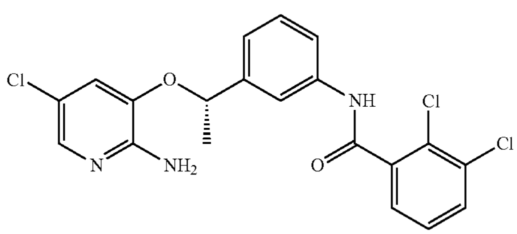 [SMILES: C[C@H](Oc1cc(Cl)cnc1N)c1cccc(NC(=O)c2cccc(Cl)c2Cl)c1] | (S)-N-(3-(1-((2-amino-5-chloropyridin-3-yl)oxy)ethyl)-phenyl)-2,3-dichlorobenzamide | 436 |
| 66 | 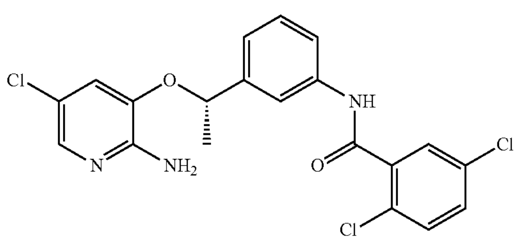 [SMILES: C[C@H](Oc1cc(Cl)cnc1N)c1cccc(NC(=O)c2cc(Cl)ccc2Cl)c1] | (S)-N-(3-(1-((2-amino-5-chloropyridin-3-yl)oxy)ethyl)-phenyl)-2,5-dichlorobenzamide | 436 |
| 67 | 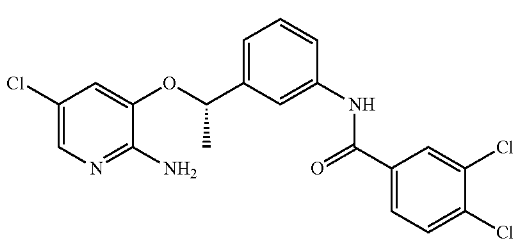 [SMILES: C[C@H](Oc1cc(Cl)cnc1N)c1cccc(NC(=O)c2ccc(Cl)c(Cl)c2)c1] | (S)-N-(3-(1-((2-amino-5-chloropyridin-3-yl)oxy)ethyl)-phenyl)-3,4-dichlorobenzamide | 436 |

TABLE 2-continued

| Comps. No. | Compound structure | Compound name | MS [M + 1] |
|---|---|---|---|
| 68 | 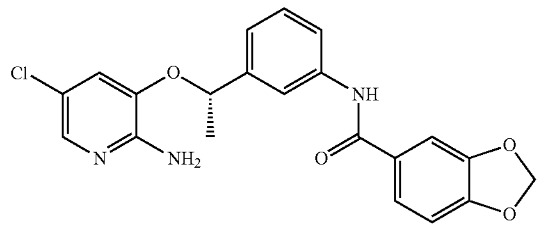 [SMILES: C[C@H](Oc1cc(Cl)cnc1N)c1cccc(NC(=O)c2ccc3c(c2)OCO3)c1] | (S)-N-(3-(1-((2-amino-5-chloropyridin-3-yl)oxy)ethyl)-phenyl)benzo[d][1,3]dioxole-5-carboxamide | 412 |
| 69 | 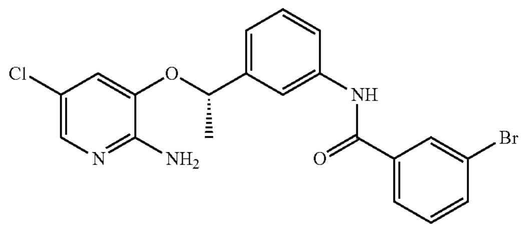 [SMILES: C[C@H](Oc1cc(Cl)cnc1N)c1cccc(NC(=O)c2cccc(Br)c2)c1] | (S)-N-(3-(1-((2-amino-5-chloropyridin-3-yl)oxy)ethyl)-phenyl)-3-bromobenzamide | 446 |
| 70 | 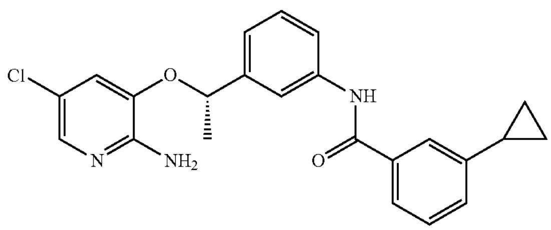 [SMILES: C[C@H](Oc1cc(Cl)cnc1N)c1cccc(NC(=O)c2cccc(C3CC3)c2)c1] | (S)-N-(3-(1-((2-amino-5-chloropyridin-3-yl)oxy)ethyl)-phenyl)-3-cyclopropylbenzamide | 408 |
| 71 | 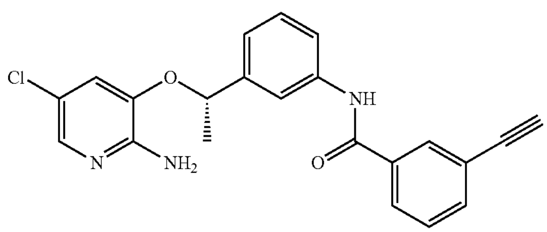 [SMILES: C#Cc1cccc(C(=O)Nc2cccc([C@H](C)Oc3cc(Cl)cnc3N)c2)c1] | (S)-N-(3-(1-((2-amino-5-chloropyridin-3-yl)oxy)ethyl)-phenyl)-3-ethynylbenzamide | 392 |

Example 6

Synthesis of Compounds 72-164 was Similar Procedure to that of Compound 54-71

TABLE 3

| Comps. No. | Compound structure | Compound name | MS [M + 1] |
|---|---|---|---|
| 72 | 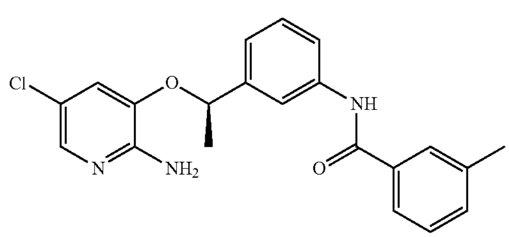 [SMILES: Cc1cccc(C(=O)Nc2cccc([C@@H](C)Oc3cc(Cl)cnc3N)c2)c1] | (R)-N-(3-(1-((2-amino-5-chloropyridin-3-yl)oxy)ethyl)-phenyl)-3-methylbenzamide | 382 |

TABLE 3-continued

| Comps. No. | Compound structure | Compound name | MS [M + 1] |
|---|---|---|---|
| 73 | 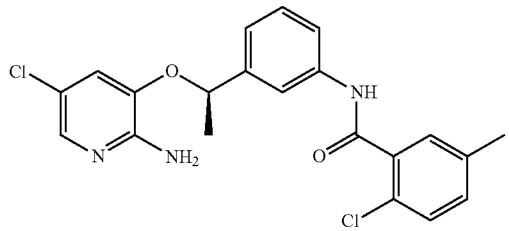 [SMILES: Cc1ccc(Cl)c(C(=O)Nc2cccc([C@@H](C)Oc3cc(Cl)cnc3N)c2)c1] | (R)-N-(3-(1-((2-amino-5-chloropyridin-3-yl)oxy)ethyl)-phenyl)-2-chloro-5-methylbenzamide | 416 |
| 74 | 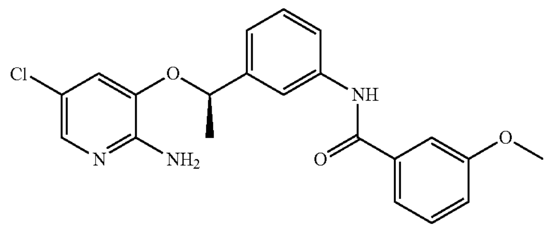 [SMILES: COc1cccc(C(=O)Nc2cccc([C@@H](C)Oc3cc(Cl)cnc3N)c2)c1] | (R)-N-(3-(1-((2-amino-5-chloropyridin-3-yl)oxy)ethyl)-phenyl)-3-methoxybenzamide | 398 |
| 75 | 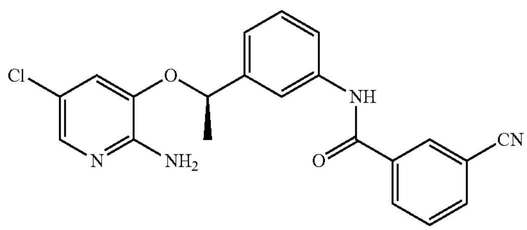 [SMILES: C[C@@H](Oc1cc(Cl)cnc1N)c1cccc(NC(=O)c2cccc(C#N)c2)c1] | (R)-N-(3-(1-((2-amino-5-chloropyridin-3-yl)oxy)ethyl)-phenyl)-3-cyanobenzamide | 393 |
| 76 | 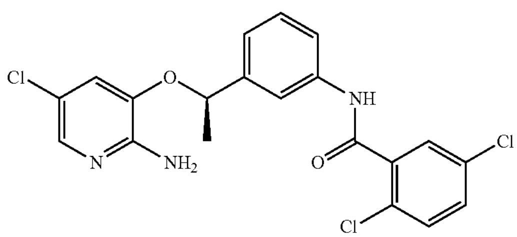 [SMILES: C[C@@H](Oc1cc(Cl)cnc1N)c1cccc(NC(=O)c2cc(Cl)ccc2Cl)c1] | (R)-N-(3-(1-((2-amino-5-chloropyridin-3-yl)oxy)ethyl)-phenyl)-2,5-dichlorobenzamide | 436 |
| 77 | 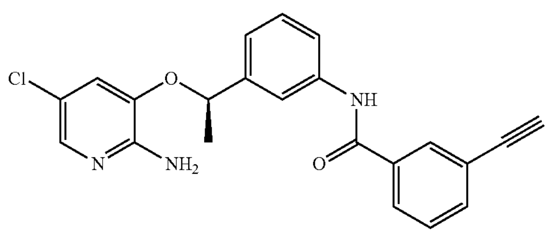 [SMILES: C#Cc1cccc(C(=O)Nc2cccc([C@@H](C)Oc3cc(Cl)cnc3N)c2)c1] | (R)-N-(3-(1-((2-amino-5-chloropyridin-3-yl)oxy)ethyl)-phenyl)-3-ethynylbenzamide | 392 |
| 78 | 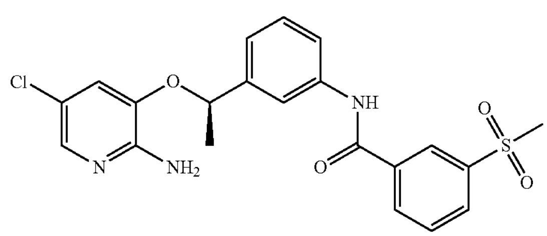 [SMILES: C[C@@H](Oc1cc(Cl)cnc1N)c1cccc(NC(=O)c2cccc(S(C)(=O)=O)c2)c1] | (R)-N-(3-(1-((2-amino-5-chloropyridin-3-yl)oxy)ethyl)-phenyl)-3-(methylsulfonyl)-benzamide | 446 |

TABLE 3-continued

| Comps. No. | Compound structure | Compound name | MS [M + 1] |
|---|---|---|---|
| 79 | 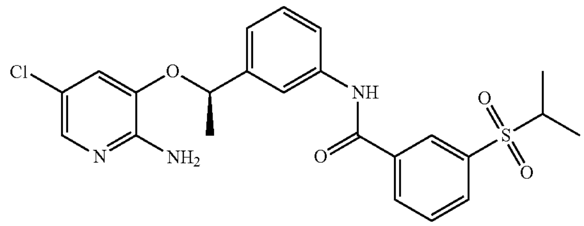 [SMILES: CC(C)S(=O)(=O)c1cccc(C(=O)Nc2cccc([C@@H](C)Oc3cc(Cl)cnc3N)c2)c1] | (R)-N-(3-(1-((2-amino-5-chloropyridin-3-yl)oxy)ethyl)-phenyl)-3-(isopropylsulfonyl)-benzamide | 474 |
| 80 | 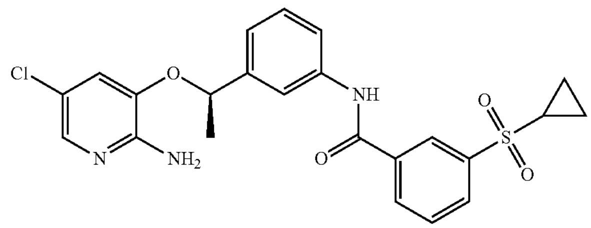 [SMILES: C[C@@H](Oc1cc(Cl)cnc1N)c1cccc(NC(=O)c2cccc(S(=O)(=O)C3CC3)c2)c1] | (R)-N-(3-(1-((2-amino-5-chloropyridin-3-yl)oxy)ethyl)-phenyl)-3-(cyclopropylsulfonyl)-benzamide | 472 |
| 81 | 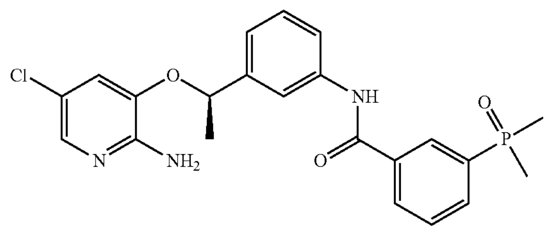 [SMILES: C[C@@H](Oc1cc(Cl)cnc1N)c1cccc(NC(=O)c2cccc(P(C)(C)=O)c2)c1] | (R)-N-(3-(1-((2-amino-5-chloropyridin-3-yl)oxy)ethyl)-phenyl)-3-(dimethylphosphoryl)-benzamide | 444 |
| 82 | 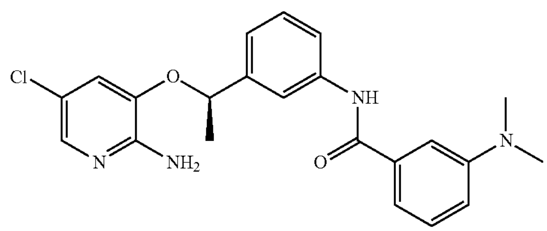 [SMILES: C[C@@H](Oc1cc(Cl)cnc1N)c1cccc(NC(=O)c2cccc(N(C)C)c2)c1] | (R)-N-(3-(1-((2-amino-5-chloropyridin-3-yl)oxy)ethyl)-phenyl)-3-(dimethylamino)benzamide | 411 |
| 83 | 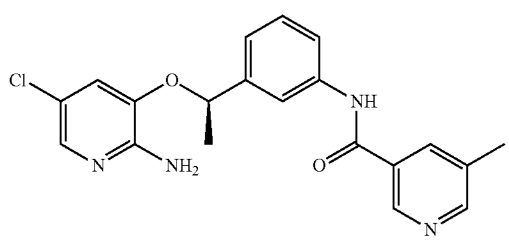 [SMILES: Cc1cncc(C(=O)Nc2cccc([C@@H](C)Oc3cc(Cl)cnc3N)c2)c1] | (R)-N-(3-(1-((2-amino-5-chloropyridin-3-yl)oxy)ethyl)-phenyl)-5-methylnicotinamide | 383 |
| 84 | 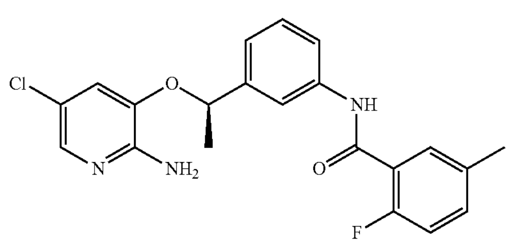 [SMILES: Cc1ccc(F)c(C(=O)Nc2cccc([C@@H](C)Oc3cc(Cl)cnc3N)c2)c1] | (R)-N-(3-(1-((2-amino-5-chloropyridin-3-yl)oxy)ethyl)-phenyl)-2-fluoro-5-methylbenzamide | 400 |

TABLE 3-continued

| Comps. No. | Compound structure | Compound name | MS [M + 1] |
|---|---|---|---|
| 85 | 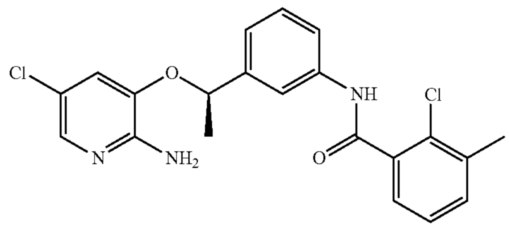 [SMILES: Cc1cccc(C(=O)Nc2cccc([C@@H](C)Oc3cc(Cl)cnc3N)c2)c1Cl] | (R)-N-(3-(1-((2-amino-5-chloropyridin-3-yl)oxy)ethyl)-phenyl)-2-chloro-3-methylbenzamide | 416 |
| 86 | 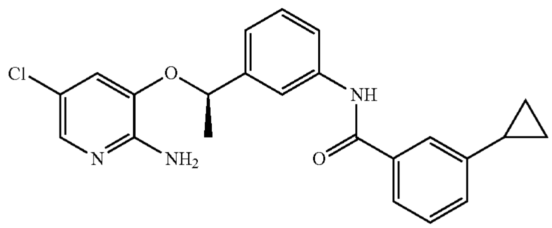 | (R)-N-(3-(1-((2-amino-5-chloropyridin-3-yl)oxy)ethyl)-phenyl)-3-cyclopropylbenzamide | 408 |
| 87 | 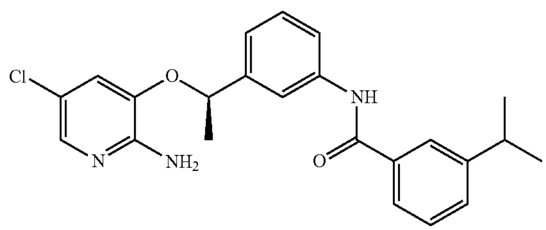 [SMILES: CC(C)c1cccc(C(=O)Nc2cccc([C@@H](C)Oc3cc(Cl)cnc3N)c2)c1] | (R)-N-(3-(1-((2-amino-5-chloropyridin-3-yl)oxy)ethyl)-phenyl)-3-isopropylbenzamide | 410 |
| 88 | 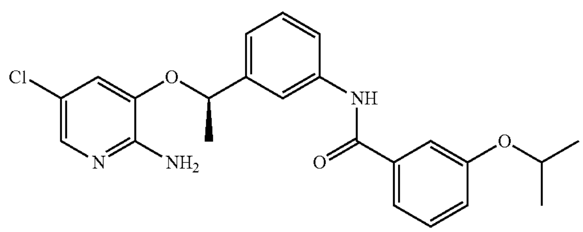 [SMILES: CC(C)Oc1cccc(C(=O)Nc2cccc([C@@H](C)Oc3cc(Cl)cnc3N)c2)c1] | (R)-N-(3-(1-((2-amino-5-chloropyridin-3-yl)oxy)ethyl)-phenyl)-3-isopropoxybenzamide | 426 |
| 89 | 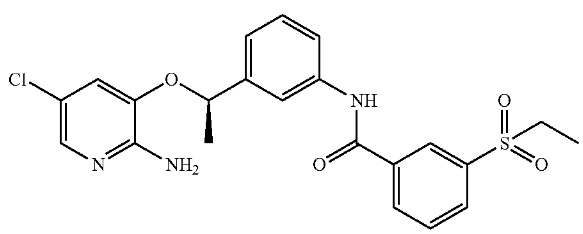 [SMILES: CCS(=O)(=O)c1cccc(C(=O)Nc2cccc([C@@H](C)Oc3cc(Cl)cnc3N)c2)c1] | (R)-N-(3-(1-((2-amino-5-chloropyridin-3-yl)oxy)ethyl)-phenyl)-3-(ethylsulfonyl)-benzamide | 460 |
| 90 | 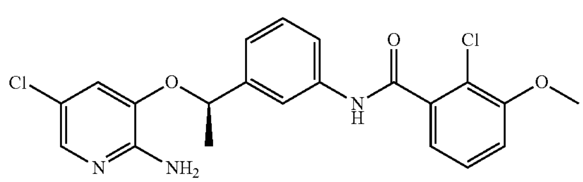 [SMILES: COc1cccc(C(=O)Nc2cccc([C@@H](C)Oc3cc(Cl)cnc3N)c2)c1Cl] | (R)-N-(3-(1-((2-amino-5-chloropyridin-3-yl)oxy)ethyl)-phenyl)-2-chloro-3-methoxybenzamide | 432 |
| 91 | 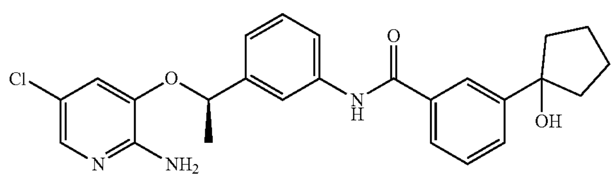 [SMILES: C[C@@H](Oc1cc(Cl)cnc1N)c1cccc(NC(=O)c2cccc(C3(O)CCCC3)c2)c1] | (R)-N-(3-(1-((2-amino-5-chloropyridin-3-yl)oxy)ethyl)-phenyl)-3-(1-hydroxycyclopentyl)-benzamide | 452 |

TABLE 3-continued

| Comps. No. | Compound structure | Compound name | MS [M + 1] |
|---|---|---|---|
| 92 | 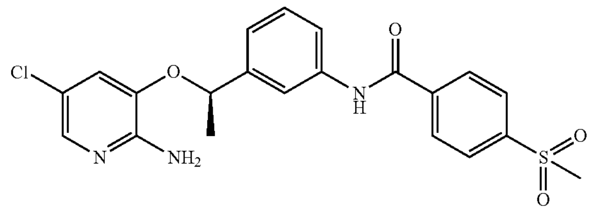 [SMILES: C[C@@H](Oc1cc(Cl)cnc1N)c1cccc(NC(=O)c2ccc(S(C)(=O)=O)cc2)c1] | (R)-N-(3-(1-((2-amino-5-chloropyridin-3-yl)oxy)ethyl)-phenyl)-4-(methylsulfonyl)-benzamide | 446 |
| 93 | 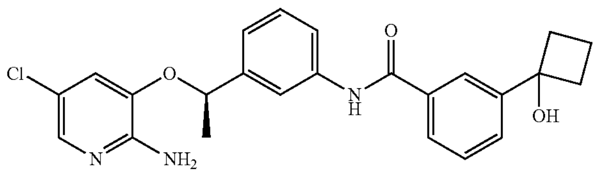 [SMILES: C[C@@H](Oc1cc(Cl)cnc1N)c1cccc(NC(=O)c2cccc(C3(O)CCC3)c2)c1] | (R)-N-(3-(1-((2-amino-5-chloropyridin-3-yl)oxy)ethyl)-phenyl)-3-(1-hydroxycyclobutyl)-benzamide | 438 |
| 94 | 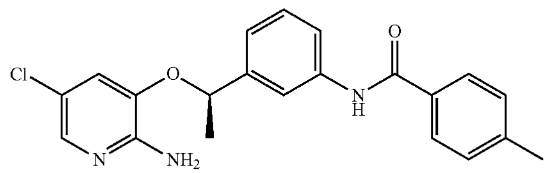 [SMILES: Cc1ccc(C(=O)Nc2cccc([C@@H](C)Oc3cc(Cl)cnc3N)c2)cc1] | (R)-N-(3-(1-((2-amino-5-chloropyridin-3-yl)oxy)ethyl)-phenyl)-4-methylbenzamide | 382 |
| 95 | 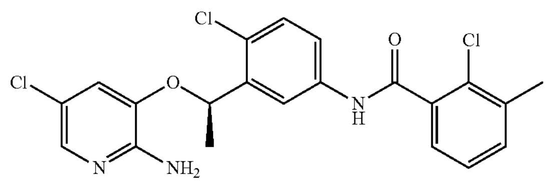 [SMILES: Cc1cccc(C(=O)Nc2ccc(Cl)c([C@@H](C)Oc3cc(Cl)cnc3N)c2)c1Cl] | (R)-N-(3-(1-((2-amino-5-chloropyridin-3-yl)oxy)ethyl)-4-chlorophenyl)-2-chloro-3-methylbenzamide | 450 |
| 96 | 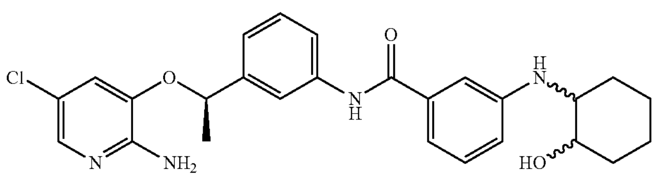 [SMILES: C[C@@H](Oc1cc(Cl)cnc1N)c1cccc(NC(=O)c2cccc(NC3CCCCC3O)c2)c1] | N-(3-((R)-1-(1-((2-amino-5-chloropyridin-3-yl)oxy)ethyl)-phenyl)-3-((2-hydroxycyclohexyl)-amino)benzamide | 481 |
| 97 | 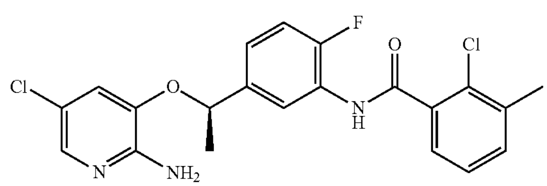 [SMILES: Cc1cccc(C(=O)Nc2cc([C@@H](C)Oc3cc(Cl)cnc3N)ccc2F)c1Cl] | (R)-N-(5-(1-((2-amino-5-chloropyridin-3-yl)oxy)ethyl)-2-fluorophenyl)-2-chloro-3-methylbenzamide | 434 |
| 98 | 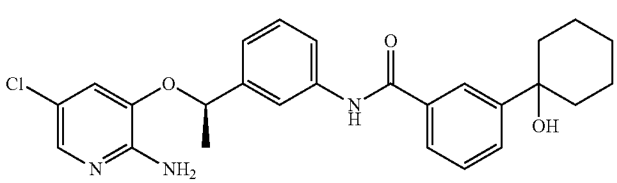 [SMILES: C[C@@H](Oc1cc(Cl)cnc1N)c1cccc(NC(=O)c2cccc(C3(O)CCCCC3)c2)c1] | (R)-N-(3-(1-((2-amino-5-chloropyridin-3-yl)oxy)ethyl)-phenyl)-3-(1-hydroxycyclohexyl)-benzamide | 466 |
| 99 | 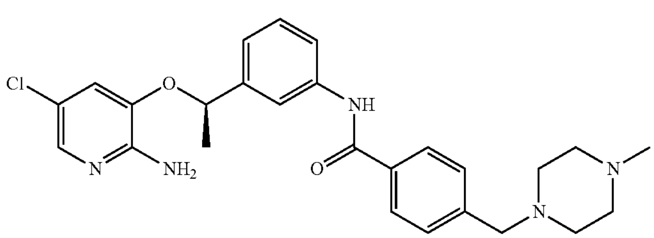 [SMILES: C[C@@H](Oc1cc(Cl)cnc1N)c1cccc(NC(=O)c2ccc(CN3CCN(C)CC3)cc2)c1] | (R)-N-(3-(1-((2-amino-5-chloropyridin-3-yl)oxy)ethyl)-phenyl)-4-((4-methylpiperazin-1-yl)methyl)benzamide | 480 |

TABLE 3-continued

| Comps. No. | Compound structure | Compound name | MS [M + 1] |
|---|---|---|---|
| 100 | 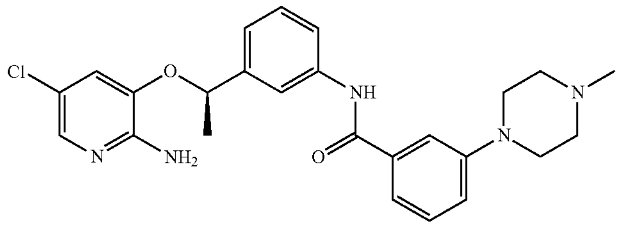 [SMILES: C[C@@H](Oc1cc(Cl)cnc1N)c1cccc(NC(=O)c2cccc(N3CCN(C)CC3)c2)c1] | (R)-N-(3-(1-((2-amino-5-chloropyridin-3-yl)oxy)ethyl)-phenyl)-3-(methylpiperazin-1-yl)-benzamide | 466 |
| 101 | 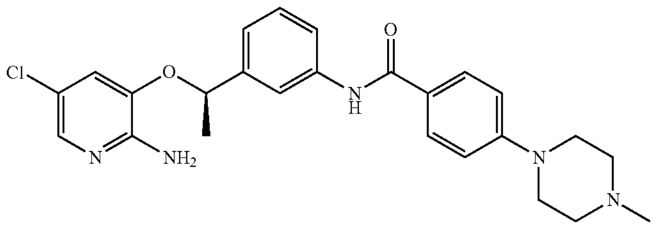 [SMILES: C[C@@H](Oc1cc(Cl)cnc1N)c1cccc(NC(=O)c2ccc(N3CCN(C)CC3)cc2)c1] | (R)-N-(3-(1-((2-amino-5-chloropyridin-3-yl)oxy)ethyl)-phenyl)-4-(4-methylpiperazin-1-yl)benzamide | 466 |
| 102 | 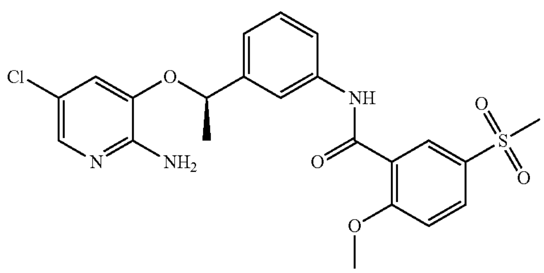 [SMILES: COc1ccc(S(C)(=O)=O)cc1C(=O)Nc1cccc([C@@H](C)Oc2cc(Cl)cnc2N)c1] | (R)-N-(3-(1-((2-amino-5-chloropyridin-3-yl)oxy)ethyl)-phenyl)-2-methoxy-5-(methylsulfonyl)benzamide | 476 |
| 103 | 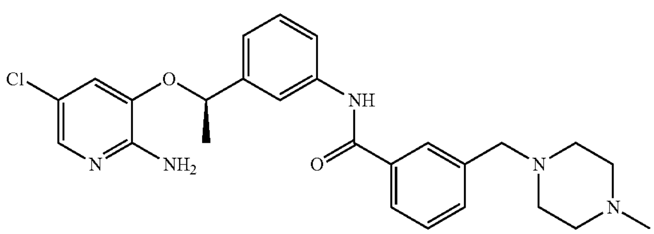 [SMILES: C[C@@H](Oc1cc(Cl)cnc1N)c1cccc(NC(=O)c2cccc(CN3CCN(C)CC3)c2)c1] | (R)-N-(3-(1-((2-amino-5-chloropyridin-3-yl)oxy)ethyl)-phenyl)-3-((4-methylpiperazin-1-yl)methyl)benzamide | 480 |
| 104 | 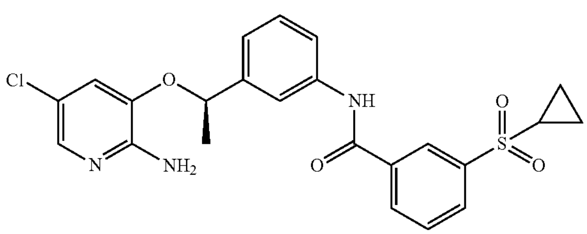 [SMILES: C[C@@H](Oc1cc(Cl)cnc1N)c1cccc(NC(=O)c2cccc(S(=O)(=O)C3CC3)c2)c1] | (R)-N-(3-(1-((2-amino-5-chloropyridin-3-yl)oxy)ethyl)-phenyl)-3-(cyclopropylsulfonyl)-benzamide | 472 |
| 105 | 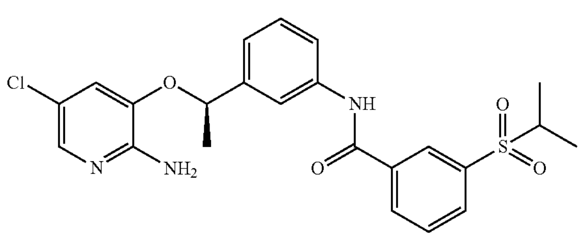 [SMILES: CC(C)S(=O)(=O)c1cccc(C(=O)Nc2cccc([C@@H](C)Oc3cc(Cl)cnc3N)c2)c1] | (R)-N-(3-(1-((2-amino-5-chloropyridin-3-yl)oxy)ethyl)-phenyl)-3-(isopropylsulfonyl)-benzamide | 474 |

TABLE 3-continued

| Comps. No. | Compound name | MS [M + 1] |
|---|---|---|
| 106 | (R)-N-(3-(1-((2-amino-5-chloropyridin-3-yl)oxy)ethyl)-phenyl)-3-(cyclopentylsulfonyl)benzamide | 500 |
| 107 | (R)-N-(3-(1-((2-amino-5-chloropyridin-3-yl)oxy)ethyl)-phenyl)quinoline-3-carboxamide | 419 |
| 108 | (R)-N-(3-(1-((2-amino-5-chloropyridin-3-yl)oxy)ethyl)-phenyl)isoquinoline-6-carboxamide | 419 |
| 109 | (R)-N-(3-(1-((2-amino-5-chloropyridin-3-yl)oxy)ethyl)-phenyl)quinoline-6-carboxamide | 419 |
| 110 | (R)-N-(3-(1-((2-amino-5-chloropyridin-3-yl)oxy)ethyl)-phenyl)-3-(pyrrolidin-1-ylsulfonyl)-benzamide | 501 |
| 111 | (R)-N-(3-(1-((2-amino-5-chloropyridin-3-yl)oxy)ethyl)-phenyl)-5-cyclopropylnicotinamide | 409 |

TABLE 3-continued

| Comps. No. | Compound structure | Compound name | MS [M + 1] |
|---|---|---|---|
| 112 | 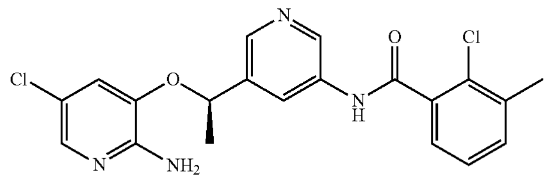 [SMILES: Cc1cccc(C(=O)Nc2cncc([C@@H](C)Oc3cc(Cl)cnc3N)c2)c1Cl] | (R)-N-(5-(1-((2-amino-5-chloropyridin-3-yl)oxy)ethyl)-pyridin-3-yl)-2-chloro-3-methylbenzamide | 417 |
| 113 | 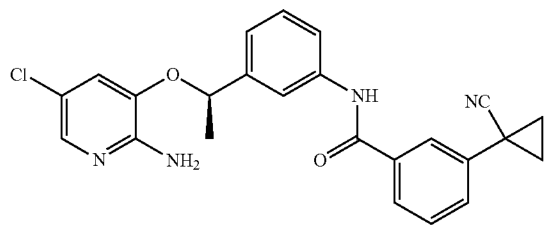 [SMILES: C[C@@H](Oc1cc(Cl)cnc1N)c1cccc(NC(=O)c2cccc(C3(C#N)CC3)c2)c1] | (R)-N-(3-(1-((2-amino-5-chloropyridin-3-yl)oxy)ethyl)-phenyl)-3-(1-cyanocyclopropyl)-benzamide | 433 |
| 114 | 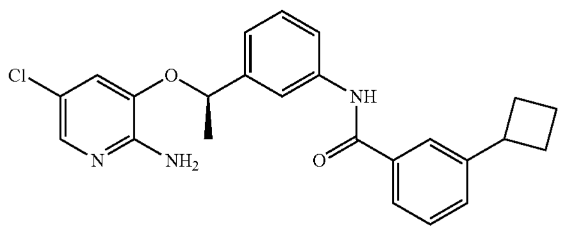 [SMILES: C[C@@H](Oc1cc(Cl)cnc1N)c1cccc(NC(=O)c2cccc(C3CCC3)c2)c1] | (R)-N-(3-(1-((2-amino-5-chloropyridin-3-yl)oxy)ethyl)-phenyl)-3-cyclobutylbenzamide | 422 |
| 115 | 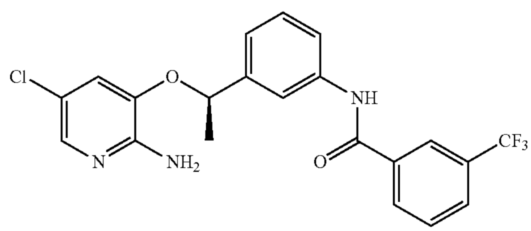 [SMILES: C[C@@H](Oc1cc(Cl)cnc1N)c1cccc(NC(=O)c2cccc(C(F)(F)F)c2)c1] | (R)-N-(3-(1-((2-amino-5-chloropyridin-3-yl)oxy)ethyl)-phenyl)-3-(trifluoromethyl)-benzamide | 436 |
| 116 | 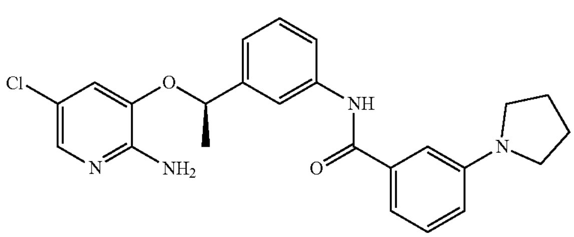 [SMILES: C[C@@H](Oc1cc(Cl)cnc1N)c1cccc(NC(=O)c2cccc(N3CCCC3)c2)c1] | (R)-N-(3-(1-((2-amino-5-chloropyridin-3-yl)oxy)ethyl)-phenyl)-3-(pyrrolidin-1-yl)-benzamide | 437 |
| 117 | 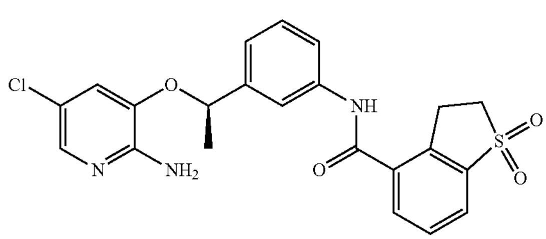 [SMILES: C[C@@H](Oc1cc(Cl)cnc1N)c1cccc(NC(=O)c2cccc3c2CCS3(=O)=O)c1] | (R)-N-(3-(1-((2-amino-5-chloropyridin-3-yl)oxy)ethyl)-phenyl)-2,3-dihydrobenzo[b]thiophene-4-carboxamide 1,1-dioxide | 458 |

TABLE 3-continued

| Comps. No. | Compound structure | Compound name | MS [M + 1] |
|---|---|---|---|
| 118 | 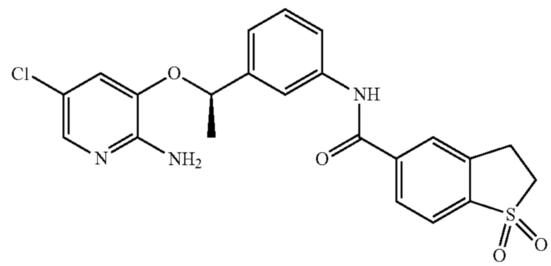 [SMILES: C[C@@H](Oc1cc(Cl)cnc1N)c1cccc(NC(=O)c2ccc3c(c2)CCS3(=O)=O)c1] | (R)-N-(3-(1-((2-amino-5-chloropyridin-3-yl)oxy)ethyl)-phenyl)-2,3-dihydrobenzo[b]thiophene-5-carboxamide1,1-dioxide | 458 |
| 119 | 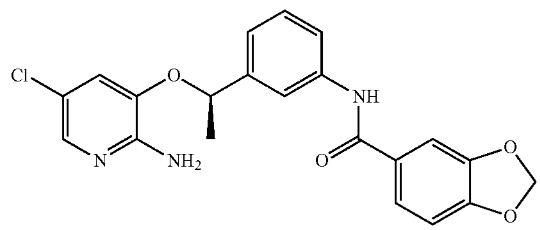 [SMILES: C[C@@H](Oc1cc(Cl)cnc1N)c1cccc(NC(=O)c2ccc3c(c2)OCO3)c1] | (R)-N-(3-(1-((2-amino-5-chloropyridin-3-yl)oxy)ethyl)-phenyl)benzo[d][1,3]dioxole-5-carboxamide | 412 |
| 120 | 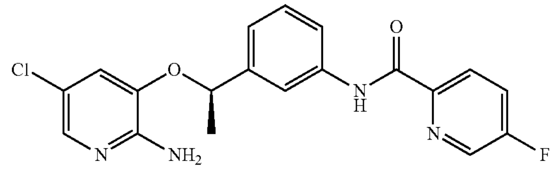 [SMILES: C[C@@H](Oc1cc(Cl)cnc1N)c1cccc(NC(=O)c2ccc(F)cn2)c1] | (R)-N-(3-(1-((2-amino-5-chloropyridin-3-yl)oxy)ethyl)-phenyl)-5-fluoropicolinamide | 387 |
| 121 | 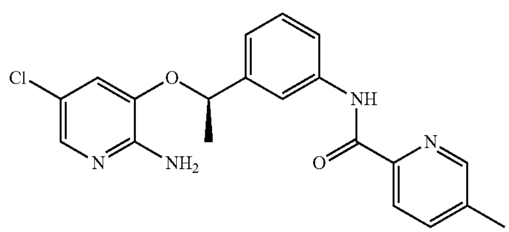 [SMILES: Cc1ccc(C(=O)Nc2cccc([C@@H](C)Oc3cc(Cl)cnc3N)c2)nc1] | (R)-N-(3-(1-((2-amino-5-chloropyridin-3-yl)oxy)ethyl)-phenyl)-5-methylpicolinamide | 383 |
| 122 | 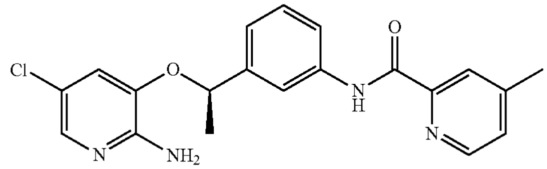 [SMILES: Cc1ccnc(C(=O)Nc2cccc([C@@H](C)Oc3cc(Cl)cnc3N)c2)c1] | (R)-N-(3-(1-((2-amino-5-chloropyridin-3-yl)oxy)ethyl)-phenyl)-4-methylpicolinamide | 383 |
| 123 | 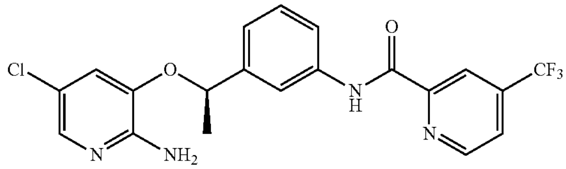 [SMILES: C[C@@H](Oc1cc(Cl)cnc1N)c1cccc(NC(=O)c2cc(C(F)(F)F)ccn2)c1] | (R)-N-(3-(1-((2-amino-5-chloropyridin-3-yl)oxy)ethyl)-phenyl)-4-(trifluoromethyl)-picolinamide | 437 |
| 124 | 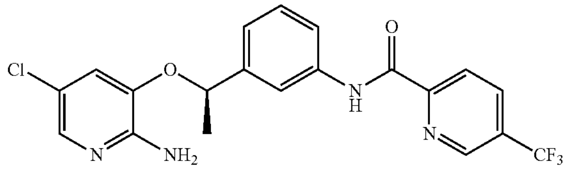 [SMILES: C[C@@H](Oc1cc(Cl)cnc1N)c1cccc(NC(=O)c2ccc(C(F)(F)F)cn2)c1] | (R)-N-(3-(1-((2-amino-5-chloropyridin-3-yl)oxy)ethyl)-phenyl)-5-(trifluoromethyl)-picolinamide | 437 |

TABLE 3-continued

| Comps. No. | Compound structure | Compound name | MS [M + 1] |
|---|---|---|---|
| 125 | 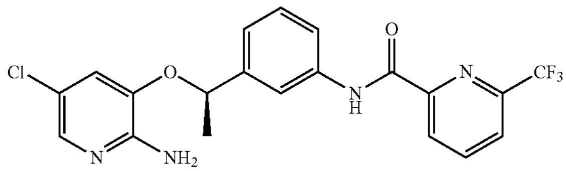 [SMILES: C[C@@H](Oc1cc(Cl)cnc1N)c1cccc(NC(=O)c2cccc(C(F)(F)F)n2)c1] | (R)-N-(3-(1-((2-amino-5-chloropyridin-3-yl)oxy)ethyl)-phenyl)-6-(trifluoromethyl)-picolinamide | 437 |
| 126 | 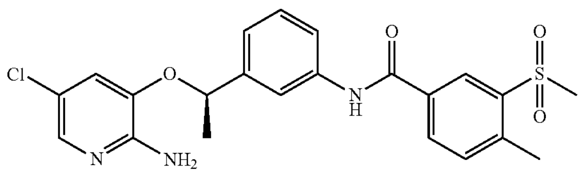 [SMILES: Cc1ccc(C(=O)Nc2cccc([C@@H](C)Oc3cc(Cl)cnc3N)c2)cc1S(C)(=O)=O] | (R)-N-(3-(1-((2-amino-5-chloropyridin-3-yl)oxy)ethyl)-phenyl)-4-methyl-3-(methylsulfonyl)benzamide | 460 |
| 127 | 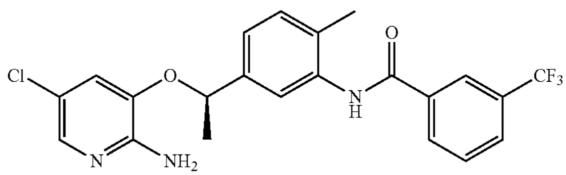 [SMILES: Cc1ccc([C@@H](C)Oc2cc(Cl)cnc2N)cc1NC(=O)c1cccc(C(F)(F)F)c1] | (R)-N-(5-(1-((2-amino-5-chloropyridin-3-yl)oxy)ethyl)-2-methylphenyl)-3-(trifluoromethyl)benzamide | 450 |
| 128 | 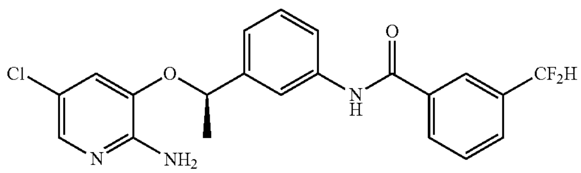 [SMILES: C[C@@H](Oc1cc(Cl)cnc1N)c1cccc(NC(=O)c2cccc(C(F)F)c2)c1] | (R)-N-(3-(1-((2-amino-5-chloropyridin-3-yl)oxy)ethyl)-phenyl)-3-(difluoromethyl)benzamide | 418 |
| 129 | 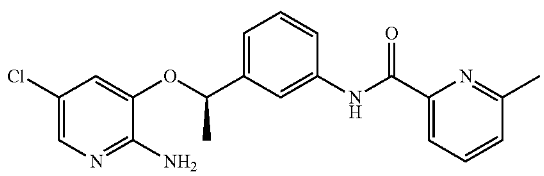 [SMILES: Cc1cccc(C(=O)Nc2cccc([C@@H](C)Oc3cc(Cl)cnc3N)c2)n1] | (R)-N-(3-(1-((2-amino-5-chloropyridin-3-yl)oxy)ethyl)-phenyl)-6-methylpicolinamide | 383 |
| 130 | 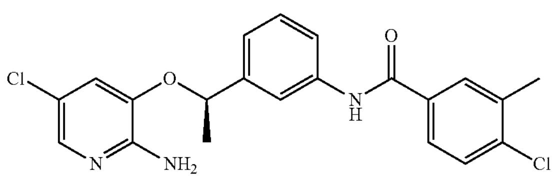 [SMILES: Cc1cc(C(=O)Nc2cccc([C@@H](C)Oc3cc(Cl)cnc3N)c2)ccc1Cl] | (R)-N-(3-(1-((2-amino-5-chloropyridin-3-yl)oxy)ethyl)-phenyl)-4-chloro-3-methylbenzamide | 416 |
| 131 | 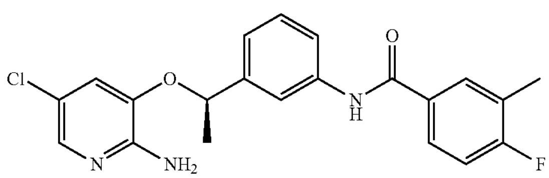 [SMILES: Cc1cc(C(=O)Nc2cccc([C@@H](C)Oc3cc(Cl)cnc3N)c2)ccc1F] | (R)-N-(3-(1-((2-amino-5-chloropyridin-3-yl)oxy)ethyl)-phenyl)-4-fluoro-3-methylbenzamide | 400 |
| 132 | 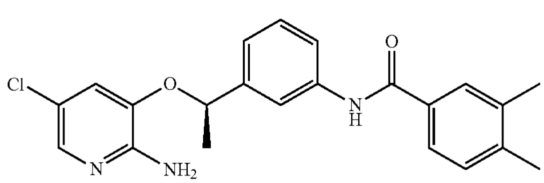 [SMILES: Cc1ccc(C(=O)Nc2cccc([C@@H](C)Oc3cc(Cl)cnc3N)c2)cc1C] | (R)-N-(3-(1-((2-amino-5-chloropyridin-3-yl)oxy)ethyl)-phenyl)-3,4-dimethylbenzamide | 396 |

TABLE 3-continued

| Comps. No. | Compound structure | Compound name | MS [M + 1] |
|---|---|---|---|
| 133 | 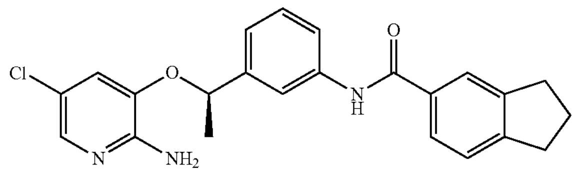 [SMILES: C[C@@H](Oc1cc(Cl)cnc1N)c1cccc(NC(=O)c2ccc3c(c2)CCC3)c1] | (R)-N-(3-(1-((2-amino-5-chloropyridin-3-yl)oxy)ethyl)-phenyl)-2,3-dihydro-1H-indene-5-carboxamide | 408 |
| 134 | 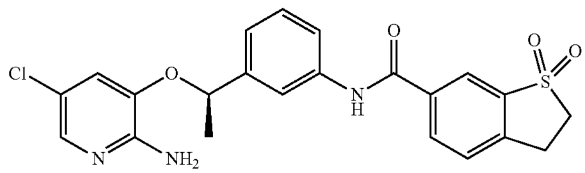 [SMILES: C[C@@H](Oc1cc(Cl)cnc1N)c1cccc(NC(=O)c2ccc3c(c2)S(=O)(=O)CC3)c1] | (R)-N-(3-(1-((2-amino-5-chloropyridin-3-yl)oxy)ethyl)-phenyl)-2,3-dihydrobenzo[b]thiophene-6-carboxamide 1,1-dioxide | 458 |
| 135 | 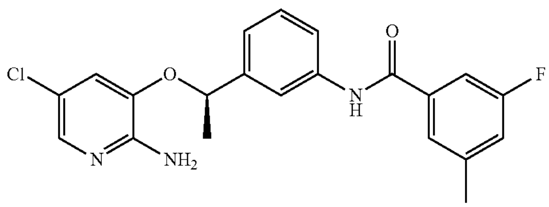 [SMILES: Cc1cc(F)cc(C(=O)Nc2cccc([C@@H](C)Oc3cc(Cl)cnc3N)c2)c1] | (R)-N-(3-(1-((2-amino-5-chloropyridin-3-yl)oxy)ethyl)-phenyl)-3-fluoro-5-methylbenzamide | 400 |
| 136 | 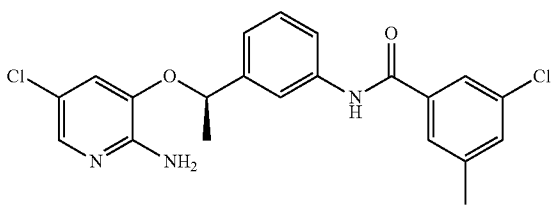 [SMILES: Cc1cc(Cl)cc(C(=O)Nc2cccc([C@@H](C)Oc3cc(Cl)cnc3N)c2)c1] | (R)-N-(3-(1-((2-amino-5-chloropyridin-3-yl)oxy)ethyl)-phenyl)-3-chloro-5-methylbenzamide | 416 |
| 137 | 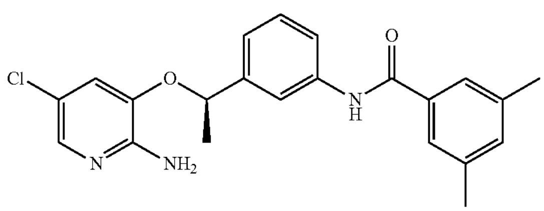 [SMILES: Cc1cc(C)cc(C(=O)Nc2cccc([C@@H](C)Oc3cc(Cl)cnc3N)c2)c1] | (R)-N-(3-(1-((2-amino-5-chloropyridin-3-yl)oxy)ethyl)-phenyl)-3,5-dimethylbenzamide | 396 |
| 138 | 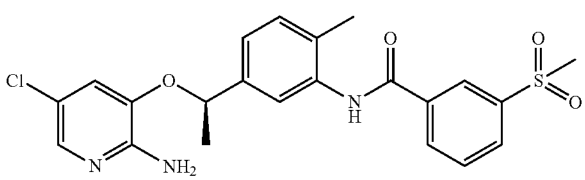 [SMILES: Cc1ccc([C@@H](C)Oc2cc(Cl)cnc2N)cc1NC(=O)c1cccc(S(C)(=O)=O)c1] | (R)-N-(3-(1-((2-amino-5-chloropyridin-3-yl)oxy)ethyl)-2-methylphenyl)-3-(methylsulfonyl)benzamide | 460 |
| 139 | 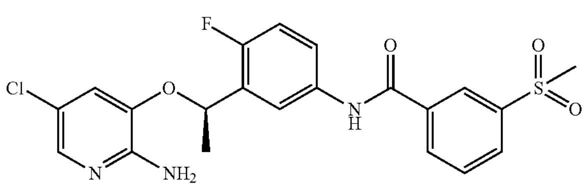 [SMILES: C[C@@H](Oc1cc(Cl)cnc1N)c1cc(NC(=O)c2cccc(S(C)(=O)=O)c2)ccc1F] | (R)-N-(3-(1-((2-amino-5-chloropyridin-3-yl)oxy)ethyl)-4-fluorophenyl)-3-(methylsulfonyl)benzamide | 464 |
| 140 | 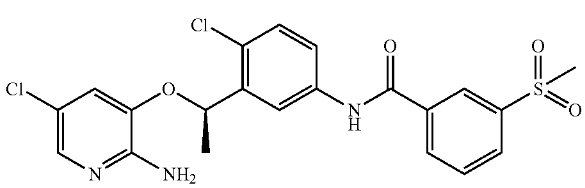 | (R)-N-(3-(1-((2-amino-5-chloropyridin-3-yl)oxy)ethyl)-4-chlorophenyl)-3-(methylsulfonyl)benzamide | 480 |

TABLE 3-continued

| Comps. No. | Compound structure | Compound name | MS [M + 1] |
|---|---|---|---|
| 141 | 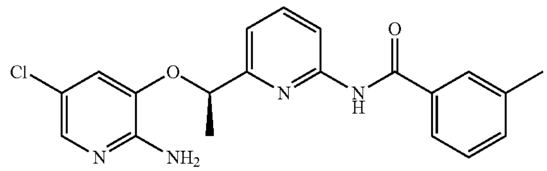 [SMILES: Cc1cccc(C(=O)Nc2cccc([C@@H](C)Oc3cc(Cl)cnc3N)n2)c1] | (R)-N-(6-(1-((2-amino-5-chloropyridin-3-yl)oxy)ethyl)-pyridin-2-yl)-3-methylbenzamide | 383 |
| 142 | 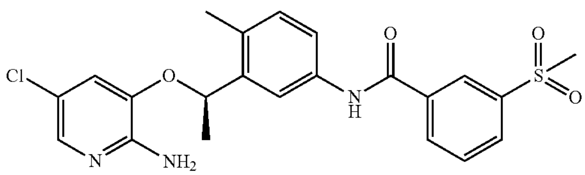 [SMILES: Cc1ccc(NC(=O)c2cccc(S(C)(=O)=O)c2)cc1[C@@H](C)Oc1cc(Cl)cnc1N] | (R)-N-(3-(1-((2-amino-5-chloropyridin-3-yl)oxy)ethyl)-4-methylphenyl)-3-(methylsulfonyl)benzamide | 460 |
| 143 | 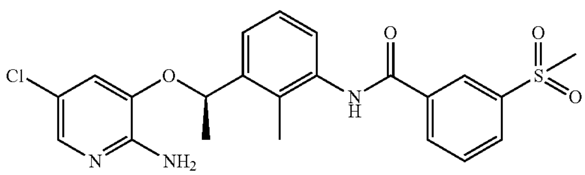 [SMILES: Cc1c(NC(=O)c2cccc(S(C)(=O)=O)c2)cccc1[C@@H](C)Oc1cc(Cl)cnc1N] | (R)-N-(3-(1-((2-amino-5-chloropyridin-3-yl)oxy)ethyl)-2-methylphenyl)-3-(methylsulfonyl)benzamide | 460 |
| 144 | 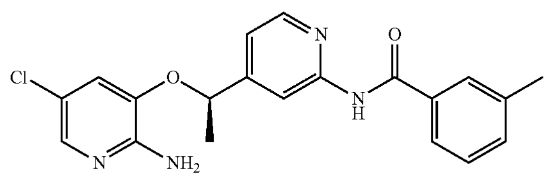 [SMILES: Cc1cccc(C(=O)Nc2cc([C@@H](C)Oc3cc(Cl)cnc3N)ccn2)c1] | (R)-N-(4-(1-((2-amino-5-chloropyridin-3-yl)oxy)ethyl)-pyridin-2-yl)-3-methylbenzamide | 383 |
| 145 | 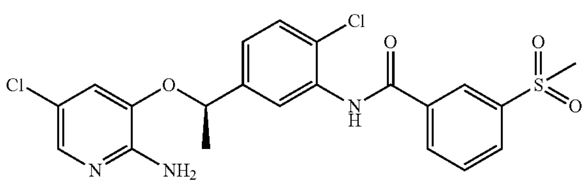 [SMILES: C[C@@H](Oc1cc(Cl)cnc1N)c1ccc(Cl)c(NC(=O)c2cccc(S(C)(=O)=O)c2)c1] | (R)-N-(5-(1-((2-amino-5-chloropyridin-3-yl)oxy)ethyl)-orophenyl)-3-(methylsulfonyl)benzamide | 480 |
| 146 | 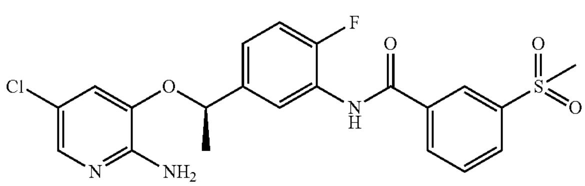 | (R)-N-(5-(1-((2-amino-5-chloropyridin-3-yl)oxy)ethyl)-2-chlorophenyl)-3-(methylsulfonyl)-benzamide | 464 |
| 147 | 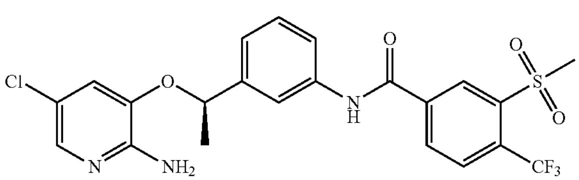 [SMILES: C[C@@H](Oc1cc(Cl)cnc1N)c1cccc(NC(=O)c2ccc(C(F)(F)F)c(S(C)(=O)=O)c2)c1] | (R)-N-(3-(1-((2-amino-5-chloropyridin-3-yl)oxy)ethyl)-phenyl)-3-(methylsulfonyl)-4-(trifluoromethyl)benzamide | 514 |
| 148 | 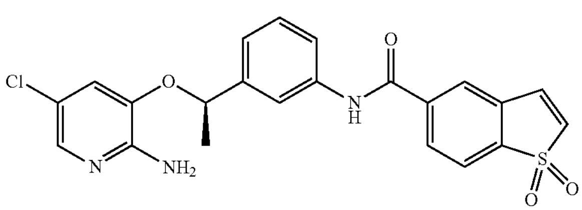 [SMILES: C[C@@H](Oc1cc(Cl)cnc1N)c1cccc(NC(=O)c2ccc3c(c2)C=CS3(=O)=O)c1] | (R)-N-(3-(1-((2-amino-5-chloropyridin-3-yl)oxy)ethyl)-phenyl)benzo[b]thiophene-5-carboxamide 1,1-dioxide | 456 |

TABLE 3-continued

| Comps. No. | Compound structure | Compound name | MS [M + 1] |
|---|---|---|---|
| 149 | 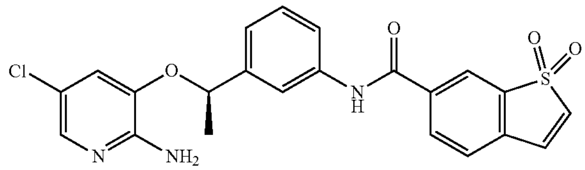 [SMILES: C[C@@H](Oc1cc(Cl)cnc1N)c1cccc(NC(=O)c2ccc3c(c2)S(=O)(=O)C=C3)c1] | (R)-N-(3-(1-((2-amino-5-chloropyridin-3-yl)oxy)ethyl)-phenyl)benzo[b]thiophene-6-carboxamide 1,1-dioxide | 456 |
| 150 | 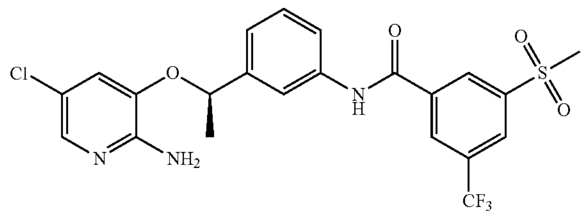 [SMILES: C[C@@H](Oc1cc(Cl)cnc1N)c1cccc(NC(=O)c2cc(C(F)(F)F)cc(S(C)(=O)=O)c2)c1] | (R)-N-(3-(1-((2-amino-5-chloropyridin-3-yl)oxy)ethyl)-phenyl)-3-(methylsulfonyl)-5-(trifluoromethyl)benzamide | 514 |
| 151 | 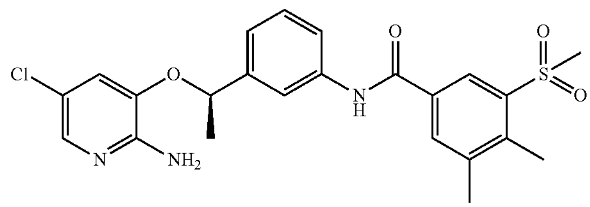 [SMILES: Cc1cc(C(=O)Nc2cccc([C@@H](C)Oc3cc(Cl)cnc3N)c2)cc(S(C)(=O)=O)c1C] | (R)-N-(3-(1-((2-amino-5-chloropyridin-3-yl)oxy)ethyl)-phenyl)-3,4-dimethyl-5-(methylsulfonyl)benzamide | 474 |
| 152 | 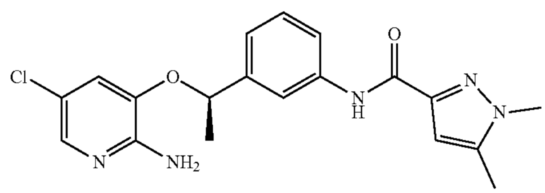 [SMILES: Cc1cc(C(=O)Nc2cccc([C@@H](C)Oc3cc(Cl)cnc3N)c2)nn1C] | (R)-N-(3-(1-((2-amino-5-chloropyridin-3-yl)oxy)ethyl)-phenyl)-1,5-dimethyl-1H-pyrazole-3-carboxamide | 386 |
| 153 | 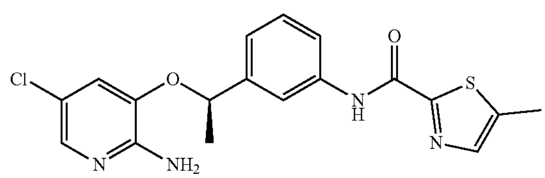 [SMILES: Cc1cnc(C(=O)Nc2cccc([C@@H](C)Oc3cc(Cl)cnc3N)c2)s1] | (R)-N-(3-(1-((2-amino-5-chloropyridin-3-yl)oxy)ethyl)-phenyl)-5-methylthiazole-2-carboxamide | 389 |
| 154 | 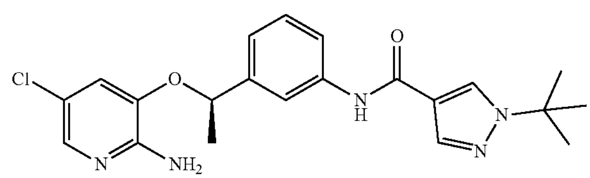 [SMILES: C[C@@H](Oc1cc(Cl)cnc1N)c1cccc(NC(=O)c2cnn(C(C)(C)C)c2)c1] | (R)-N-(3-(1-((2-amino-5-chloropyridin-3-yl)oxy)ethyl)-phenyl)-1-(tert-butyl)-1H-pyrazole-4-carboxamide | 414 |
| 155 | 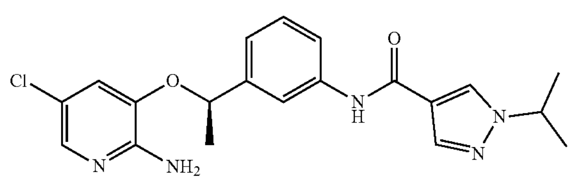 [SMILES: CC(C)n1cc(C(=O)Nc2cccc([C@@H](C)Oc3cc(Cl)cnc3N)c2)cn1] | (R)-N-(3-(1-((2-amino-5-chloropyridin-3-yl)oxy)ethyl)-phenyl)-1-isopropyl-1H-pyrazole-4-carboxamide | 400 |
| 156 | 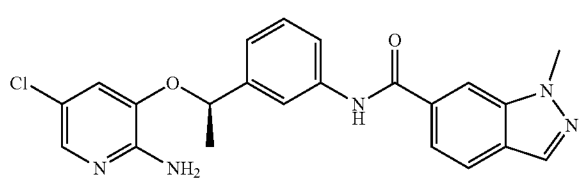 [SMILES: C[C@@H](Oc1cc(Cl)cnc1N)c1cccc(NC(=O)c2ccc3cnn(C)c3c2)c1] | (R)-N-(3-(1-((2-amino-5-chloropyridin-3-yl)oxy)ethyl)-phenyl)-1-methyl-1H-indazole-6-carboxamide | 422 |

TABLE 3-continued

| Comps. No. | Compound structure | Compound name | MS [M + 1] |
|---|---|---|---|
| 157 | 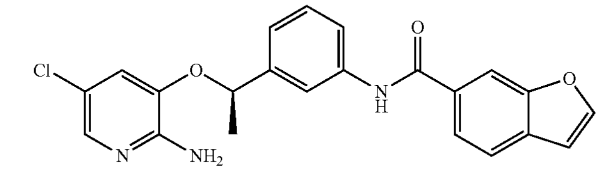 [SMILES: C[C@@H](Oc1cc(Cl)cnc1N)c1cccc(NC(=O)c2ccc3ccoc3c2)c1] | (R)-N-(3-(1-((2-amino-5-chloropyridin-3-yl)oxy)ethyl)-phenyl)benzofuran-6-carboxamide | 408 |
| 158 | 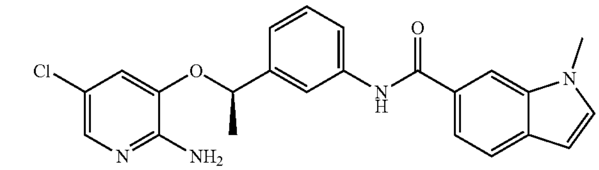 | (R)-N-(3-(1-((2-amino-5-chloropyridin-3-yl)oxy)ethyl)-phenyl)-1-methyl-1H-indole-6-carboxamide | 421 |
| 159 | 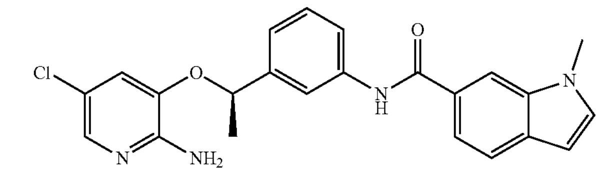 | (R)-N-(3-(1-((2-amino-5-chloropyridin-3-yl)oxy)ethyl)-phenyl)-5-(tert-butyl)isoxazole-3-carboxamide | 415 |
| 160 | 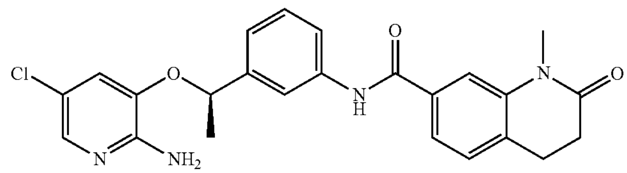 [SMILES: C[C@@H](Oc1cc(Cl)cnc1N)c1cccc(NC(=O)c2ccc3c(c2)N(C)C(=O)CC3)c1] | (R)-N-(3-(1-((2-amino-5-chloropyridin-3-yl)oxy)ethyl)-phenyl)-1-methyl-2-oxo-1,2,3,4-tetrahydroquinoline-7-carboxamide | 451 |
| 161 | 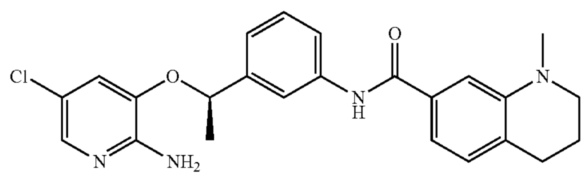 [SMILES: C[C@@H](Oc1cc(Cl)cnc1N)c1cccc(NC(=O)c2ccc3c(c2)N(C)CCC3)c1] | (R)-N-(3-(1-((2-amino-5-chloropyridin-3-yl)oxy)ethyl)-phenyl)-1-methyl-1,2,3,4-tetrahydroquinoline-7-carboxamide | 437 |
| 162 | 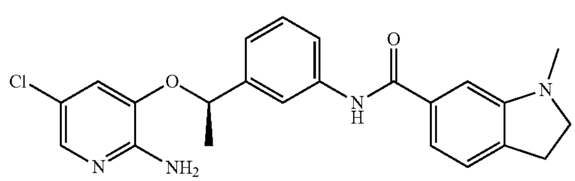 [SMILES: C[C@@H](Oc1cc(Cl)cnc1N)c1cccc(NC(=O)c2ccc3c(c2)N(C)CC3)c1] | (R)-N-(3-(1-((2-amino-5-chloropyridin-3-yl)oxy)ethyl)-phenyl)-1-methylindoline-6-carboxamide | 423 |
| 163 | 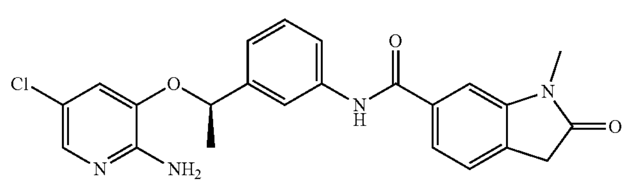 [SMILES: C[C@@H](Oc1cc(Cl)cnc1N)c1cccc(NC(=O)c2ccc3c(c2)N(C)C(=O)C3)c1] | (R)-N-(3-(1-((2-amino-5-chloropyridin-3-yl)oxy)ethyl)-phenyl)-1-methyl-2-oxoindoline-6-carboxamide | 437 |
| 164 | 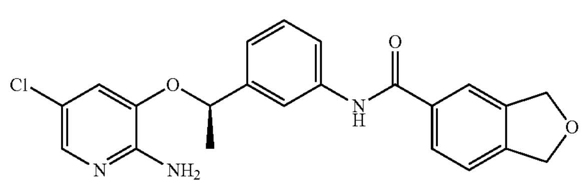 [SMILES: C[C@@H](Oc1cc(Cl)cnc1N)c1cccc(NC(=O)c2ccc3c(c2)COC3)c1] | (R)-N-(3-(1-((2-amino-5-chloropyridin-3-yl)oxy)ethyl)-phenyl)-1,3-dihydroisobenzofuran-5-carboxamide | 410 |

Example 7

Synthesis of Compounds 168-195

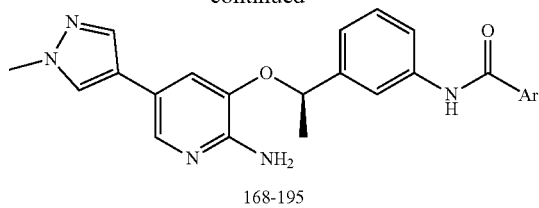

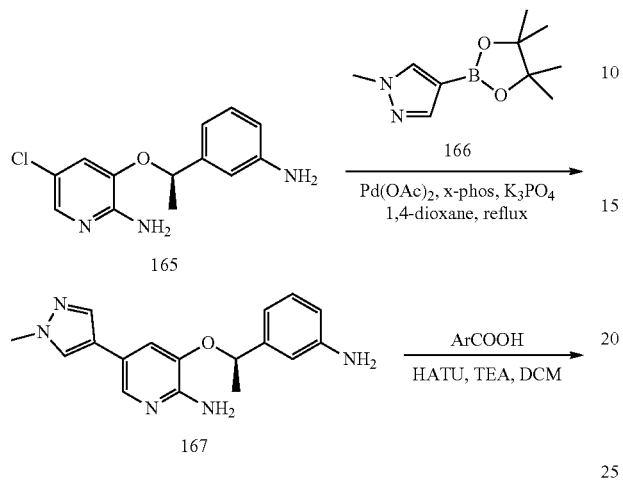

Step 1: To the solution of 165 (2.64 g, 10.0 mmol), 166 (3.12 g, 15.0 mmol) and x-phos (954 mg, 2.0 mmol) in dioxane (100 mL) was added the solution of K₃PO₄ (6.57 g, 30.0 mmol) in water (10 mL). The resulting mixture was degassed with nitrogen for 3 times, and palladium acetate (225 mg, 1.0 mmol) was added, then degassed again. The reaction mixture was then heated at 110 TC for 24 h, cooled to room temperature, poured into 13° 0 brine and extracted with EA twice. The combined organic layers was washed with brine, dried, filtered and concentrated. The crude product was purified by column chromatography to give brown oil.

Step 2: To the solution of 167 (62 mg, 0.2 mmol), ArCOOH (1.2 eq), HATU (1.5 eq) in DCM (2 mL) was added TEA (3.0 eq). The reaction mixture was stirred at room temperature for 16 h. The crude product was purified by column chromatography or PTLC.

TABLE 4

| Comps. No. | Compound structure | Compound name | MS [M + 1] |
|---|---|---|---|
| 168 | 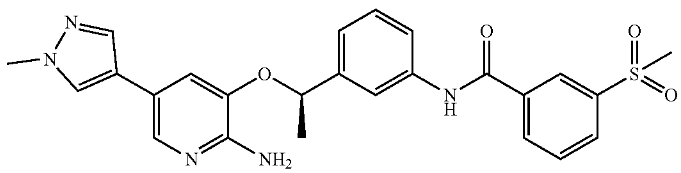 | (R)-N-(3-(1-((2-amino-5-(1-methyl-1H-pyrazol-4-yl)pyridin-3-yl)oxy)ethyl)phenyl)-3-(methylsulfonyl)benzamide | 492 |
| 169 | 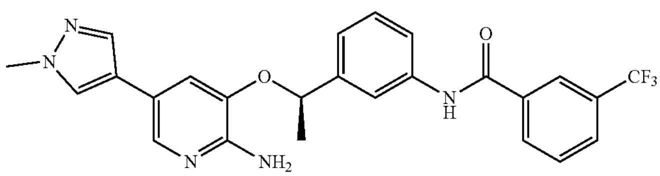 [SMILES: C[C@@H](Oc1cc(-c2cnn(C)c2)cnc1N)c1cccc(NC(=O)c2cccc(C(F)(F)F)c2)c1] | (R)-N-(3-(1-((2-amino-5-(1-methyl-1H-pyrazol-4-yl)pyridin-3-yl)oxy)ethyl)phenyl)-3-(trifluoromethyl)benzamide | 482 |
| 170 | 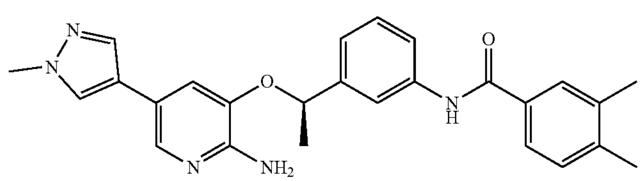 | (R)-N-(3-(1-((2-amino-5-(1-methyl-1H-pyrazol-4-yl)pyridin-3-yl)oxy)ethyl)phenyl)-3,4-dimethyl benzamide | 442 |
| 171 | 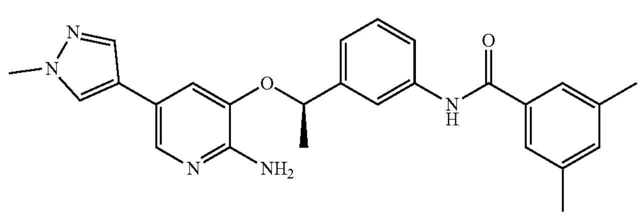 | (R)-N-(3-(1-((2-amino-5-(1-methyl-1H-pyrazol-4-yl)pyridin-3-yl)oxy)ethyl)phenyl)-3,5-dimethyl benzamide | 442 |

TABLE 4-continued

| Comps. No. | Compound structure | Compound name | MS [M + 1] |
|---|---|---|---|
| 172 | 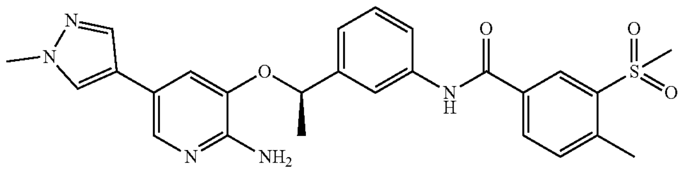 | (R)-N-(3-(1-((2-amino-5-(1-methyl-1H-pyrazol-4-yl)pyridin-3-yl)oxy)ethyl)phenyl)-4-methyl-3-(methylsulfonyl)benzamide | 506 |
| 173 | 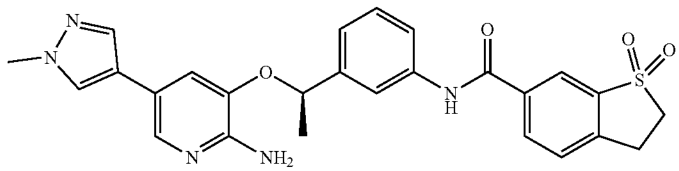 [SMILES: C[C@@H](Oc1cc(-c2cnn(C)c2)cnc1N)c1cccc(NC(=O)c2ccc3c(c2)S(=O)(=O)CC3)c1] | (R)-N-(3-(1-((2-amino-5-(1-methyl-1H-pyrazol-4-yl)pyridin-3-yl)oxy)ethyl)phenyl)-2,3-dihydrobenzo[b]thiophene-6-carboxamide 1,1-dioxide | 504 |
| 174 | 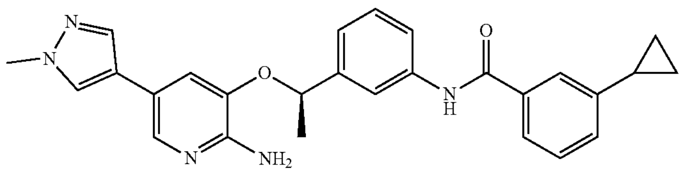 [SMILES: C[C@@H](Oc1cc(-c2cnn(C)c2)cnc1N)c1cccc(NC(=O)c2cccc(C3CC3)c2)c1] | (R)-N-(3-(1-((2-amino-5-(1-methyl-1H-pyrazol-4-yl)pyridin-3-yl)oxy)ethyl)phenyl)-cyclopropylbenzamide | 454 |
| 175 | 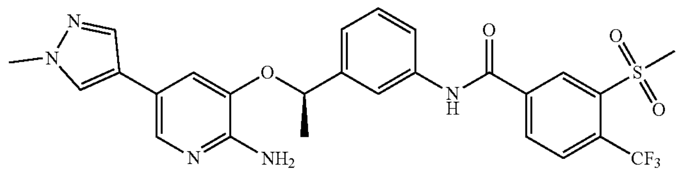 | (R)-N-(3-(1-((2-amino-5-(1-methyl-1H-pyrazol-4-yl)pyridin-3-yl)oxy)ethyl)phenyl)-3-(methylsulfonyl)-4-(trifluoromethyl)benzamide | 560 |
| 176 | 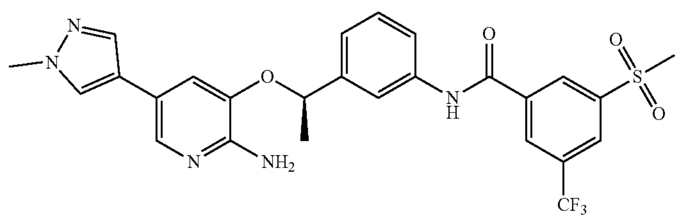 | (R)-N-(3-(1-((2-amino-5-(1-methyl-1H-pyrazol-4-yl)pyridin-3-yl)oxy)ethyl)phenyl)-3-(methylsulfonyl)-5-(trifluoromethyl)benzamide | 560 |
| 177 | 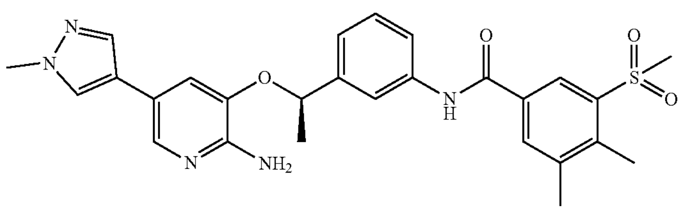 | (R)-N-(3-(1-((2-amino-5-(1-methyl-1H-pyrazol-4-yl)pyridin-3-yl)oxy)ethyl)phenyl)-3,4-dimethyl-5-(methylsulfonyl)benzamide | 520 |
| 178 | 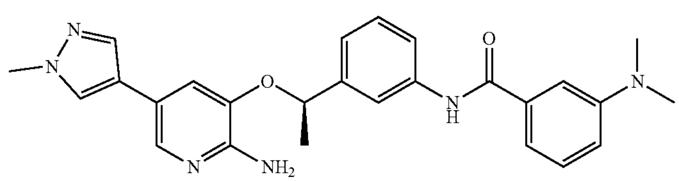 | (R)-N-(3-(1-((2-amino-5-(1-methyl-1H-pyrazol-4-yl)pyridin-3-yl)oxy)ethyl)phenyl)-3-(dimethylamino)benzamide | 457 |
| 179 | 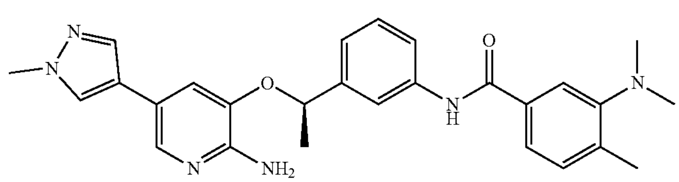 | (R)-N-(3-(1-((2-amino-5-(1-methyl-1H-pyrazol-4-yl)pyridin-3-yl)oxy)ethyl)phenyl)-3-(dimethylamino)-4-methylbenzamide | 471 |

TABLE 4-continued

| Comps. No. | Compound structure | Compound name | MS [M + 1] |
|---|---|---|---|
| 180 | 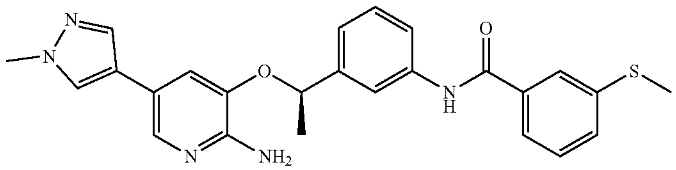 | (R)-N-(3-(1-((2-amino-5-(1-methyl-1H-pyrazol-4-yl)pyridin-3-yl)oxy)ethyl)phenyl)-3-(methylthio)benzamide | 460 |
| 181 | 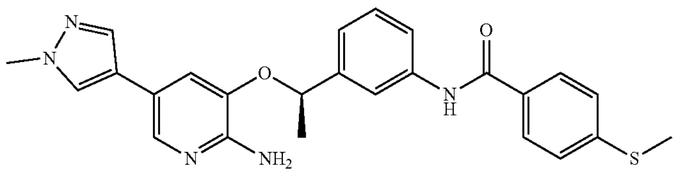 | (R)-N-(3-(1-((2-amino-5-(1-methyl-1H-pyrazol-4-yl)pyridin-3-yl)oxy)ethyl)phenyl)-4-(methylthio)benzamide | 460 |
| 182 | 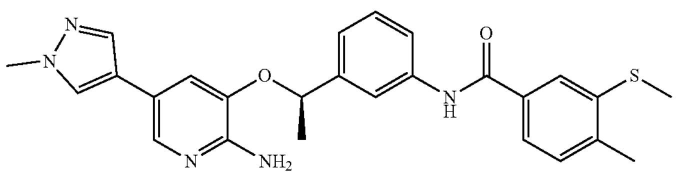 | (R)-N-(3-(1-((2-amino-5-(1-methyl-1H-pyrazol-4-yl)pyridin-3-yl)oxy)ethyl)phenyl)-4-methyl-3-(methylthio)benzamide | 474 |
| 183 | 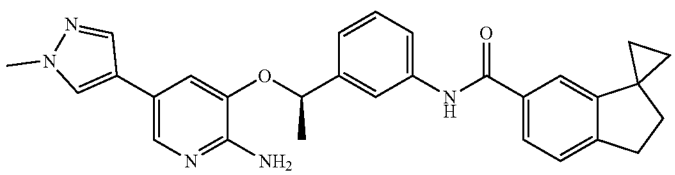 [SMILES: C[C@@H](Oc1cc(-c2cnn(C)c2)cnc1N)c1cccc(NC(=O)c2ccc3c(c2)C2(CC3)CC2)c1] | (R)-N-(3-(1-((2-amino-5-(1-methyl-1H-pyrazol-4-yl)pyridin-3-yl)oxy)ethyl)phenyl)-2',3'-dihydrospiro[cyclopropane-1,1'-indene]-6'-carboxamide | 480 |
| 184 | 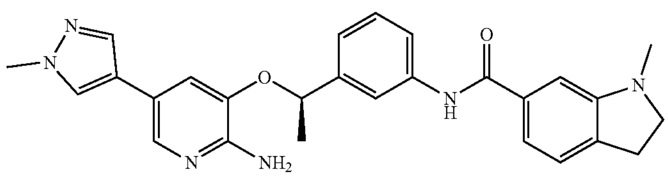 [SMILES: C[C@@H](Oc1cc(-c2cnn(C)c2)cnc1N)c1cccc(NC(=O)c2ccc3c(c2)N(C)CC3)c1] | (R)-N-(3-(1-((2-amino-5-(1-methyl-1H-pyrazol-4-yl)pyridin-3-yl)oxy)ethyl)phenyl)-1-methylindoline-6-carboxamide | 469 |
| 185 | 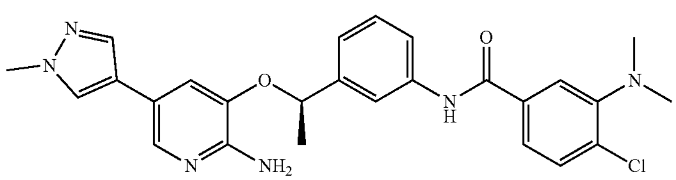 | (R)-N-(3-(1-((2-amino-5-(1-methyl-1H-pyrazol-4-yl)pyridin-3-yl)oxy)ethyl)phenyl)-4-chloro-3-(dimethylamino)benzamide | 491 |
| 186 | 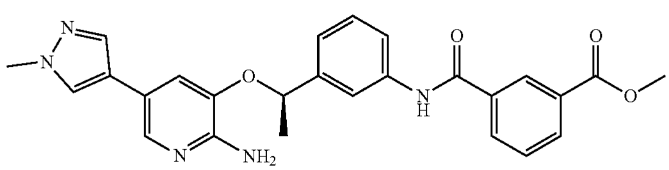 | methyl (R)-3-((3-(1-((2-amino-5-(1-methyl-1H-pyrazol-4-yl)pyridin-3-yl)oxy)ethyl)phenyl)carbamoyl)-benzoate | 472 |
| 187 | 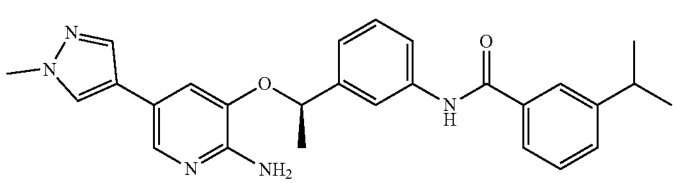 [SMILES: CC(C)c1cccc(C(=O)Nc2cccc([C@@H](C)Oc3cc(-c4cnn(C)c4)cnc3N)c2)c1] | (R)-N-(3-(1-((2-amino-5-(1-methyl-1H-pyrazol-4-yl)pyridin-3-yl)oxy)ethyl)phenyl)-3-isopropylbenzamide | 456 |

TABLE 4-continued

| Comps. No. | Compound structure | Compound name | MS [M + 1] |
|---|---|---|---|
| 188 | 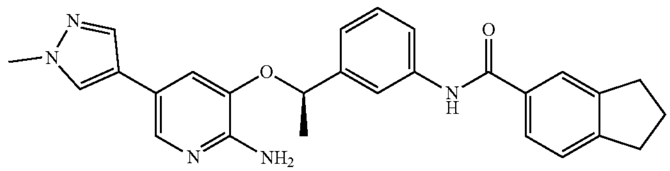 [SMILES: C[C@@H](Oc1cc(-c2cnn(C)c2)cnc1N)c1cccc(NC(=O)c2ccc3c(c2)CCC3)c1] | (R)-N-(3-(1-((2-amino-5-(1-methyl-1H-pyrazol-4-yl)pyridin-3-yl)oxy)ethyl)phenyl)-2,3-dihydro-1H-indene-5-carboxamide | 454 |
| 189 | 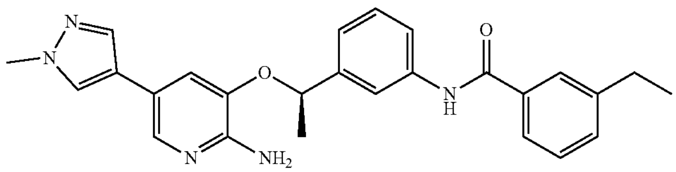 [SMILES: CCc1cccc(C(=O)Nc2cccc([C@@H](C)Oc3cc(-c4cnn(C)c4)cnc3N)c2)c1] | (R)-N-(3-(1-((2-amino-5-(1-methyl-1H-pyrazol-4-yl)pyridin-3-yl)oxy)ethyl)phenyl)-3-ethylbenzamide | 442 |
| 190 | 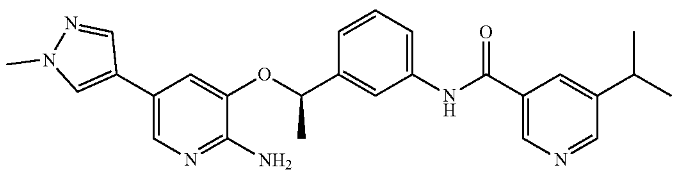 [SMILES: CC(C)c1cncc(C(=O)Nc2cccc([C@@H](C)Oc3cc(-c4cnn(C)c4)cnc3N)c2)c1] | (R)-N-(3-(1-((2-amino-5-(1-methyl-1H-pyrazol-4-yl)pyridin-3-yl)oxy)ethyl)phenyl)-5-isopropylnicotinamide | 457 |
| 191 | 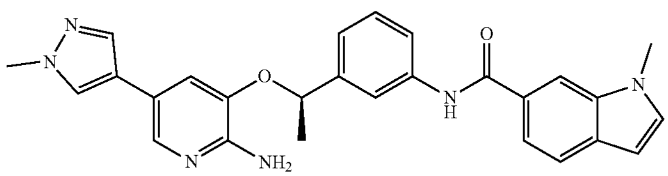 [SMILES: C[C@@H](Oc1cc(-c2cnn(C)c2)cnc1N)c1cccc(NC(=O)c2ccc3ccn(C)c3c2)c1] | (R)-N-(3-(1-((2-amino-5-(1-methyl-1H-pyrazol-4-yl)pyridin-3-yl)oxy)ethyl)phenyl)-1-methyl-1H-indole-6-carboxamide | 467 |
| 192 | 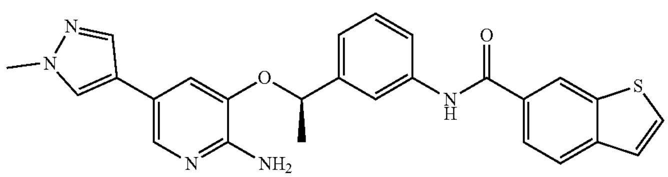 [SMILES: C[C@@H](Oc1cc(-c2cnn(C)c2)cnc1N)c1cccc(NC(=O)c2ccc3ccsc3c2)c1] | (R)-N-(3-(1-((2-amino-5-(1-methyl-1H-pyrazol-4-yl)pyridin-3-yl)oxy)ethyl)phenyl)benzo[b]-thiophene-6-carboxamide | 470 |
| 193 | 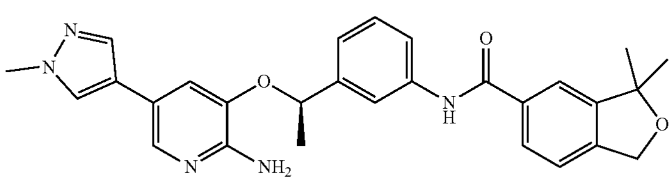 | (R)-N-(3-(1-((2-amino-5-(1-methyl-1H-pyrazol-4-yl)pyridin-3-yl)oxy)ethyl)phenyl)-3,3-dimethyl-1,3-dihydroisobenzofuran-5-carboxamide | 484 |
| 194 | 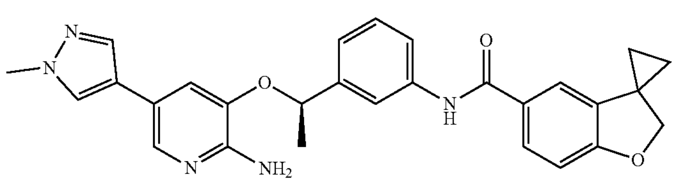 [SMILES: C[C@@H](Oc1cc(-c2cnn(C)c2)cnc1N)c1cccc(NC(=O)c2ccc3c(c2)C2(CC2)CO3)c1] | (R)-N-(3-(1-((2-amino-5-(1-methyl-1H-pyrazol-4-yl)pyridin-3-yl)oxy)ethyl)phenyl)-2H-spiro[benzofuran-3,1'-cyclopropane]-5-carboxamide | 482 |
| 195 | 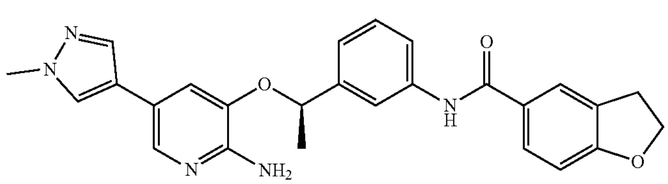 [SMILES: C[C@@H](Oc1cc(-c2cnn(C)c2)cnc1N)c1cccc(NC(=O)c2ccc3c(c2)CCO3)c1] | (R)-N-(3-(1-((2-amino-5-(1-methyl-1H-pyrazol-4-yl)pyridin-3-yl)oxy)ethyl)phenyl)-2,3-dihydrobenzofuran-5-carboxamide | 456 |

Example 8

Synthesis of Compounds 199-208 was Similar Procedures to that of Compounds 168-195

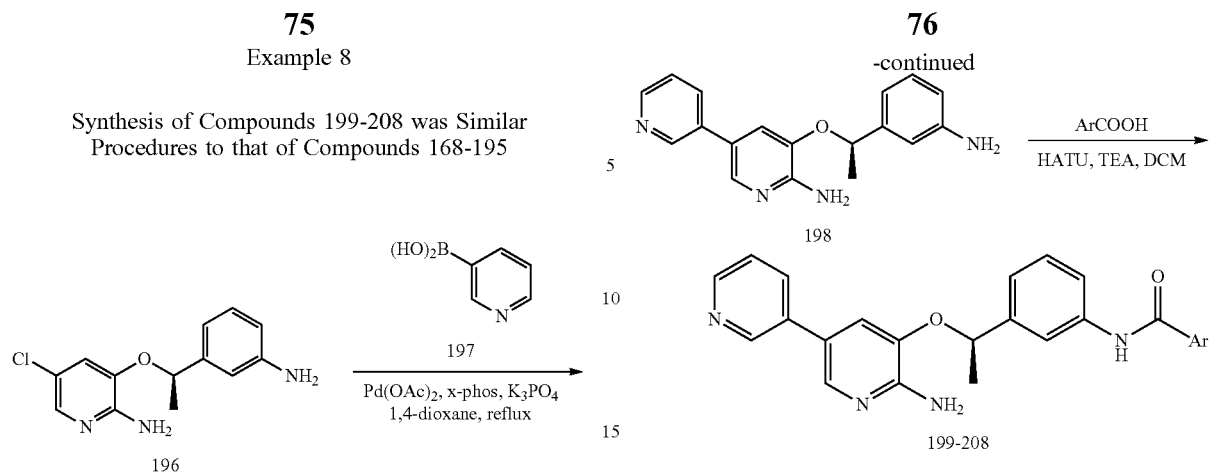

TABLE 5

| Comps. No. | Compound structure | Compound name | MS [M + 1] |
|---|---|---|---|
| 199 | 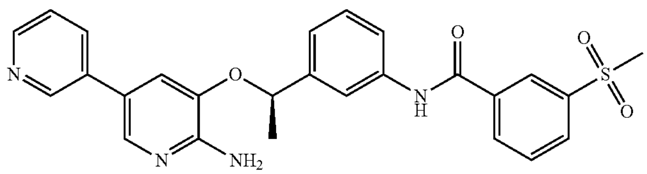 [SMILES: C[C@@H](Oc1cc(-c2cccnc2)cnc1N)c1cccc(NC(=O)c2cccc(S(C)(=O)=O)c2)c1] | (R)-N-(3-(1-((6-amino-[3,3'-bipyridin]-5-yl)oxy)ethyl)phenyl)-3-(methylsulfonyl)benzamide | 489 |
| 200 | 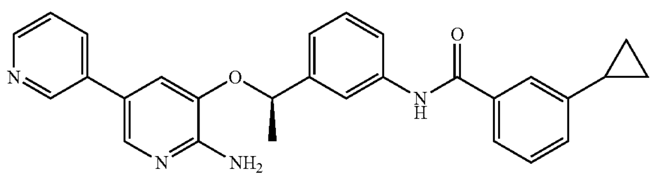 [SMILES: C[C@@H](Oc1cc(-c2cccnc2)cnc1N)c1cccc(NC(=O)c2cccc(C3CC3)c2)c1] | (R)-N-(3-(1-((6-amino-[3,3'-bipyridin]-5-yl)oxy)ethyl)phenyl)-3-cyclopropylbenzamide | 451 |
| 201 | 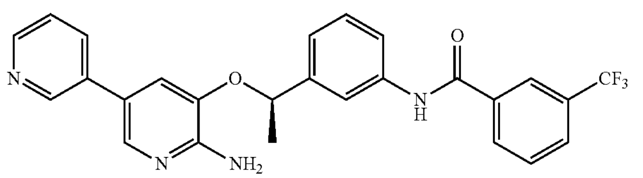 [SMILES: C[C@@H](Oc1cc(-c2cccnc2)cnc1N)c1cccc(NC(=O)c2cccc(C(F)(F)F)c2)c1] | (R)-N-(3-(1-((6-amino-[3,3'-bipyridin]-5-yl)oxy)ethyl)phenyl)-3-(trifluoromethyl)benzamide | 479 |
| 202 | 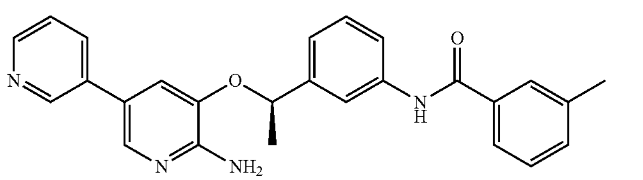 [SMILES: Cc1cccc(C(=O)Nc2cccc([C@@H](C)Oc3cc(-c4cccnc4)cnc3N)c2)c1] | (R)-N-(3-(1-((6-amino-[3,3'-bipyridin]-5-yl)oxy)ethyl)phenyl)-3-methylbenzamide | 425 |
| 203 | 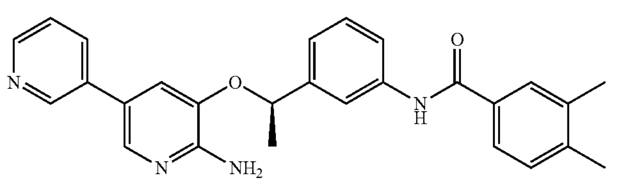 [SMILES: Cc1ccc(C(=O)Nc2cccc([C@@H](C)Oc3cc(-c4cccnc4)cnc3N)c2)cc1C] | (R)-N-(3-(1-((6-amino-[3,3'-bipyridin]-5-yl)oxy)ethyl)phenyl)-3,4-dimethylbenzamide | 439 |
| 204 | 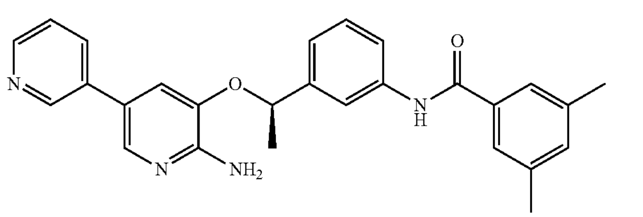 [SMILES: Cc1cc(C)cc(C(=O)Nc2cccc([C@@H](C)Oc3cc(-c4cccnc4)cnc3N)c2)c1] | (R)-N-(3-(1-((6-amino-[3,3'-bipyridin]-5-yl)oxy)ethyl)phenyl)-3,5-dimethylbenzamide | 439 |

TABLE 5-continued

| Comps. No. | Compound structure | Compound name | MS [M + 1] |
|---|---|---|---|
| 205 | 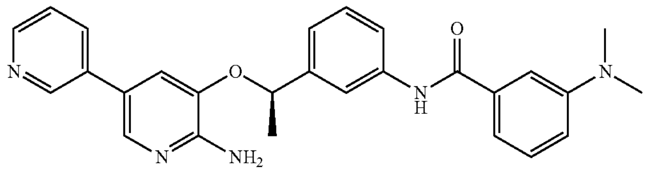 [SMILES: C[C@@H](Oc1cc(-c2cccnc2)cnc1N)c1cccc(NC(=O)c2cccc(N(C)C)c2)c1] | (R)-N-(3-(1-((6-amino-[3,3'-bipyridin]-5-yl)oxy)ethyl)phenyl)-3-(dimethylamino)benzamide | 454 |
| 206 | 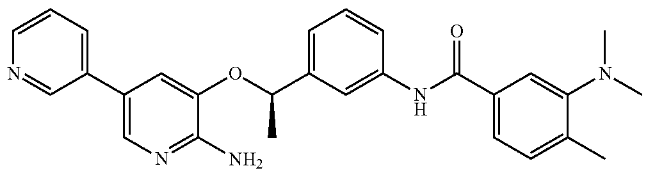 [SMILES: Cc1ccc(C(=O)Nc2cccc([C@@H](C)Oc3cc(-c4cccnc4)cnc3N)c2)cc1N(C)C] | (R)-N-(3-(1-((6-amino-[3,3'-bipyridin]-5-yl)oxy)ethyl)phenyl)-3-(dimethylamino)-4-methylbenzamide | 468 |
| 207 | 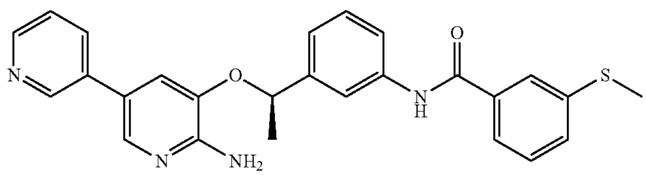 [SMILES: CSc1cccc(C(=O)Nc2cccc([C@@H](C)Oc3cc(-c4cccnc4)cnc3N)c2)c1] | (R)-N-(3-(1-((6-amino-[3,3'-bipyridin]-5-yl)oxy)ethyl)phenyl)-3-(methylthio)benzamide | 457 |
| 208 | 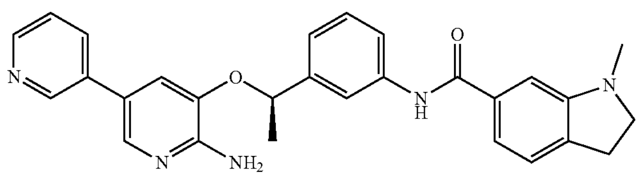 [SMILES: C[C@@H](Oc1cc(-c2cccnc2)cnc1N)c1cccc(NC(=O)c2ccc3c(c2)N(C)CC3)c1] | (R)-N-(3-(1-((6-amino-[3,3'-bipyridin]-5-yl)oxy)ethyl)phenyl)-1-methylindoline-6-carboxamide | 466 |

Example 9

Synthesis of (R)—N-(3-(1-((2-amino-5-(1-(piperidin-4-yl)-1H-pyrazol-4-yl)pyridin-3-yl)oxy)ethyl)phenyl)-3-cyclopropylbenzamide

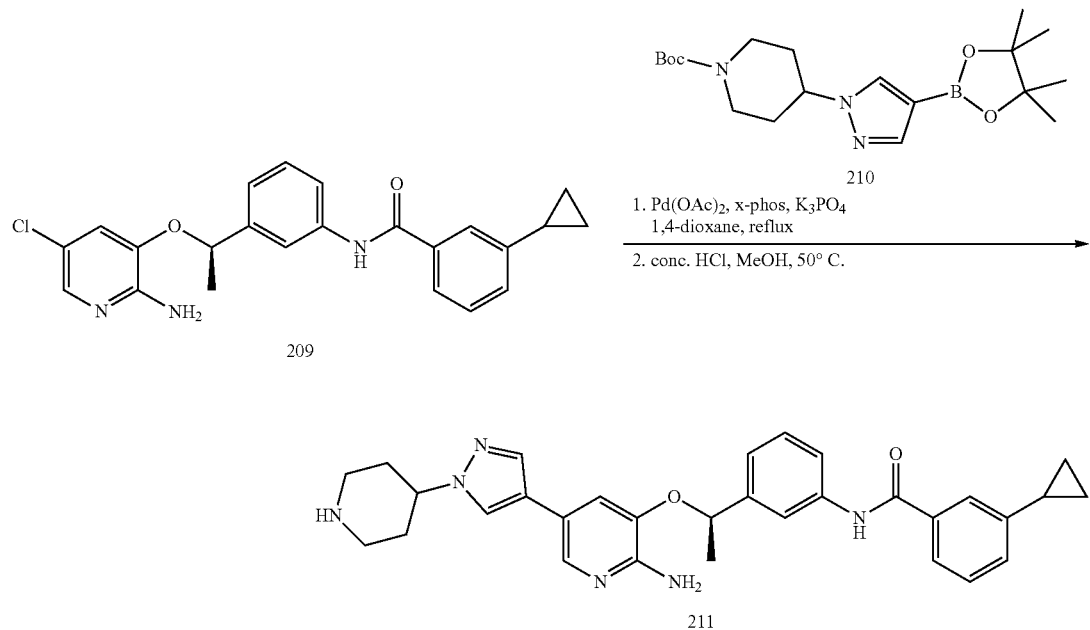

Step 1: Similar procedure to step 1 of example 7.
Step 2: To the solution of substrate (0.2 mmol) in methanol was added concentrated hydrochloric acid (1 mL). The reaction mixture was stirred at 50° C. for 2 h, then concentrated under reduced pressure. The residue was slurried with ether and the solid was collected by filtration to give the desired product.

Example 10

Synthesis of Compounds 212-217 was Similar Procedures to that of Compounds 168-195

TABLE 6

| Comps. No. | Compound structure | Compound name | MS [M + 1] |
|---|---|---|---|
| 212 | 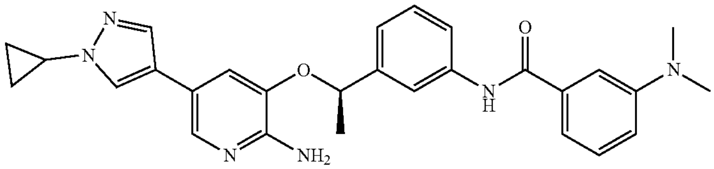 [SMILES: C[C@@H](Oc1cc(-c2cnn(C3CC3)c2)cnc1N)c1cccc(NC(=O)c2cccc(N(C)C)c2)c1] | (R)-N-(3-(1-((2-amino-5-(1-cyclopropyl-1H-pyrazol-4-yl)pyridin-3-yl)oxy)ethyl)phenyl)-3-(dimethylamino)benzamide | 483 |
| 213 | 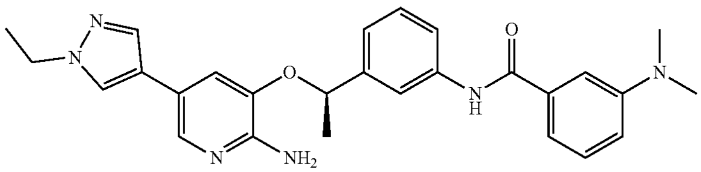 [SMILES: CCn1cc(-c2cnc(N)c(O[C@H](C)c3cccc(NC(=O)c4cccc(N(C)C)c4)c3)c2)cn1] | (R)-N-(3-(1-((2-amino-5-(1-ethyl-1H-pyrazol-4-yl)pyridin-3-yl)oxy)ethyl)phenyl)-3-(dimethylamino)benzamide | 471 |
| 214 | 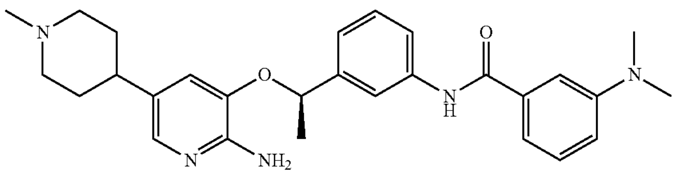 | (R)-N-(3-(1-((2-amino-5-(1-methylpiperidin-4-yl)pyridin-3-yl)oxy)ethyl)phenyl)-3-(dimethylamino)benzamide | 474 |
| 215 | 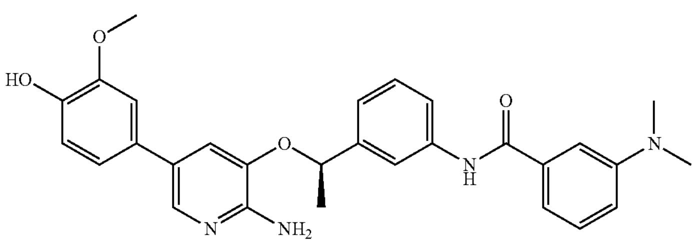 [SMILES: COc1cc(-c2cnc(N)c(O[C@H](C)c3cccc(NC(=O)c4cccc(N(C)C)c4)c3)c2)ccc1O] | (R)-N-(3-(1-((2-amino-5-(4-hydroxy-3-methoxyphenyl)pyridin-3-yl)oxy)ethyl)phenyl)-3-(dimethylamino)benzamide | 499 |
| 216 | 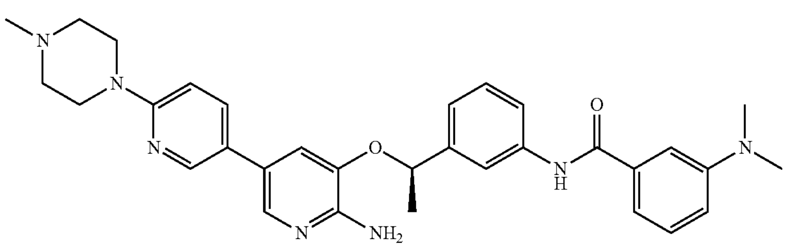 | (R)-N-(3-(1-((6-amino-6'-(4-methylpiperazin-1-yl)-[3,3'-bipyridin]-5-yl)oxy)ethyl)phenyl)-3-(dimethylamino)benzamide | 552 |
| 217 | 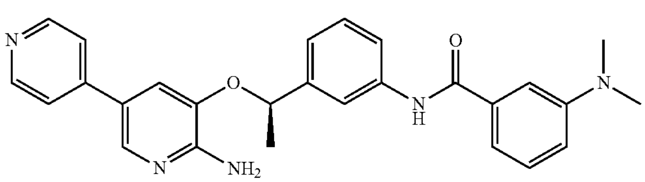 [SMILES: C[C@@H](Oc1cc(-c2ccncc2)cnc1N)c1cccc(NC(=O)c2cccc(N(C)C)c2)c1] | (R)-N-(3-(1-((6-amino-[3,4'-bipyridin]-5-yl)oxy)ethyl)phenyl)-3-(dimethylamino)benzamide | 454 |

Example 11
Synthesis of Compounds 222-226
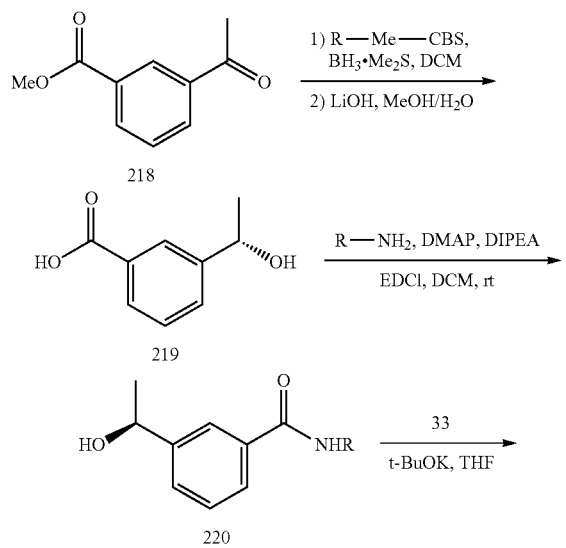
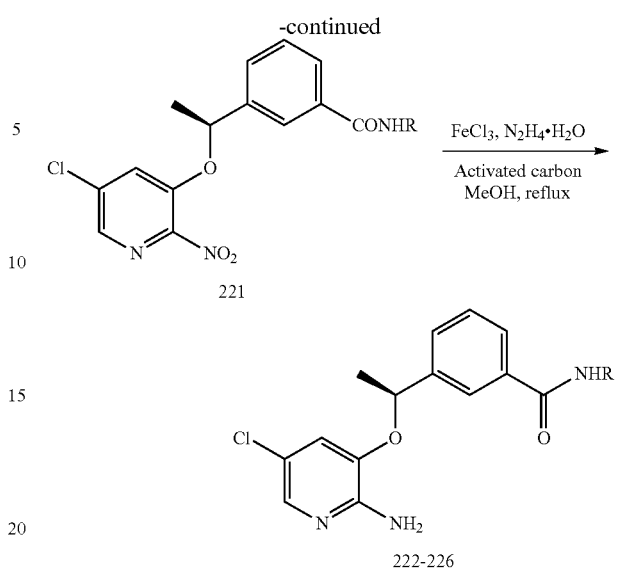
Synthesis of Compounds 222-226 is Similar Procedures to Compounds 54-71
TABLE 7
| Comps. No. | Compound structure | Compound name | MS [M + 1] |
|---|---|---|---|
| 222 | 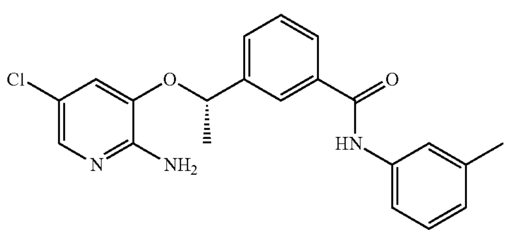 [SMILES: Cc1cccc(NC(=O)c2cccc([C@H](C)Oc3cc(Cl)cnc3N)c2)c1] | (S)-3-(1-((2-amino-5-chloropyridin-3-yl)oxy)ethyl)-N-(m-tolyl)benzamide | 382 |
| 223 | 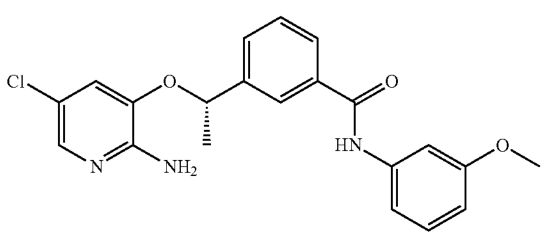 [SMILES: COc1cccc(NC(=O)c2cccc([C@H](C)Oc3cc(Cl)cnc3N)c2)c1] | (S)-3-(1-((2-amino-5-chloropyridin-3-yl)oxy)ethyl)-N-(3-methoxyphenyl)benzamide | 398 |
| 224 | 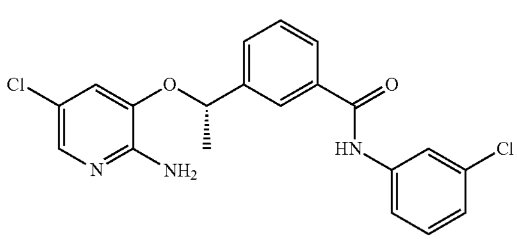 [SMILES: C[C@H](Oc1cc(Cl)cnc1N)c1cccc(C(=O)Nc2cccc(Cl)c2)c1] | (S)-3-(1-((2-amino-5-chloropyridin-3-yl)oxy)ethyl)-N-(3-chlorophenyl)benzamide | 402 |

TABLE 7-continued

| Comps. No. | Compound structure | Compound name | MS [M + 1] |
|---|---|---|---|
| 225 | 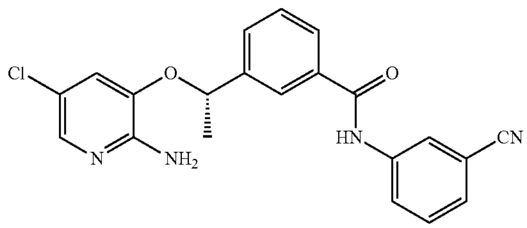 [SMILES: C[C@H](Oc1cc(Cl)cnc1N)c1cccc(C(=O)Nc2cccc(C#N)c2)c1] | (S)-3-(1-((2-amino-5-chloropyridin-3-yl)oxy)ethyl)-N-(3-cyanophenyl)benzamide | 393 |
| 226 | 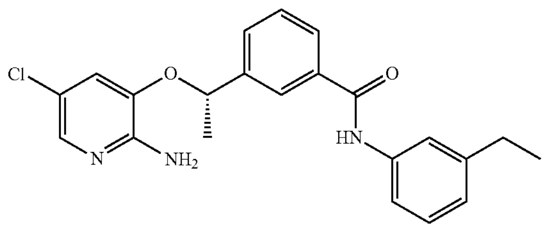 [SMILES: CCc1cccc(NC(=O)c2cccc([C@H](C)Oc3cc(Cl)cnc3N)c2)c1] | (S)-3-(1-((2-amino-5-chloropyridin-3-yl)oxy)ethyl)-N-(3-ethylphenyl)benzamide | 396 |

Example 12

Synthesis of N-(3-(1-((2-amino-5-chloropyridin-3-yl)oxy)ethyl)phenyl)-3-methylbenzamide

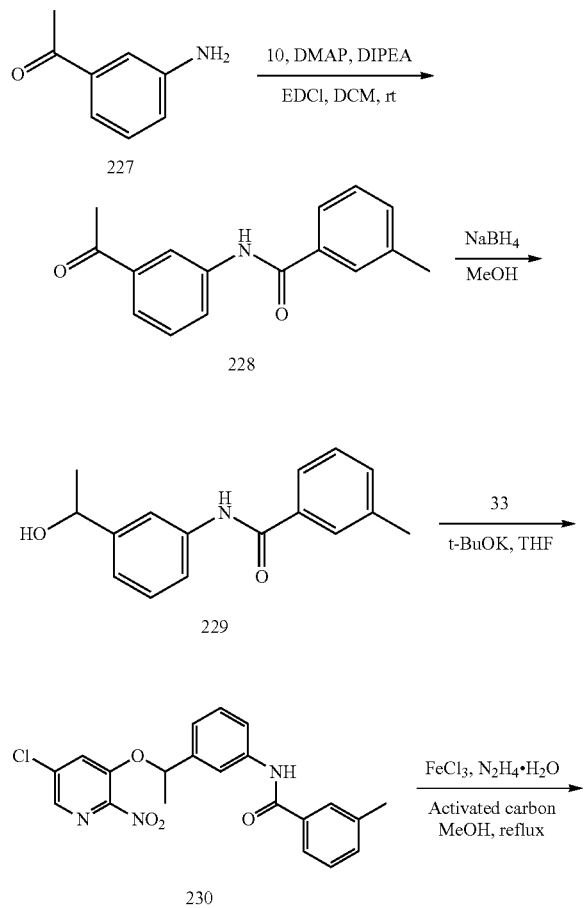

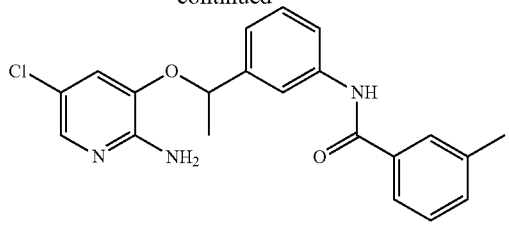

Step 1: To the solution of 3-aminoacetophenone (5.0 g, 37.0 mmol) in DCM (60 mL) was added 3-methyl benzoic acid (5.0 g, 37.0 mmol), DMAP (0.9 g, 7.4 mmol) and EDCI (10.6 g, 55.5 mmol) successively. Cooled and added DIPEA (14.3 g, 111 mmol) dropwise. The reaction mixture was warmed to room temperature for overnight, diluted with EA, and washed with water once, diluted hydrochloric acid for three times and brine once successively. The organic layer was dried with anhydrous sodium sulfate and concentrated in vacuo to give white solid (9.2 g, 98%).

Step 2: To the solution of 228 (2.0 g, 7.9 mmol) in methanol (20 mL) was added NaBH$_4$ (320 mg, 8.4 mmol) carefully in an ice bath. After stirring at room temperature for 1 h, the reaction was quenched with water and extracted with EA. The combined organic layers were dried with anhydrous sodium sulfate and concentrated under reduced pressure. The crude product was used directly in the next step without further purification.

Step 3: To the solution of 229 (100 mg, 0.39 mmol) in dried THF (10 mL) was added t-BuOK (44 mg, 0.39 mmol). The mixture was stirred at room temperature for 10 min, then was added 2-nitro-3-fluoro-5-chloropyridine (69 mg, 0.39 mmol) and continued to stirred at room temperature for 1 h. The reaction was quenched with silica gel (1 g), and purified by column chromatography to give the desired product (153 mg, 95%).

Step 4: To the solution of 230 (153 mg, 0.37 mmol) in methanol (5 mL) was added anhydrous ferric chloride (6 mg), activated carbon (20 mg). The resulting mixture was refluxed for 15 min, then was added hydrazine hydrate (80% aqueous solution, 0.1 mL) and refluxed for 1 h. The reaction mixture was poured into brine (20 mL), extracted with EA thrice. The combined organic layers were washed with brine, dried with anhydrous sodium sulfate and concentrated in vacuo to give the desired product (118 mg, 84%).

Example 13

Synthesis of N-(3-(((5-chloro-2-(methylamino)pyridin-3-yl)oxy)methyl)phenyl)-3-methylbenzamide

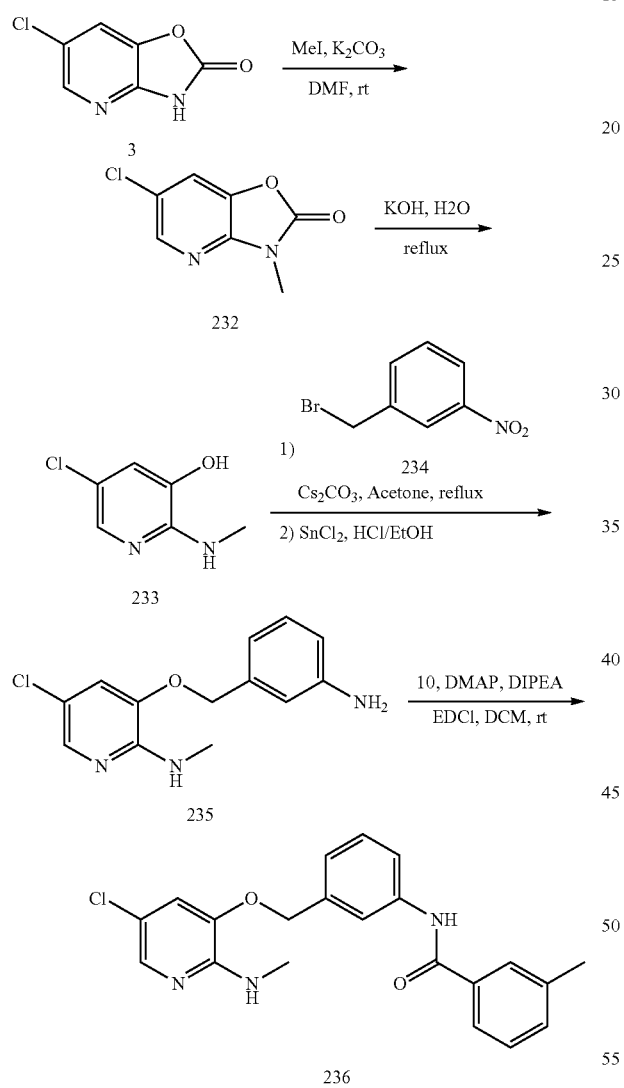

Step 1: To the solution of 3 (853 mg, 5.0 mmol) and K₂CO₃ (1.037 g, 7.5 mmol) in DMF (10 mL) was added MeI (1.065 g, 7.5 mmol). The reaction mixture was stirred at room temperature for overnight. The mixture was poured into brine, extracted with EA, and concentrated under reduced pressure. The crude product was used directly in the next step without further purification.

Step 2: To the suspension of the product of step 1 in water (20 mL) was added KOH (1.4 g, 25 mmol). The reaction mixture was refluxed for 16 h. After cooling to room temperature, the mixture was adjusted to PH~6 with diluted hydrochloric acid, and extracted with EA. The combined organic layers were dried, and concentrated in vacuo. The crude product was purified by column chromatography to give the desired product as white solid (735 mg, 93% for two steps).

Step 3: To the flask was added 233 (317 mg, 2.0 mmol), CsCO₃ (978 mg, 3.0 mmol) and acetone (20 mL). Then 234 (648 mg, 3.0 mmol) was added with stirring. The resulting mixture was refluxed for 3 h. After cooling, the solvent was removed under reduced pressure. The residue was added water, and extracted with EA. The combined organic layers were dried with anhydrous sodium sulfate and concentrated in vacuo. The crude was purified by column chromatography (PE/EA=1:1) to give white solid (485 mg, 83%). The solid was redissolved in EtOH (20 mL) and to the solution was added SnCl₂ (1.86 g, 8.3 mmol) and diluted hydrochloric acid (0.5 mL). The resulting mixture was refluxed for 3 h, then cooled, and diluted with ice water. The mixture was adjusted to PH~14 with Sodium hydroxide, and extracted with EA thrice. The combined organic extracts were washed with brine, dried with anhydrous sodium sulfate, filtered, and concentrated under reduced pressure. The crude was purified by column chromatography (PE/EA=1:1) to give white solid (345 mg, 76%).

Step 4: Similar procedure to example 3 was followed to arrive at the title compound, with the LC-MS[M+H]-m/z 398.

Example 14

Synthesis of N-(3-(((2-aminopyridin-3-yl)oxy)methyl)phenyl)-3-methylbenzamide

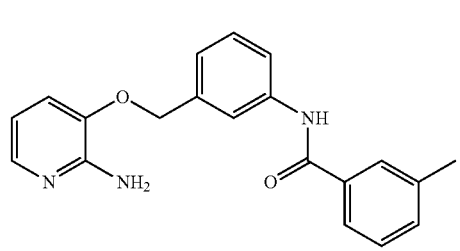

Similar procedure to the example 3 was followed to arrive at the title compound, with LC-MS[M+H]-m/z 334.

Example 15

Synthesis of 5-(((2-amino-5-chloropyridin-3-yl)oxy)methyl)-N-((6-(trifluoromethyl)pyridin-3-yl)methyl)pyridin-2-amine

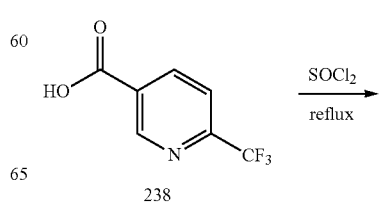

-continued

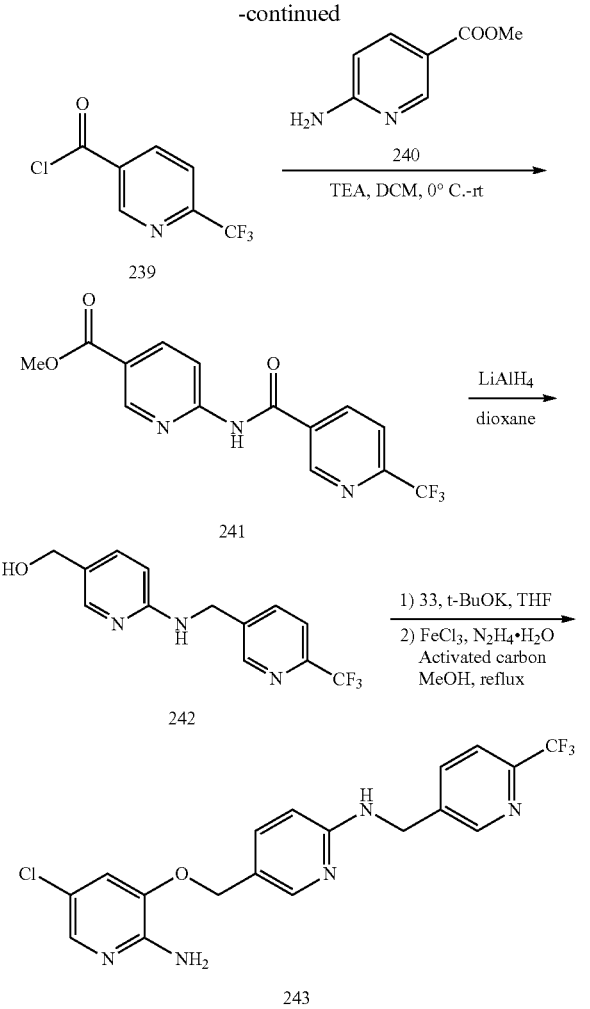

Step 1: To 238 (5.0 g, 26.2 mmol) was added SOCl₂ (10 mL), the mixture was refluxed for overnight. After cooling, SOCl₂ was removed under reduced pressure and the residual SOCl₂ was removed by azeotropic distillation with toluene. The crude product obtained was used directly in the next step.

Step 2: To the ice-cold solution of 240 (4.0 g, 26.2 mmol), TEA (5.3 g, 52.4 mmol) in DCM (50 mL) was added 239 in DCM (20 mL) dropwise. The resulting mixture was warmed to room temperature for overnight, then washed with water thrice, dried with anhydrous sodium sulfate, filtered, and concentrated in vacuo. The residue was purified by column chromatography (PE/EA=4:1) to give white solid (6.2 g, 73%).

Step 3: To the suspension of LiAlH₄ (1.9 g, 50 mmol) in dioxane (25 mL) was added 241 (1.63 g, 5.0 mmol) in dioxane (10 mL) dropwise at 10° C. The reaction mixture was refluxed for overnight, then cooled in ice bath and was carefully added 15% Sodium hydroxide aqueous solution (25 mL) dropwise. The resulting mixture was warmed to room temperature and stirred for 1 h. The solid formed was filtered off, and washed with EA. The organic solution was dried and concentrated in vacuo. The residue was purified by column chromatography to give viscous liquid (327 mg, 23%).

Step 4: Similar procedure to steps 3 and 4 of the example 12 was followed to arrive at the title compound, with the LC-MS[M+H]-m/z 410.

Example 16

Synthesis of 5-chloro-3-((3-methoxy-4-((4-methoxybenzyl)oxy)benzyl)oxy)pyridin-2-amine

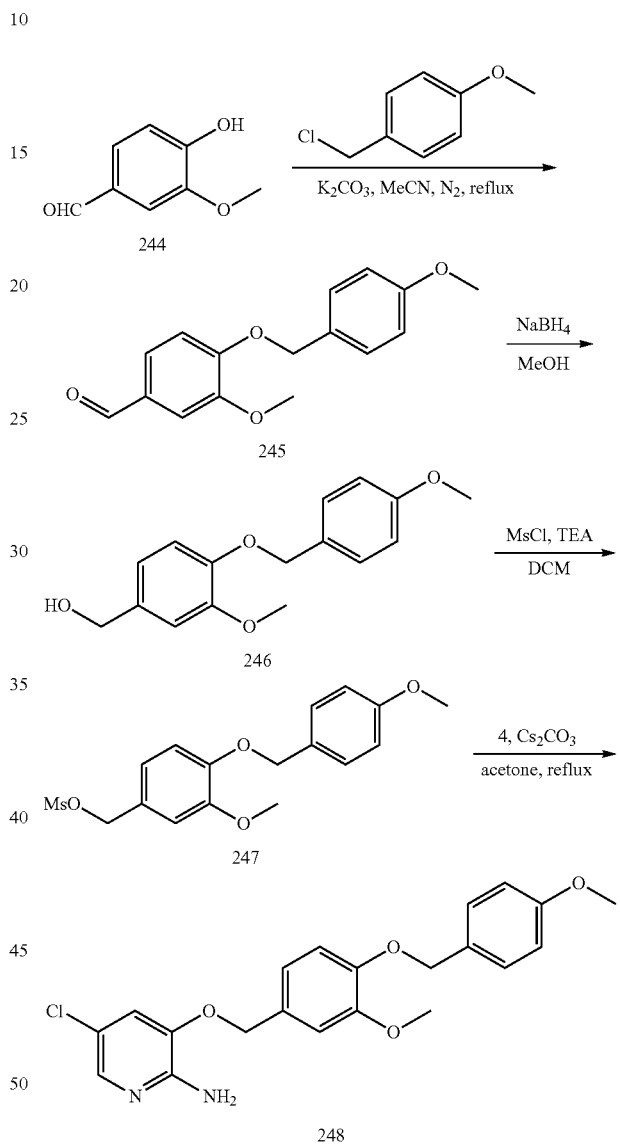

Step 1: To the suspension of 244 (5.0 g, 32.9 mmol) in MeCN was added K₂CO₃ (6.8 g, 49.4 mmol) and 4-Methoxybenzylchloride (7.7 g, 49.4 mmol). The reaction was refluxed for overnight. The mixture was cooled down, poured into water, and extracted with EA. The combined organic layers were washed with water, dried, and concentrated. The crude was purified by column chromatography to give white solid (7.5 g, 83%).

Step 2: To the solution of 245 (1.0 g, 3.7 mmol) in MeOH (10 mL), was added NaBH₄ (141 mg, 3.7 mmol). The reaction mixture was stirred for 0.5 h, then diluted with water, and extracted with EA. The combined organic layers were dried with anhydrous Na$_2$SO$_4$ and concentrated under reduced pressure. The crude was used directly in the next step without further purification. Similar procedure of steps 3 and 4 to the example 2 was followed to arrive at the title compound, with the LC-MS [M+H]-m/z 401.

Example 17

Synthesis of 5-chloro-3-(3-methoxy-4-((4-methoxybenzyl)oxy)phenoxy)pyridin-2-amine

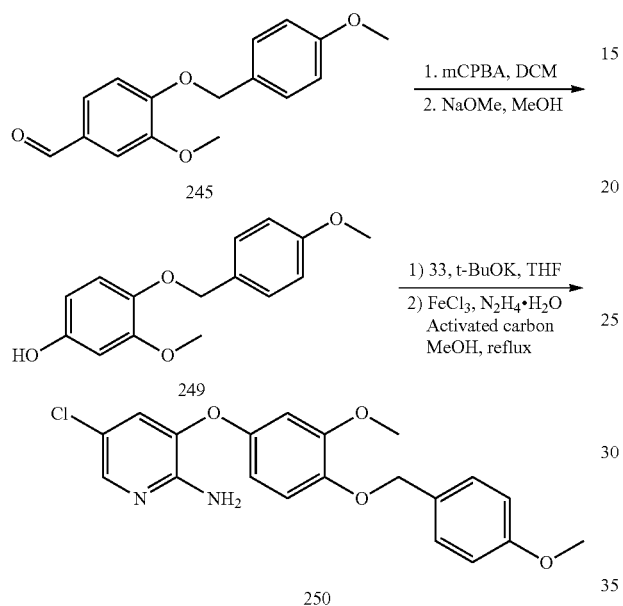

Step 1: To the solution 245 (1.0 g, 3.7 mmol) in DCM (20 mL) was added 3-Chloroperoxybenzoic acid (1.3 g, 7.4 mmol), and the reaction mixture was stirred for overnight. The insolubles was filtered off, and washed with sodium carbonate solution twice. The filtrate was dried and concentrated, then MeOH (20 mL) and MeONa (500 mg, 9.3 mmol) was added and the mixture was stirred for overnight. Most of the solvent was removed under reduced pressure and the residue was added water, adjusted to PH~4-5 with diluted hydrochloric acid and extracted with EA. The combined organic layers were dried, concentrated and the residue was purified by column chromatography to give white solid (547 mg, 57%).

Step 2: Similar procedure to steps 3 and 4 of the example 12 was followed to arrive at the title compound with LC-MS[M+H]-m/z 387.

Example 18

Synthesis of N-(3-(((3-amino-6-chloropyrazin-2-yl)oxy)methyl)phenyl)-3-methylbenzamide

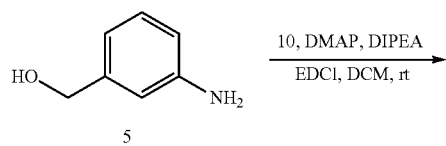

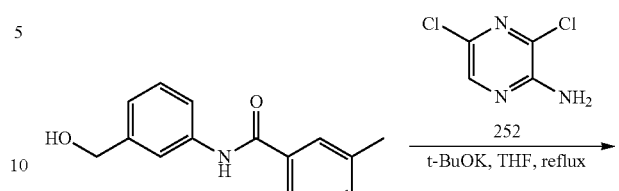

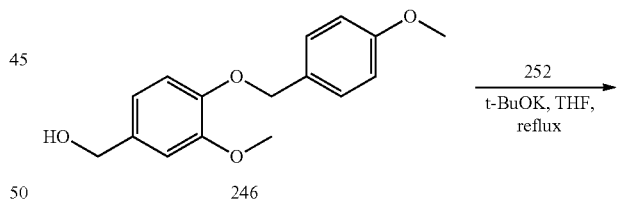

Similar procedure to steps 1 and 3 of the example 18 was followed to arrive at compound 253 with LC-MS[M+H]-m/z 369.

Example 19

Synthesis of 5-chloro-3-((3-methoxy-4-((4-methoxybenzyl)oxy)benzyl)oxy)pyrazin-2-amine

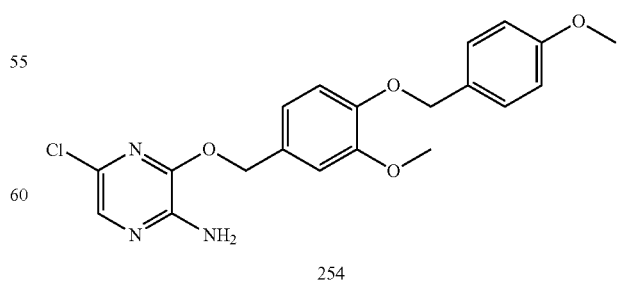

Similar procedure to step 3 of the example 12 was followed to arrive at compound 254 with LC-MS[M+H]-m/z 402.

Example 20

Synthesis of 5-chloro-3-(3-methoxy-4-((4-methoxybenzyl)oxy)phenoxy)pyrazin-2-amine

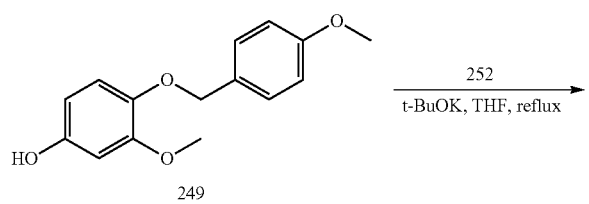

Similar procedure to step 3 of the example 18 was followed to arrive at compound 255 with LC-MS[M+H]-m/z 388.

Example 21

Similar procedure to the example 18 was followed to arrive at compounds 256-258.

Example 22

Synthesis of 5-chloro-3-((6-((4-methoxybenzyl)oxy)pyridin-3-yl)methoxy)pyridin-2-amine

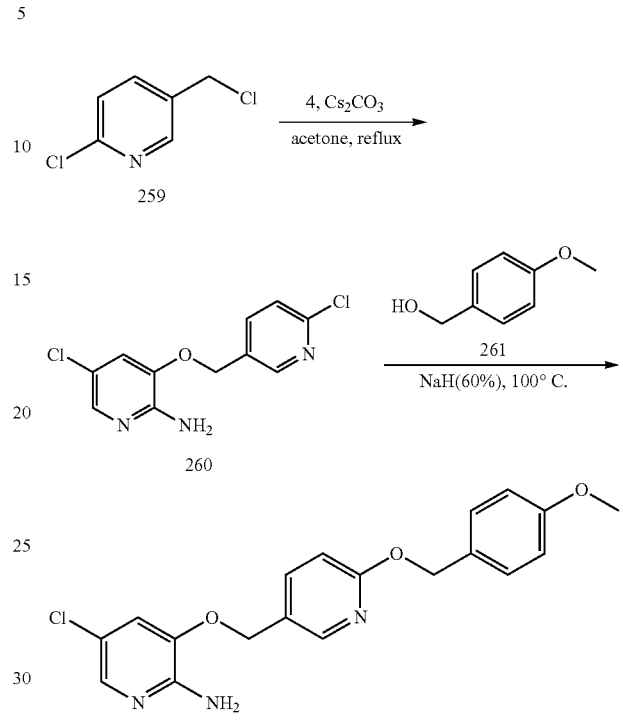

TABLE 8

| Comps. No. | Compound structure | Compound name | MS [M + 1] |
|---|---|---|---|
| 256 | 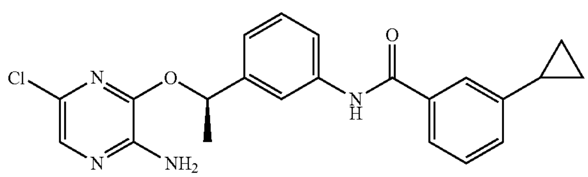 [SMILES: C[C@@H](Oc1nc(Cl)cnc1N)c1cccc(NC(=O)c2cccc(C3CC3)c2)c1] | (R)-N-(3-(1-((3-amino-6-chloropyrazin-2-yl)oxy)ethyl)phenyl)-3-cyclopropylbenzamide | 409 |
| 257 | 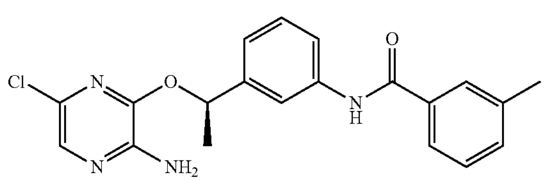 [SMILES: Cc1cccc(C(=O)Nc2cccc([C@@H](C)Oc3nc(Cl)cnc3N)c2)c1] | (R)-N-(3-(1-((3-amino-6-chloropyrazin-2-yl)oxy)ethyl)phenyl)-3-methylbenzamide | 383 |
| 258 | 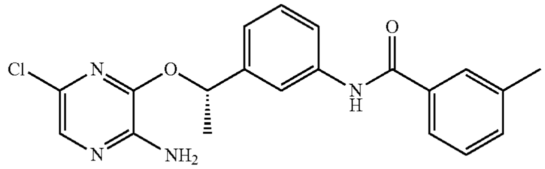 [SMILES: Cc1cccc(C(=O)Nc2cccc([C@H](C)Oc3nc(Cl)cnc3N)c2)c1] | (S)-N-(3-(1-((3-amino-6-chloropyrazin-2-yl)oxy)ethyl)phenyl)-3-methylbenzamide | 383 |

Step 1: To a stirred solution of 4 (1.45 g, 10.0 mmol), cesium carbonate (6.52 g, 20.0 mmol) in acetone (50 mL) was added 259 (3.24 g, 20 mmol). The resulting mixture was refluxed for overnight. After cooling, the reaction mixture was poured into brine and extracted with ethyl acetate. The combined organic layers were dried by anhydrous sodium sulfate and concentrated in vacuum. The residue was purified by column chromatography to give the desired product as yellow solid (1.65 g, 61%).

Step 2: Sodium hydride (60%, 200 mg, 5.0 mmol) was added to 4-methoxybenzyl alcohol (2 mL) with ice bath cooled. The resulting mixture was stirred for 10 minutes, and then 260 (135 mg, 0.5 mmol) was added. The reaction was stirred at 100° C. for overnight. After cooling to room temperature, silica gel was added and the resulting mixture was concentrated under reduced pressure. The residue was purified by column chromatography to give the desired product as white solid (65 mg, 35%). LC-MS[M+H]-m/z 372.

Example 23

Synthesis of (E)-5-chloro-3-(3-methoxy-4-((4-methoxybenzyl)oxy)styryl)pyridin-2-amine

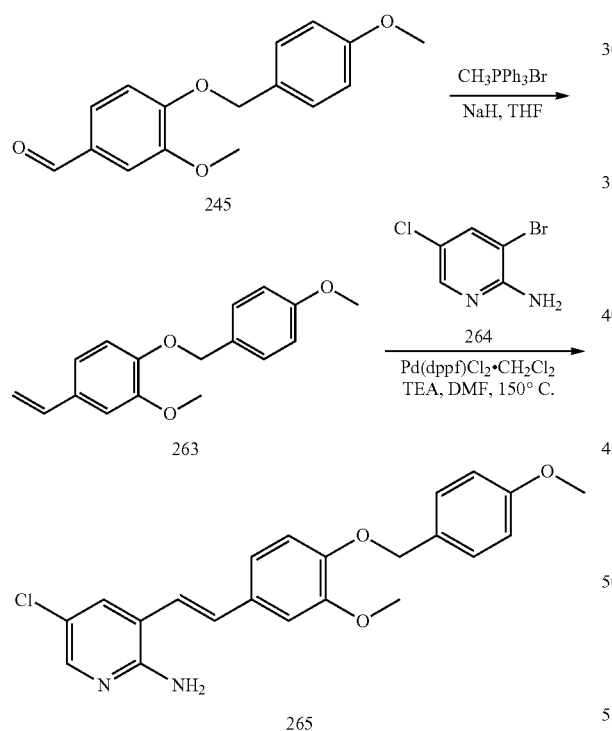

Step 1: Methyltriphenylphosphine bromide (1.96 g, 5.5 mmol) and sodium hydride (60%, 220 mg, 5.5 mmol) were added to anhydrous tetrahydrofuran under nitrogen atmosphere and the mixture was stirred at 25° C. for 1 hour. Then to the mixture was add 245 (1.36 g, mmol) and this was stirred for 16 hours at 25° C. The reaction was quenched with water, and the resulting mixture was extracted with ethyl acetate. The combined organic layers were dried with anhydrous sodium sulfate, concentrated under reduced pressure, and the crude was purified by column chromatography (PE:EA=20:1) to give the desired product as white solid (1.22 g, 90%). LC-MS[M+Na]-m/z 293.

Step 2: To a stainless steel tube was added 5-chloro-3-bromo-2-aminopyridine (104 mg, 0.5 mmol), 263 (203 mg, 0.75 mmol) and DMF (5 mL). The mixture was stirred and degassed with nitrogen, after 5 minutes Pd(dppf)Cl$_2$CH$_2$Cl$_2$ (41 mg, 0.05 mmol), triethylamine (152 mg, 1.5 mmol) was added successively. The tube was sealed, and heated at 150° C. for overnight. After cooling, to the reaction solution was added brine and the resulting mixture was extracted with ethyl acetate. The combined organic phase was washed with brine twice, dried and concentrated. The residue was purified by column chromatography (PE:EA=2:1) to give white solid (65 mg, 33%). LC-MS[M+H]-m/z 397.

Example 24

Synthesis of (E)-N-(3-(2-(2-amino-5-chloropyridin-3-yl)vinyl)phenyl)-3-methylbenzamide

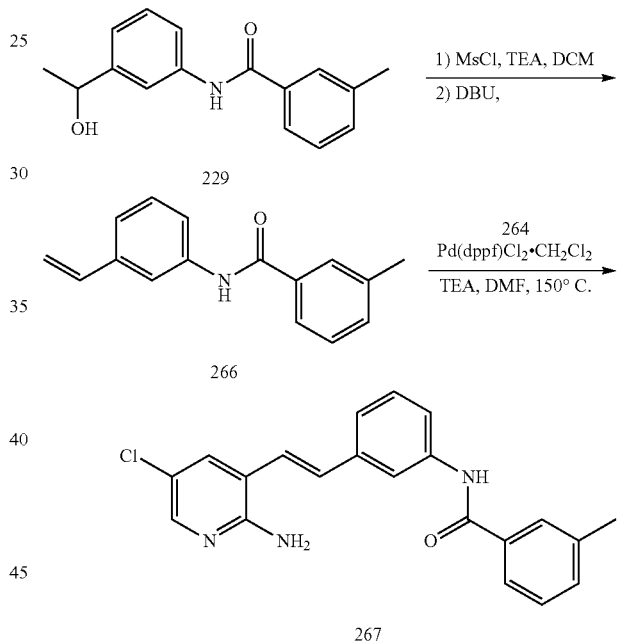

Step 1: To the solution of Compound 229 (2.0 g, 7.8 mmol) in methane dichloride (40 mL) was added triethylamine (1.58 g, 15.6 mmol), and methyl sulfonyl chloride (1.08 g, 9.4 mmol) was added dripwise with ice bath cooled. The resulting mixture was warmed to room temperature and reacted for overnight. The reaction mixture was washed with water for one time and washed with saturated sodium bicarbonate solution for two times. The organic layer was dried with anhydrous sodium sulfate and concentrated in vacuum. After cooling, to the residue was added DBU (10 mL) and the mixture was stirred at 50° C. for overnight. After cooling, water was added and the mixture was extracted with ethyl acetate. The combined organic phase was washed with diluted hydrochloric acid twice, dried, concentrated in vacuum, and the residue was purified by column chromatography to give white solid (854 mg, 46%).

Step 2: Similar procedure to step 2 of the example 23 was followed to arrive at compound 267 with LC-MS[M+H]-m/z 364.

Example 25

Synthesis of N-(3-(2-(2-amino-5-chloropyridin-3-yl)cyclopropyl)phenyl)-3-methylbenzamide

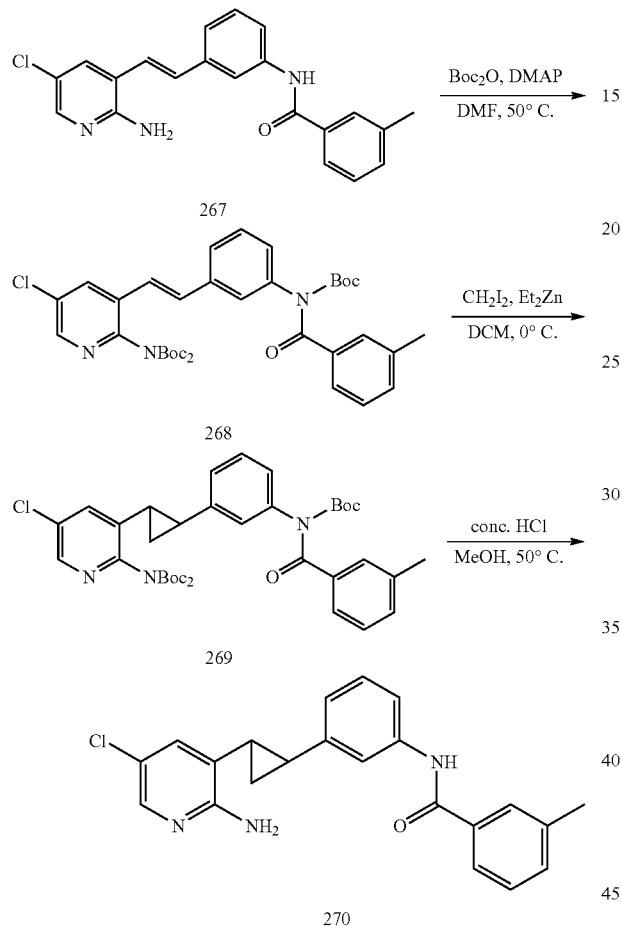

Step 1: To the solution of 267 (200 mg, 0.55 mmol) and DMAP (269 mg, 2.2 mmol) in DMF (10 mL) was added Boc$_2$O (480 mg, 2.2 mmol) dropwise. The reaction mixture was stirred at 50° C. for 20 h, then poured into brine and extracted with ethyl acetate. The combined organic layers were washed three times with brine, dried and concentrated under reduced pressure. The residue was purified by column chromatography to give the desired product as yellow solid (157 mg, 43%).

Step 2: Fresh distilled dichloromethane (5.0 mL) was added to the Schlenk tube at room temperature under nitrogen atmosphere, and then diethyl zinc solution (1.0 mL, 1.0 mmol) (1.0 M in hexane) was added. After cooling for 10 minutes at −40° C., a solution of diiodomethane (540 mg, 2.0 mmol) in dichloromethane (5.0 mL) was added dropwise. After reacting at −40° C. for 1 h, a solution of trichloroacetic acid (16 mg, 0.1 mmol) and DME (45 mg, 0.5 mmol) in dichloromethane (1 mL) was added and the reaction temperature was warmed to −15° C. and stirred for 1 h. At this temperature, to the reaction solution was added a solution of 268 (133 mg, 0.2 mmol) in dichloromethane (5 mL) dropwise. Then it was warmed to 25° C. and reacted for 2 h. The reaction mixture was quenched with saturated sodium bicarbonate solution, stirred at room temperature for 20 minutes, diluted with water, and extracted with dichloromethane twice. The combined organic layers were washed with saturated ammonium chloride solution, sodium sulfite solution, sodium bicarbonate and brine successively, dried, filtered and concentrated. The residue was purified by column chromatography to give the desired product as light yellow solid (68 mg, 50%).

Step 3: To the solution of 269 (68 mg, 0.1 mmol) in methanol (5 mL) was added concentrated hydrochloric acid (0.2 mL). The resulting mixture was reacted for 4 h at 50° C., then concentrated in vacuum. The residue was resolved in water, and adjusted to alkaline with sodium bicarbonate. The mixture was extracted with EA and the organic layer was dried and concentrated under reduced pressure. The crude was purified by column chromatography to give white solid (32 mg, 85%). LC-MS[M+H]-m/z 378.

Example 26

Synthesis of Compound 272-276

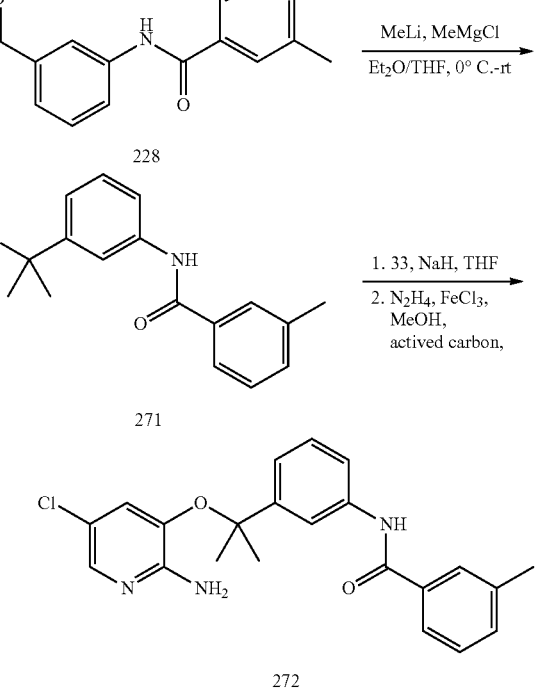

Step 1: To a solution of MeMgCl (3M in ether, 2.0 mL, 6.0 mmol) and MeLi (3M in ether, 2.0 mL, 6.0 mmol) in anhydrous THF (30 mL) that had stirred at 0° C. for 0.5 h was added 228 (507 mg, 2 mmol) in THF (10 mL) under nitrogen atmosphere. After stirring at 0° C. for 1 h, the reaction mixture was warmed to room temperature and stirred for overnight. And then the mixture was recooled to 0° C., quenched with saturated NH₄Cl solution and extracted with ethyl acetate. The combined organic layers were dried by anhydrous sodium sulfate, filtered and concentrated. The crude was purified by column chromatography to give white solid (404 mg, 75%).

Step 2: Compound 271 (135 mg, 0.5 mmol) was dissolved in dry THF (15 mL), and sodium hydride (60%, 24 mg, 0.6 mmol) was added at 0° C. The suspension was stirred for 10 minutes, then 33 (88 mg, 0.5 mmol) was added. The reaction mixture was stirred at room temperature for overnight, and then poured into brine. The resulting mixture was extracted with ethyl acetate. The combined organic layers were dried with anhydrous sodium sulfate, filtered and concentrated. The crude was purified by column chromatography to give light yellow solid (100 mg, 47%). The obtained solid (100 mg, 0.24 mmol) was redissolved in methanol (10 mL), and anhydrous ferric chloride (6 mg), activated carbon (20 mg) was added. The mixture was refluxed for 15 minutes, then hydrazine hydrate (80% aqueous solution) (0.1 mL) was added dropwise. The resulting mixture was refluxed for 1 h, then poured into brine, and extracted with EA for three times. The combined organic layers were washed with brine once, dried with anhydrous sodium sulfate. The solvent was removed under reduced pressure and the crude was purified by column chromatography to give white solid (85 mg. 89%).

Synthesis of compounds 273-276 is similar to that of 272.

TABLE 9

| Comps. No. | Compound structure | Compound name | MS [M + 1] |
|---|---|---|---|
| 272 | 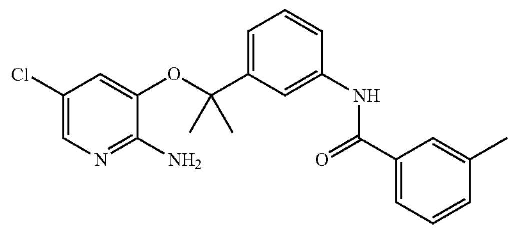 [SMILES: Cc1cccc(C(=O)Nc2cccc(C(C)(C)Oc3cc(Cl)cnc3N)c2)c1] | N-(3-(2-((2-amino-5-chloropyridin-3-yl)oxy)propan-2-yl)phenyl)-3-methylbenzamide | 396 |
| 273 | 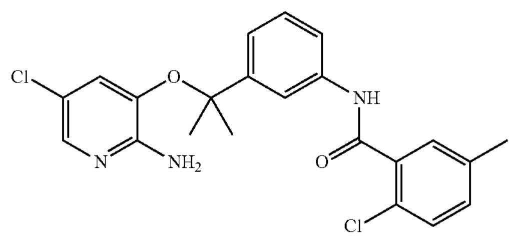 [SMILES: Cc1ccc(Cl)c(C(=O)Nc2cccc(C(C)(C)Oc3cc(Cl)cnc3N)c2)c1] | N-(3-(2-((2-amino-5-chloropyridin-3-yl)oxy)propan-2-yl)phenyl)-2-chloro-5-methylbenzamide | 430 |
| 274 | 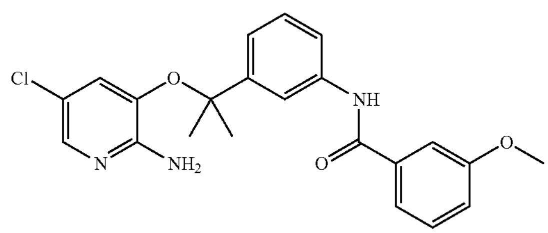 [SMILES: COc1cccc(C(=O)Nc2cccc(C(C)(C)Oc3cc(Cl)cnc3N)c2)c1] | N-(3-(2-((2-amino-5-chloropyridin-3-yl)oxy)propan-2-yl)phenyl)-3-methoxybenzamide | 412 |
| 275 | 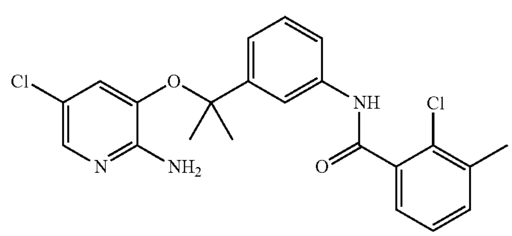 [SMILES: Cc1cccc(C(=O)Nc2cccc(C(C)(C)Oc3cc(Cl)cnc3N)c2)c1Cl] | N-(3-(2-((2-amino-5-chloropyridin-3-yl)oxy)propan-2-yl)phenyl)-2-chloro-3-methylbenzamide | 430 |
| 276 | 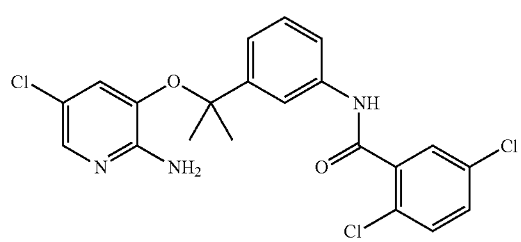 [SMILES: CC(C)(Oc1cc(Cl)cnc1N)c1cccc(NC(=O)c2cc(Cl)ccc2Cl)c1] | N-(3-(2-((2-amino-5-chloropyridin-3-yl)oxy)propan-2-yl)phenyl)-2,5-dichlorobenzamide | 450 |

Example 27

Synthesis of N-(3-(1-((2-amino-5-chloropyridin-3-yl)oxy)cyclopropyl)phenyl)-3-methylbenzamide

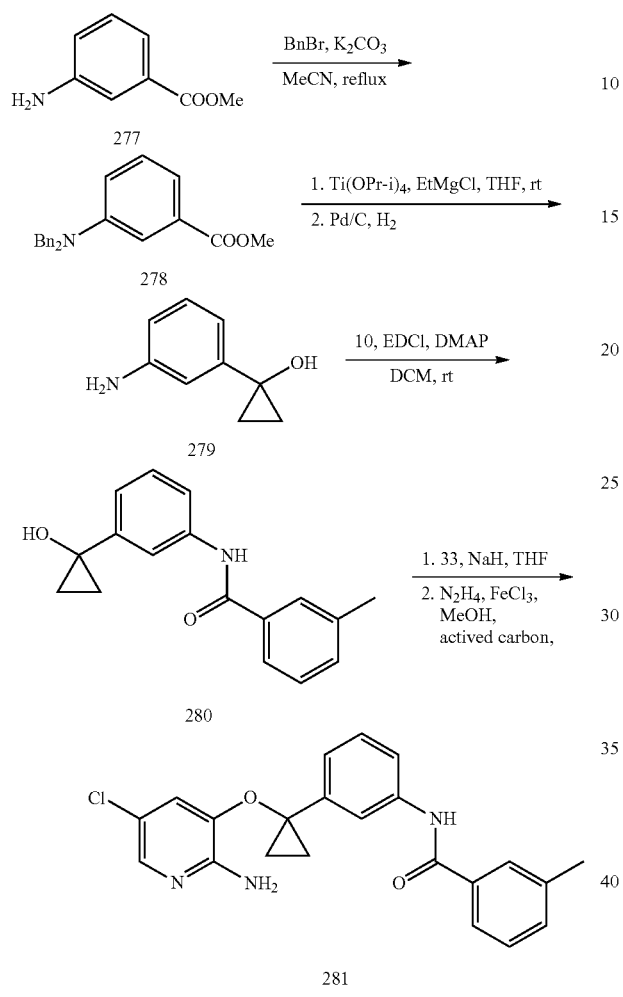

Step 1: To the solution of 277 (2.0 g, 13.2 mmol) and K$_2$CO$_3$ (5.47 g, 39.6 mmol) in acetonitrile (30 mL) was added BnBr (5.7 g, 33.0 mmol) and the reaction was stirred at room temperature for overnight. The reaction mixture was poured into brine and extracted with ethyl acetate. The combined organic phase was washed with brine again, dried and concentrated in vacuum. The residue was purified by column chromatography to give the desired product (3.4 g, 78%).

Step 2: To the solution of 278 (1.3 g, 4.0 mmol) and Ti(OPr-i)$_4$ (1.6 g, 6.4 mmol) in THF (10 mL) was added a solution of EtMgBr (3M in diethyl ether, 11.2 mmol, 3.7 mL) in anhydrous THF (10 mL) dropwise at 0° C. under nitrogen atmosphere. The reaction mixture was warmed to room temperature and stirred for overnight. The mixture was cooled to 0° C., quenched by saturated NH$_4$Cl, and extracted with ethyl acetate. The combined organic phase was washed with saturated NaHCO$_3$, water and brine successively. The resulting mixture was purified by column chromatography (PE/EA=5:1) to give the desired product as colorless oil (553 mg, Yield: 42%).

The obtained oil (500 mg, 1.5 mmol) was redissolved in methanol (20 mL), and then it was added 10% Pd/C (50 mg). The resulting mixture was stirred at room temperature under a hydrogen atmosphere for overnight, filtrated and concentrated. The residue was purified by column chromatography (PE/EA=2:1) to give yellow solid (21 mg, 9%).

Step 3: similar to example 3.

Step 4: Similar procedure to step 3 of example 26 was followed. LC-MS[M+H]-m/z 394.

Example 28

Synthesis of N-(3-(1-((2-amino-5-chloropyridin-3-yl)oxy)cyclobutyl)phenyl)-3-methylbenzamide

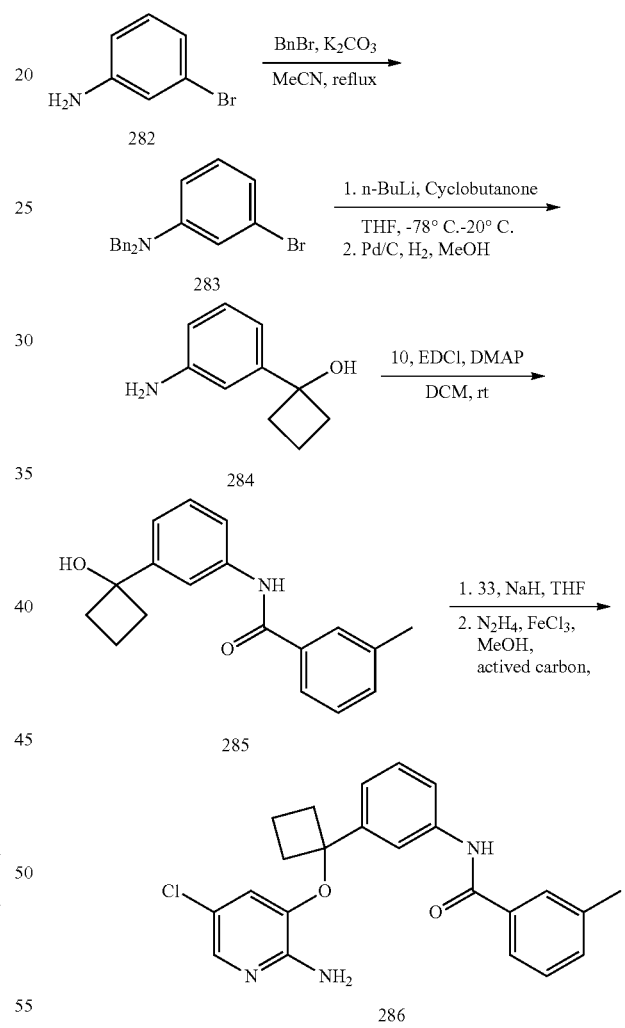

Step 1: Similar procedure to step 1 of example 27 was followed.

Step 2: To the solution of 283 (1.4 g, 4.0 mmol) in anhydrous THF (20 mL) was slowly added n-BuLi (1M in Hexane solution. 5.2 mmol) dropwise at −78° C. under nitrogen atmosphere. After the solution was stirred for 15 min, cyclobutanone (280 mg, 4.0 mmol) was added dropwise. The mixture was warmed to −20° C. and stirred for 1 h. The reaction was quenched by saturated NH$_4$Cl (50 mL), and etracted with ethyl acetate (50 mL×2). The combined organic phase was washed with brine (50 mL) for two times and dried by anhydrous sodium sulfate. The residue was purified by column chromatography to give the desired product (797 mg, Yield: 58%).

Similar procedure to example 3 was followed.

Similar procedure to the step 3 of example 26 was followed. LC-MS[M+H]-m/z: 408.

Example 29

Synthesis of N-(3-(1-((2-amino-5-chloropyridin-3-yl)oxy)cyclopentyl)phenyl)-3-methylbenzamide

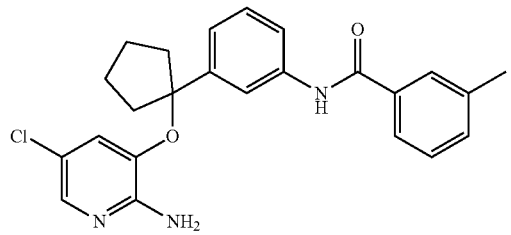

287

Synthesis of compound 287 is similar to that of Example 28, with the LC-MS[M+H]-m/z 422.

Example 30

Synthesis of N-(3-(1-((2-amino-5-chloropyridin-3-yl)oxy)cyclohexyl)phenyl)-3-methylbenzamide

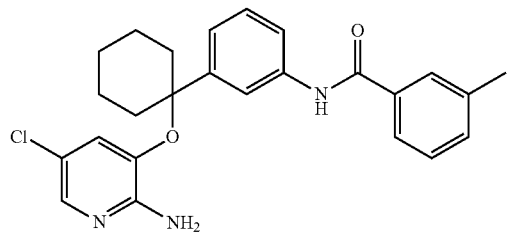

288

Synthesis of compound 288 is similar to that of Example 28, with the LC-MS[M+H]-m/z 436.

Example 31

Synthesis of 5-chloro-3-((5-methoxy-6-((4-methoxybenzyl)oxy)pyridin-3-yl)oxy)pyridin-2-amine

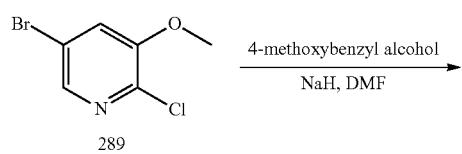

289

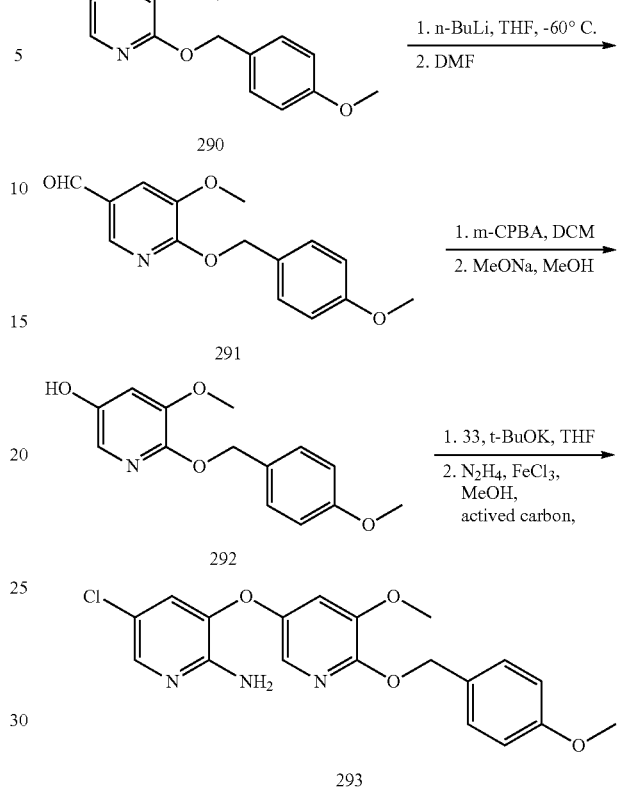

The synthesis of intermediate 292 is referred to paper [Meyers M J, Pelc M, Kamtekar S, et al. [J]. Bioorganic & Medicinal Chemistry Letters, 2010, 20(5):1543-1547.]

Step 4: Similar procedure to step 3 and 4 of example 12 was followed, with the LC-MS[M+H]-m/z 388.

Example 32

Synthesis of 5-((2-amino-5-chloropyridin-3-yl)oxy)-N-((6-(trifluoromethyl)pyridin-3-yl)methyl)pyridin-2-amine

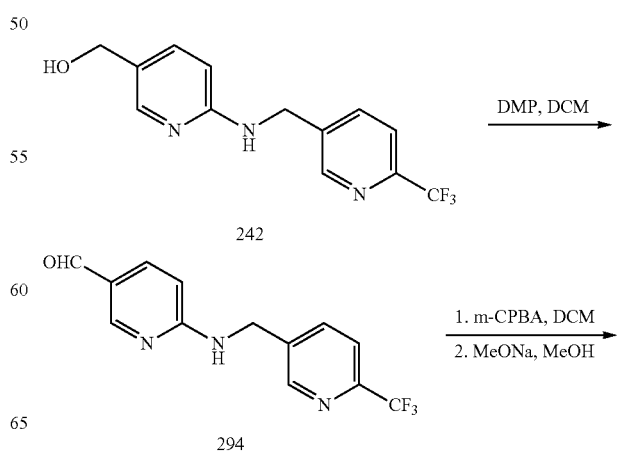

-continued

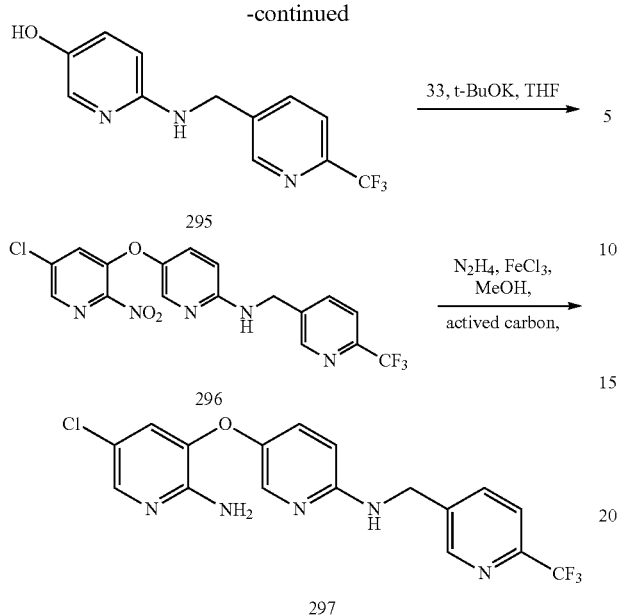

Similar procedure to example 31 was followed to arrive at compound 297, with the LC-MS[M+H]-m/z 396.

Example 33

Synthesis of 4-((4-((2-amino-5-chloropyridin-3-yl)oxy)-2-methoxyphenoxy)methyl)benzonitrile

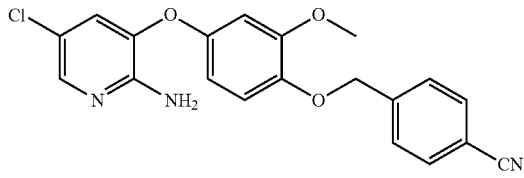

Similar procedure to example 13 was followed to arrive at compound 298, with the LC-MS[M+H]-m/z 382.

Example 34

Synthesis of 5-chloro-3-(3-methoxy-4-((4-(trifluoromethyl)benzyl)oxy)phenoxy)pyridin-2-amine

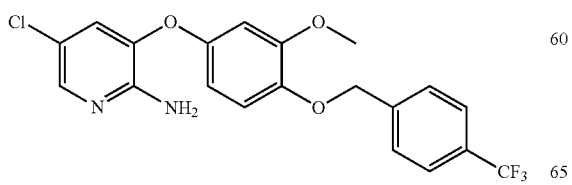

Similar procedure to example 17 was followed to arrive at compound 299, with the LC-MS[M+H]-m/z 425.

Example 35

Synthesis of 4-(((5-((2-amino-5-chloropyridin-3-yl)oxy)-3-methoxypyridin-2-yl)oxy)methyl)benzonitrile

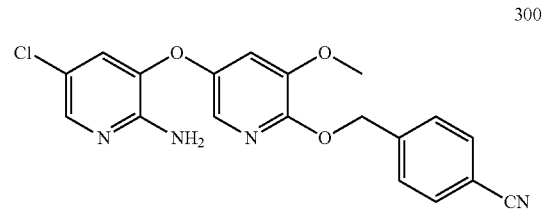 [SMILES: COc1cc(Oc2cc(Cl)cnc2N)cnc1OCc1ccc(C#N)cc1]

Similar procedure to example 31 was followed to arrive at compound 300, with the LC-MS[M+H]-m/z 383.

Example 36

Synthesis of 5-chloro-3-((6-((4-chlorobenzyl)oxy)-5-methoxypyridin-3-yl)oxy)pyridin-2-amine

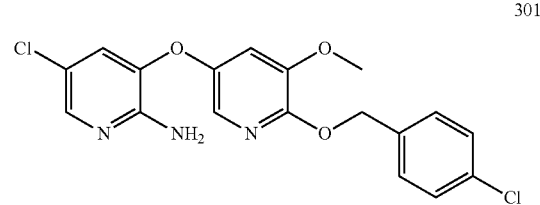 [SMILES: COc1cc(Oc2cc(Cl)cnc2N)cnc1OCc1ccc(Cl)cc1]

Similar procedure to example 31 was followed to arrive at compound 301, with the LC-MS[M+H]-m/z 392.

Example 37

Synthesis of Compounds 302-314 was Similar Procedure to Example 5

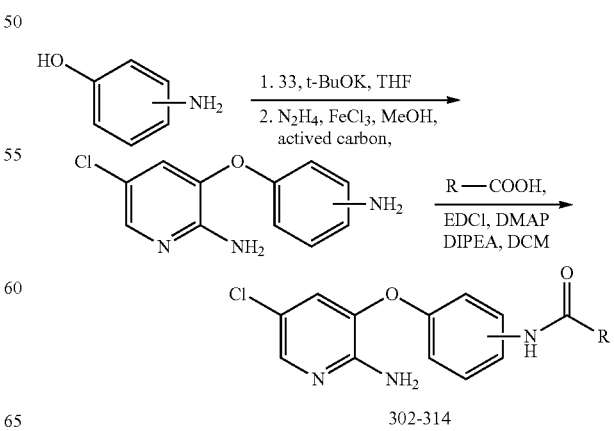

TABLE 10

| Comps. No. | Compound structure | Compound name | MS [M + 1] |
|---|---|---|---|
| 302 | 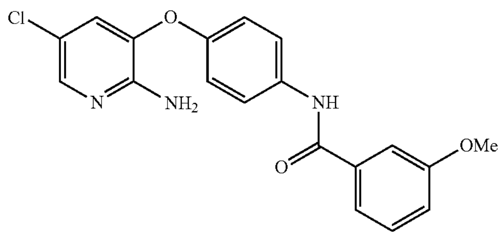 [SMILES: COc1cccc(C(=O)Nc2ccc(Oc3cc(Cl)cnc3N)cc2)c1] | N-(4-((2-amino-5-chloropyridin-3-yl)oxy)phenyl)-3-methoxybenzamide | 370 |
| 303 | 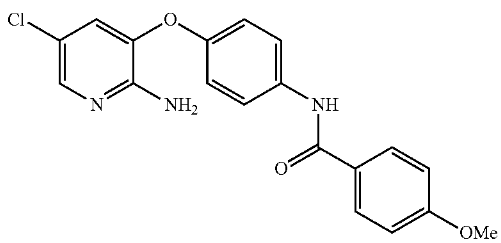 [SMILES: COc1ccc(C(=O)Nc2ccc(Oc3cc(Cl)cnc3N)cc2)cc1] | N-(4-((2-amino-5-chloropyridin-3-yl)oxy)phenyl)-4-methoxybenzamide | 370 |
| 304 | 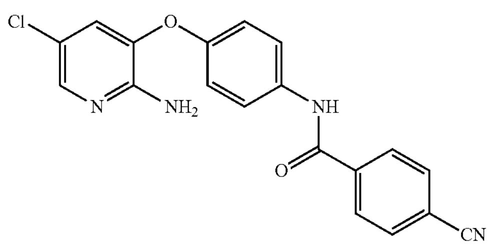 [SMILES: N#Cc1ccc(C(=O)Nc2ccc(Oc3cc(Cl)cnc3N)cc2)cc1] | N-(4-((2-amino-5-chloropyridin-3-yl)oxy)phenyl)-4-cyanobenzamide | 365 |
| 305 | 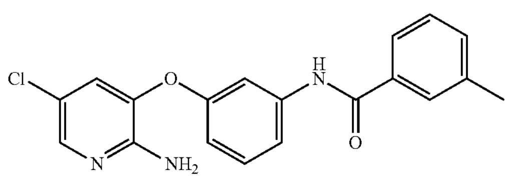 [SMILES: Cc1cccc(C(=O)Nc2cccc(Oc3cc(Cl)cnc3N)c2)c1] | N-(3-((2-amino-5-chloropyridin-3-yl)oxy)phenyl)-3-methylbenzamide | 354 |
| 306 | 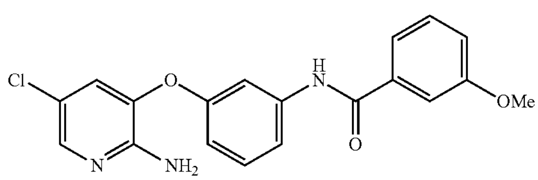 [SMILES: COc1cccc(C(=O)Nc2cccc(Oc3cc(Cl)cnc3N)c2)c1] | N-(3-((2-amino-5-chloropyridin-3-yl)oxy)phenyl)-3-methoxybenzamide | 370 |
| 307 | 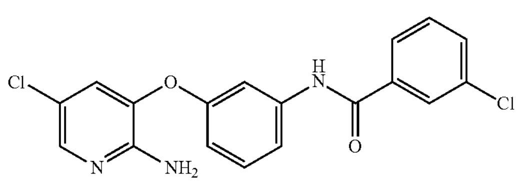 [SMILES: Nc1ncc(Cl)cc1Oc1cccc(NC(=O)c2cccc(Cl)c2)c1] | N-(3-((2-amino-5-chloropyridin-3-yl)oxy)phenyl)-3-chlorobenzamide | 374 |
| 308 | 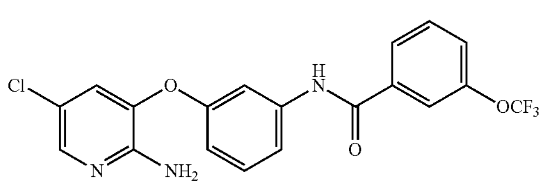 [SMILES: Nc1ncc(Cl)cc1Oc1cccc(NC(=O)c2cccc(OC(F)(F)F)c2)c1] | N-(3-((2-amino-5-chloropyridin-3-yl)oxy)phenyl)-3-(trifluoromethoxy)benzamide | 424 |

TABLE 10-continued

| Comps. No. | Compound structure | Compound name | MS [M + 1] |
|---|---|---|---|
| 309 | 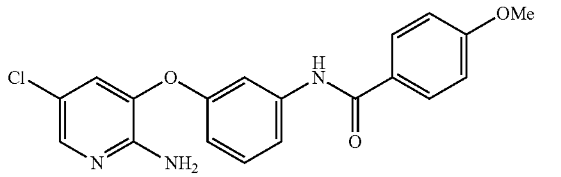 [SMILES: COc1ccc(C(=O)Nc2cccc(Oc3cc(Cl)cnc3N)c2)cc1] | N-(3-((2-amino-5-chloropyridin-3-yl)oxy)phenyl)-4-methoxy-benzamide | 370 |
| 310 | 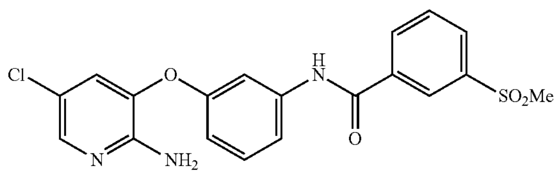 [SMILES: CS(=O)(=O)c1cccc(C(=O)Nc2cccc(Oc3cc(Cl)cnc3N)c2)c1] | N-(3-((2-amino-5-chloropyridin-3-yl)oxy)phenyl)-3-(methyl-sulfonyl)benzamide | 418 |
| 311 | 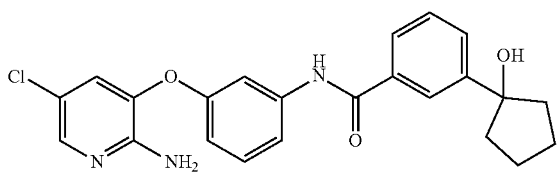 [SMILES: Nc1ncc(Cl)cc1Oc1cccc(NC(=O)c2cccc(C3(O)CCCC3)c2)c1] | N-(3-((2-amino-5-chloropyridin-3-yl)oxy)phenyl)-3-(1-hydroxy-cyclopentyl)benzamide | 424 |
| 312 | 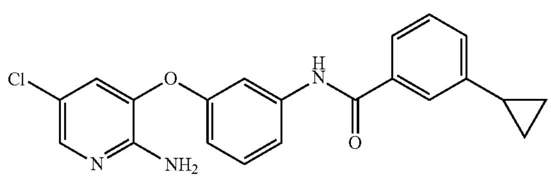 [SMILES: Nc1ncc(Cl)cc1Oc1cccc(NC(=O)c2cccc(C3CC3)c2)c1] | N-(3-((2-amino-5-chloropyridin-3-yl)oxy)phenyl)-3-cyclopropyl-benzamide | 380 |
| 313 | 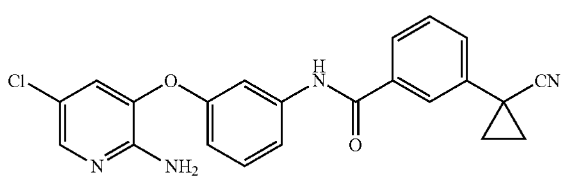 [SMILES: N#CC1(c2cccc(C(=O)Nc3cccc(Oc4cc(Cl)cnc4N)c3)c2)CC1] | N-(3-((2-amino-5-chloropyridin-3-yl)oxy)phenyl)-3-(1-cyano-cyclopropyl)benzamide | 405 |
| 314 | 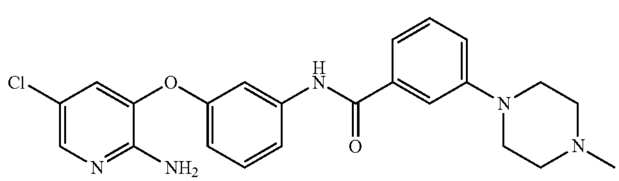 [SMILES: CN1CCN(c2cccc(C(=O)Nc3cccc(Oc4cc(Cl)cnc4N)c3)c2)CC1] | N-(3-((2-amino-5-chloropyridin-3-yl)oxy)phenyl)-3-(4-methyl-piperazin-1-yl)benzamide | 438 |

Example 38

Synthesis of N-(5-((2-amino-5-chloropyridin-3-yl)oxy)-2-fluorophenyl)-3-methoxybenzamide Example 39

Synthesis of N-(5-((2-amino-5-chloropyridin-3-yl)oxy)-2-chlorophenyl)-3-methoxybenzamide

315

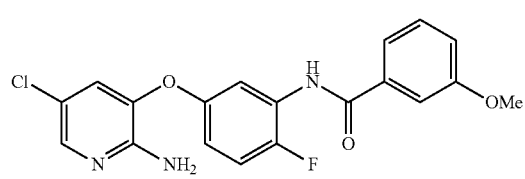

316

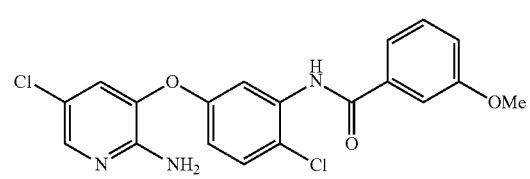

Similar procedure to example 5 was followed to arrive at compound 315, with the LC-MS[M+H]-m/z 388.

Similar procedure to example 5 was followed to arrive at compound 316, with the LC-MS[M+H]-m/z 404.

Example 40

Synthesis of N-(5-((2-amino-5-chloropyridin-3-yl)oxy)-2-methylphenyl)-3-methoxybenzamide

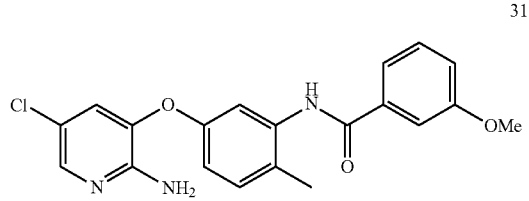

317

Similar procedure to example 5 was followed to arrive at compound 317, with the LC-MS[M+H]-m/z 384.

Example 41

Synthesis of N-(5-(1-((2-amino-5-chloropyridin-3-yl)oxy)ethyl)-2-fluorophenyl)-3-methoxybenzamide

318

Similar procedure to example 5 was followed to arrive at compound 318, with the LC-MS[M+H]-m/z 416.

Example 42

Synthesis of N-(3-(((2-amino-5-chloropyridin-3-yl)oxy)methyl)-2-fluorophenyl)-3-methoxybenzamide

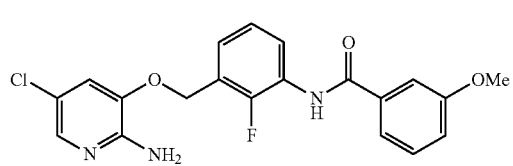

319

Similar procedure to example 5 was followed to arrive at compound 319, with the LC-MS[M+H]-m/z 402.

Example 43

Synthesis of N-(3-(((2-amino-5-chloropyridin-3-yl)oxy)methyl)-4-fluorophenyl)-3-methoxybenzamide

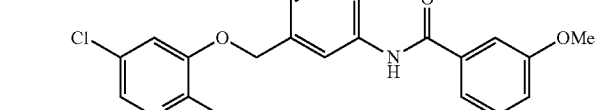

320

Similar procedure to example 5 was followed to arrive at compound 320, with the LC-MS[M+H]-m/z 402.

Example 44

Synthesis of (R)—N-(3-(1-((5-chloropyridin-3-yl)oxy)ethyl)phenyl)-3-methylbenzamide

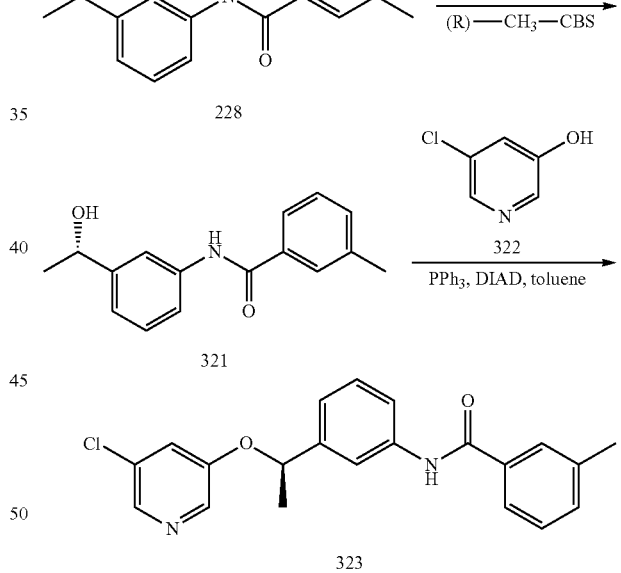

Step 1: Similar procedure to example 4 was followed to compound 321.

Step 2: To the solution of 231 (1.03 g, 4.0 mmol) and 322 (620 mg, 4.8 mmol) in anhydrous toluene (50 mL) was added DIAD (1.70 g, 8.0 mmol) dropwise at 0° C. and the inner temperature was kept below 5° C. After the addition is completed, the reaction mixture was warmed to 25° C. and stirred for overnight. When the reaction was completed, silica gel (10 g) was added to the reaction mixture. The resulting mixture was purified by column chromatography to give the desired product as yellow solid. LC-MS[M+H]-m/z 367. Yield: 68.2%.

Example 45

Synthesis of (R)—N-(3-(1-((6-chloropyrazin-2-yl)oxy)ethyl)phenyl)-3-(trifluoromethyl)benzamide

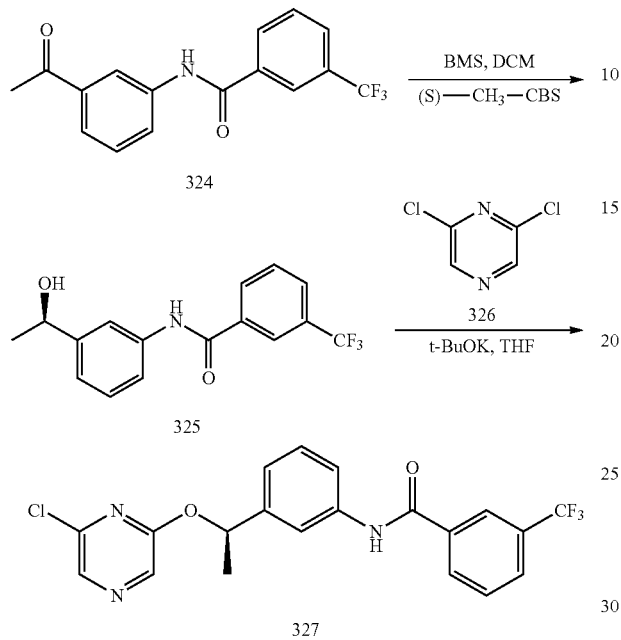

Step 1: Similar procedure to example 4 was followed to compound 325.

Step 2: To the solution of t-BuOK (448 mg, 4 mmol) and 325 (1.23 g. 4.0 mmol) in anhydrous THF (2 mL) that had be stirred at room temperature for 5 min, was added 326 (592 mg, 4.0 mmol). The mixture was stirred at 50° C. for overnight. When the reaction was completed, silica gel (10 g) was added to the reaction mixture. The resulting mixture was purified by column chromatography to give the desired product as yellow oil. LC-MS [M+H]-m/z 422. Yield: 59.3%.

Example 46

Synthesis of (R)-1-(3-(1-((2-amino-5-chloropyridin-3-yl)oxy)ethyl)phenyl)-3-(p-tolyl)urea

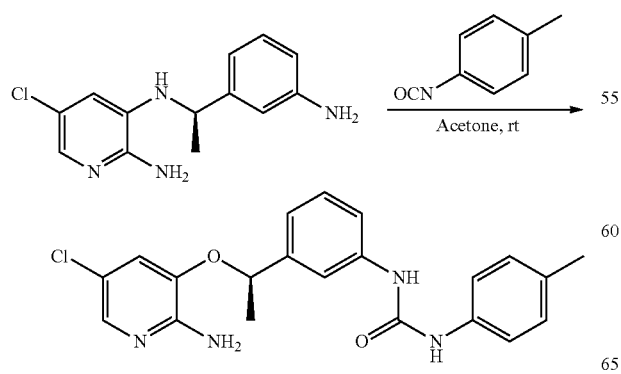

To a stirred solution of 165 (132 mg, 0.5 mmol) in acetone (2 mL) was added p-Tolyl isocyanate (80 mg, 0.6 mmol). The mixture was stirred at room temperature for 18 h. When the reaction was completed, the insolubles was filtered off, and the filtrate was concentrated under reduced pressure. The residue was purified by column chromatography to give the desired product as white solid. LC-MS[M+H]-m/z 397.

Example 47

Synthesis of (R)-1-(3-(1-((2-amino-5-chloropyridin-3-yl)oxy)ethyl)phenyl)-3-(m-tolyl)urea

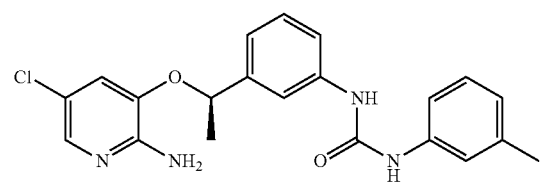

Similar procedure to example 46 was followed to arrive at compound 329, with the LC-MS[M+H]-m/z 397.

Example 48

The reaction route of compounds 330-347 was as follows:

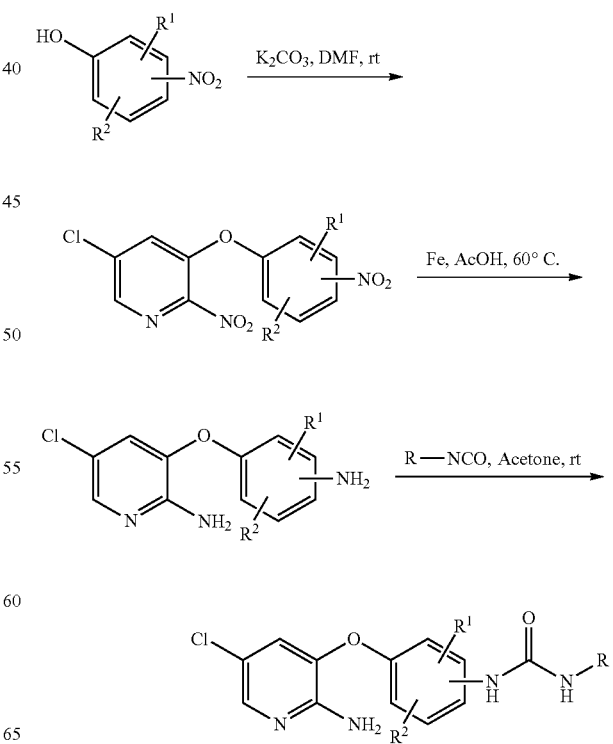

TABLE 11

| Comps. No. | Compound structure | Compound name | MS [M + 1] |
|---|---|---|---|
| 330 | 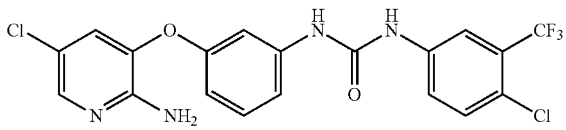 [SMILES: Nc1ncc(Cl)cc1Oc1cccc(NC(=O)Nc2ccc(Cl)c(C(F)(F)F)c2)c1] | 1-(3-((2-amino-5-chloropyridin-3-yl)oxy)phenyl)-3-(4-chloro-3-(trifluoromethyl)phenyl)urea | 457 |
| 331 | 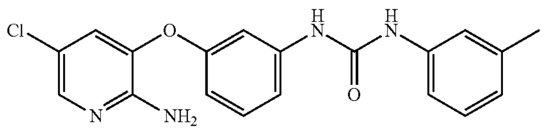 [SMILES: Cc1cccc(NC(=O)Nc2cccc(Oc3cc(Cl)cnc3N)c2)c1] | 1-(3-((2-amino-5-chloropyridin-3-yl)oxy)phenyl)-3-(m-tolyl)urea | 369 |
| 332 | 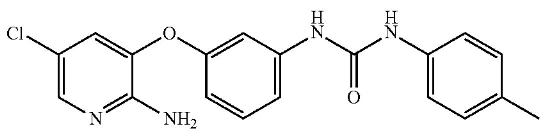 [SMILES: Cc1ccc(NC(=O)Nc2cccc(Oc3cc(Cl)cnc3N)c2)cc1] | 1-(3-((2-amino-5-chloropyridin-3-yl)oxy)phenyl)-3-(p-tolyl)urea | 369 |
| 333 | 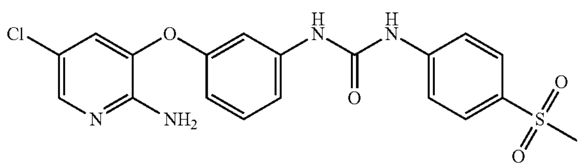 [SMILES: CS(=O)(=O)c1ccc(NC(=O)Nc2cccc(Oc3cc(Cl)cnc3N)c2)cc1] | 1-(3-((2-amino-5-chloropyridin-3-yl)oxy)phenyl)-3-(4-(methylsulfonyl)phenyl)urea | 433 |
| 334 | 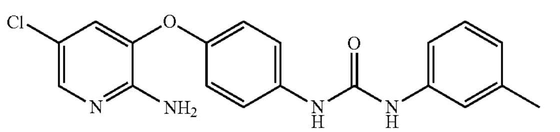 [SMILES: Cc1cccc(NC(=O)Nc2ccc(Oc3cc(Cl)cnc3N)cc2)c1] | 1-(4-((2-amino-5-chloropyridin-3-yl)oxy)phenyl)-3-(m-tolyl)urea | 369 |
| 335 | 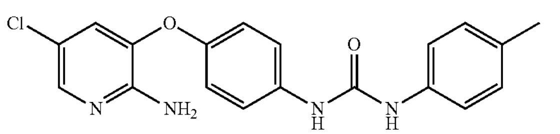 [SMILES: Cc1ccc(NC(=O)Nc2ccc(Oc3cc(Cl)cnc3N)cc2)cc1] | 1-(4-((2-amino-5-chloropyridin-3-yl)oxy)phenyl)-3-(p-tolyl)urea | 369 |
| 336 | 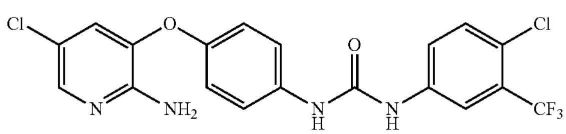 [SMILES: Nc1ncc(Cl)cc1Oc1ccc(NC(=O)Nc2ccc(Cl)c(C(F)(F)F)c2)cc1] | 1-(4-((2-amino-5-chloropyridin-3-yl)oxy)phenyl)-3-(4-chloro-3-(trifluoromethyl)phenyl)urea | 457 |
| 337 | 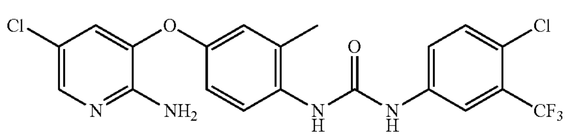 [SMILES: Cc1cc(Oc2cc(Cl)cnc2N)ccc1NC(=O)Nc1ccc(Cl)c(C(F)(F)F)c1] | 1-(4-((2-amino-5-chloropyridin-3-yl)oxy)-2-methylphenyl)-3-(4-chloro-3-(trifluoromethyl)phenyl)urea | 471 |
| 338 | 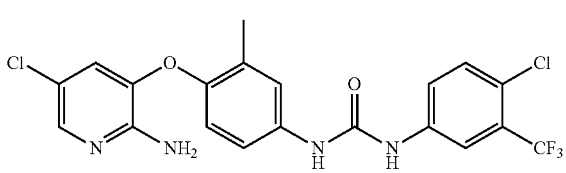 [SMILES: Cc1cc(NC(=O)Nc2ccc(Cl)c(C(F)(F)F)c2)ccc1Oc1cc(Cl)cnc1N] | 1-(4-((2-amino-5-chloropyridin-3-yl)oxy)-3-methylphenyl)-3-(4-chloro-3-(trifluoromethyl)phenyl)urea | 471 |
| 339 | 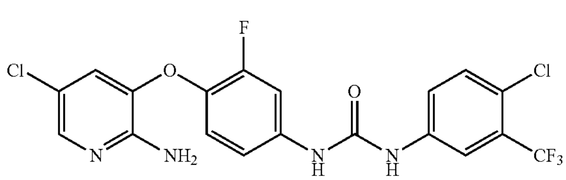 [SMILES: Nc1ncc(Cl)cc1Oc1ccc(NC(=O)Nc2ccc(Cl)c(C(F)(F)F)c2)cc1F] | 1-(4-((2-amino-5-chloropyridin-3-yl)oxy)-3-fluorophenyl)-3-(4-chloro-3-(trifluoromethyl)phenyl)urea | 475 |

TABLE 11-continued

| Comps. No. | Compound structure | Compound name | MS [M + 1] |
|---|---|---|---|
| 340 | 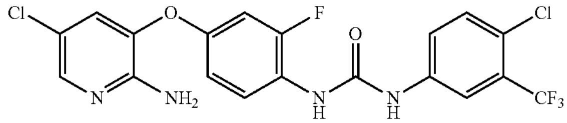 [SMILES: Nc1ncc(Cl)cc1Oc1ccc(NC(=O)Nc2ccc(Cl)c(C(F)(F)F)c2)c(F)c1] | 1-(4-((2-amino-5-chloropyridin-3-yl)oxy)-2-fluorophenyl)-3-(4-chloro-3-(trifluoromethyl)phenyl)urea | 475 |
| 341 | 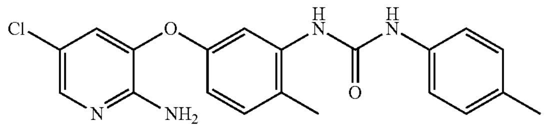 [SMILES: Cc1ccc(NC(=O)Nc2cc(Oc3cc(Cl)cnc3N)ccc2C)cc1] | 1-(5-((2-amino-5-chloropyridin-3-yl)oxy)-2-methylphenyl)-3-(p-tolyl)urea | 383 |
| 342 | 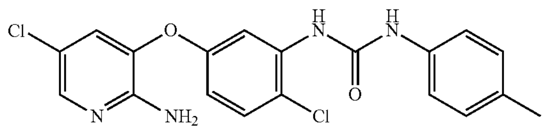 [SMILES: Cc1ccc(NC(=O)Nc2cc(Oc3cc(Cl)cnc3N)ccc2Cl)cc1] | 1-(5-((2-amino-5-chloropyridin-3-yl)oxy)-2-chlorophenyl)-3-(p-tolyl)urea | 403 |
| 343 | 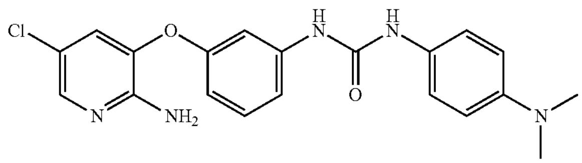 [SMILES: CN(C)c1ccc(NC(=O)Nc2cccc(Oc3cc(Cl)cnc3N)c2)cc1] | 1-(3-((2-amino-5-chloropyridin-3-yl)oxy)phenyl)-3-(4-(dimethylamino)phenyl)urea | 398 |
| 344 | 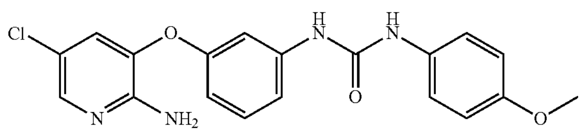 [SMILES: COc1ccc(NC(=O)Nc2cccc(Oc3cc(Cl)cnc3N)c2)cc1] | 1-(3-((2-amino-5-chloropyridin-3-yl)oxy)phenyl)-3-(4-methoxyphenyl)urea | 385 |
| 345 | 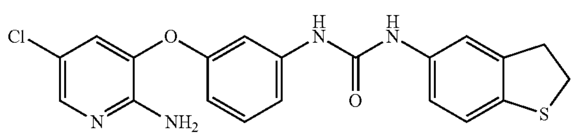 [SMILES: Nc1ncc(Cl)cc1Oc1cccc(NC(=O)Nc2ccc3c(c2)CCS3)c1] | 1-(3-((2-amino-5-chloropyridin-3-yl)oxy)phenyl)-3-(2,3-dihydrobenzo[b]thiophen-5-yl)urea | 413 |
| 346 | 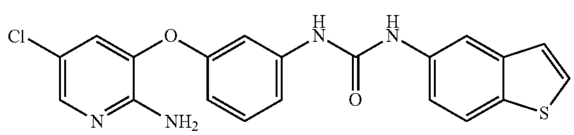 [SMILES: Nc1ncc(Cl)cc1Oc1cccc(NC(=O)Nc2ccc3sccc3c2)c1] | 1-(3-((2-amino-5-chloropyridin-3-yl)oxy)phenyl)-3-(benzo[b]thiophen-5-yl)urea | 411 |
| 347 | 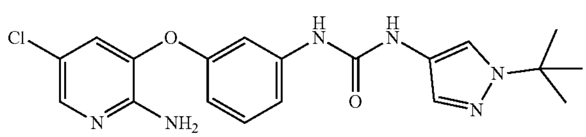 [SMILES: CC(C)(C)n1cc(NC(=O)Nc2cccc(Oc3cc(Cl)cnc3N)c2)cn1] | 1-(3-((2-amino-5-chloropyridin-3-yl)oxy)phenyl)-3-(1-(tert-butyl)-1H-pyrazol-4-yl)urea | 401 |

Example 49

Synthesis of Compounds 348-356 was Similar Procedures to that of Example 7

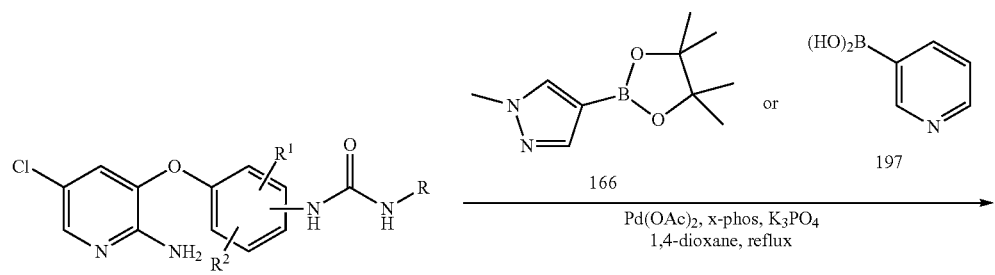

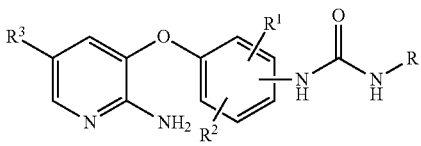

TABLE 12

| Comps. No. | Compound structure | Compound name | MS [M + 1] |
|---|---|---|---|
| 348 | 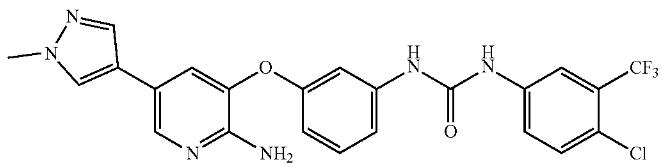 [SMILES: Cn1cc(-c2cnc(N)c(Oc3cccc(NC(=O)Nc4ccc(Cl)c(C(F)(F)F)c4)c3)c2)cn1] | 1-(3-((2-amino-5-(1-methyl-1H-pyrazol-4-yl)pyridin-3-yl)oxy)phenyl)-3-(4-chloro-3-(trifluoromethyl)phenyl)urea | 502 |
| 349 | 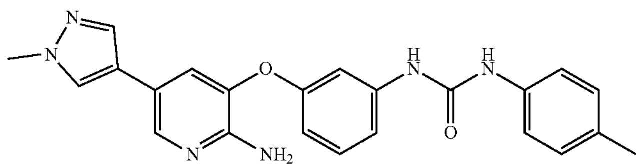 | 1-(3-((2-amino-5-(1-methyl-1H-pyrazol-4-yl)pyridin-3-yl)oxy)phenyl)-3-(p-tolyl)urea | 415 |
| 350 | 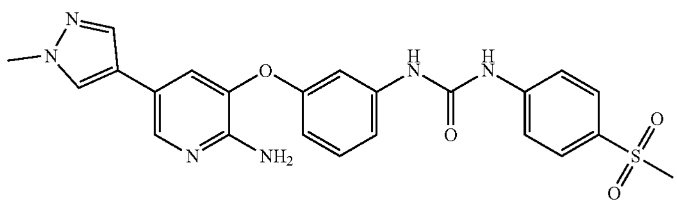 | 1-(3-((2-amino-5-(1-methyl-1H-pyrazol-4-yl)pyridin-3-yl)oxy)phenyl)-3-(4-(methylsulfonyl)phenyl)urea | 479 |
| 351 | 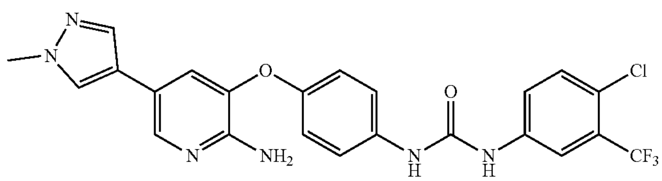 [SMILES: Cn1cc(-c2cnc(N)c(Oc3ccc(NC(=O)Nc4ccc(Cl)c(C(F)(F)F)c4)cc3)c2)cn1] | 1-(4-((2-amino-5-(1-methyl-1H-pyrazol-4-yl)pyridin-3-yl)oxy)phenyl)-3-(4-chloro-3-(trifluoromethyl)phenyl)urea | 503 |
| 352 | 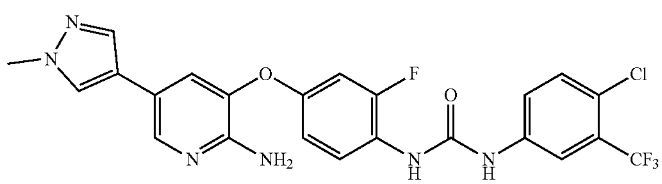 [SMILES: Cn1cc(-c2cnc(N)c(Oc3ccc(NC(=O)Nc4ccc(Cl)c(C(F)(F)F)c4)c(F)c3)c2)cn1] | 1-(4-((2-amino-5-(1-methyl-1H-pyrazol-4-yl)pyridin-3-yl)oxy)-2-fluorophenyl)-3-(4-chloro-3-(trifluoromethyl)phenyl)urea | 521 |
| 353 | 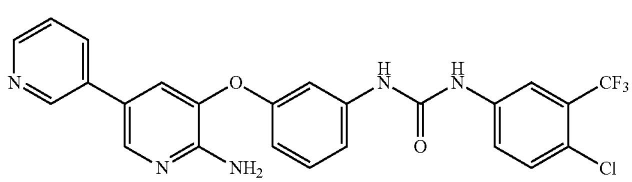 [SMILES: Nc1ncc(-c2cccnc2)cc1Oc1cccc(NC(=O)Nc2ccc(Cl)c(C(F)(F)F)c2)c1] | 1-(3-((6-amino-[3,3'-bipyridin]-5-yl)oxy)phenyl)-3-(4-chloro-3-(trifluoromethyl)phenyl)urea | 500 |
| 354 | 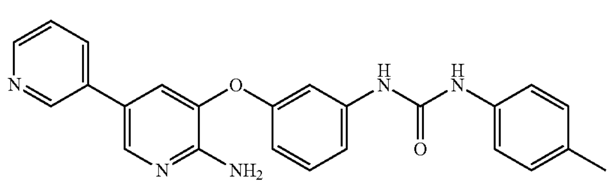 [SMILES: Cc1ccc(NC(=O)Nc2cccc(Oc3cc(-c4cccnc4)cnc3N)c2)cc1] | 1-(3-((6-amino-[3,3'-bipyridin]-5-yl)oxy)phenyl)-3-(p-tolyl)urea | 412 |

TABLE 12-continued

| Comps. No. | Compound structure | Compound name | MS [M + 1] |
|---|---|---|---|
| 355 | 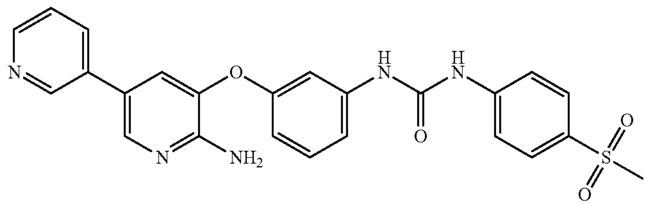 [SMILES: CS(=O)(=O)c1ccc(NC(=O)Nc2cccc(Oc3cc(-c4cccnc4)cnc3N)c2)cc1] | 1-(3-((6-amino-[3,3'-bipyridin]-5-yl)oxy)phenyl)-3-(4-(methylsulfonyl)phenyl)urea | 476 |
| 356 | 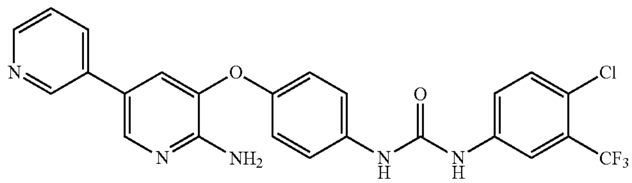 [SMILES: Nc1ncc(-c2cccnc2)cc1Oc1ccc(NC(=O)Nc2ccc(Cl)c(C(F)(F)F)c2)cc1] | 1-(4-((6-amino-[3,3'-bipyridin]-5-yl)oxy)phenyl)-3-(4-chloro-3-(trifluoromethyl)phenyl)urea | 500 |

Example 50

Synthesis of Compounds 357-366 was Similar Procedures to that of Example 7

TABLE 13

| Comps. No. | Compound structure | Compound name | MS [M + 1] |
|---|---|---|---|
| 357 | 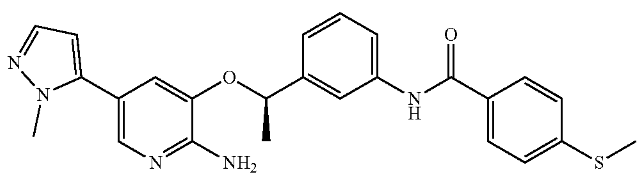 [SMILES: CSc1ccc(C(=O)Nc2cccc([C@@H](C)Oc3cc(-c4ccnn4C)cnc3N)c2)cc1] | (R)-N-(3-(1-((2-amino-5-(1-methyl-1H-pyrazol-5-yl)pyridin-3-yl)oxy)ethyl)phenyl)-4-(methylthio)benzamide | 460 |
| 358 | 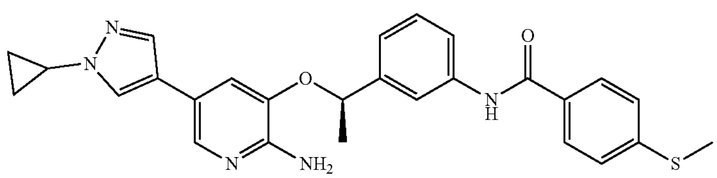 [SMILES: CSc1ccc(C(=O)Nc2cccc([C@@H](C)Oc3cc(-c4cnn(C5CC5)c4)cnc3N)c2)cc1] | (R)-N-(3-(1-((2-amino-5-(1-cyclopropyl-1H-pyrazol-4-yl)pyridin-3-yl)oxy)ethyl)phenyl)-4-(methylthio)benzamide | 486 |
| 359 | 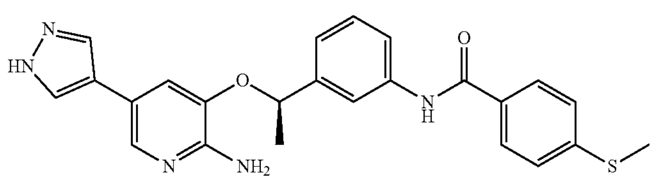 [SMILES: CSc1ccc(C(=O)Nc2cccc([C@@H](C)Oc3cc(-c4cn[nH]c4)cnc3N)c2)cc1] | (R)-N-(3-(1-((2-amino-5-(1H-pyrazol-4-yl)pyridin-3-yl)oxy)ethyl)phenyl)-4-(methylthio)benzamide | 446 |
| 360 | 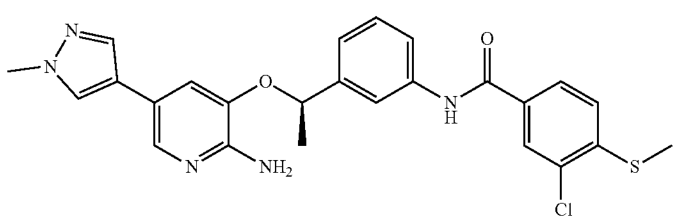 | (R)-N-(3-(1-((2-amino-5-(1-methyl-1H-pyrazol-4-yl)pyridin-3-yl)oxy)ethyl)phenyl)-3-chloro-4-(methylthio)benzamide | 494 |

TABLE 13-continued

| Comps. No. | Compound structure | Compound name | MS [M + 1] |
|---|---|---|---|
| 361 | 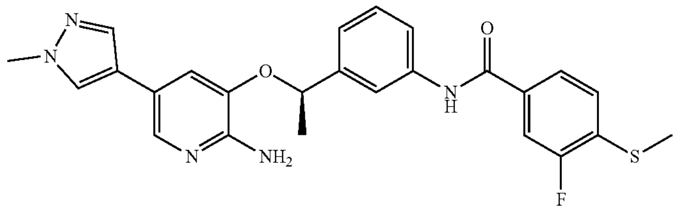 | (R)-N-(3-(1-((2-amino-5-(1-methyl-1H-pyrazol-4-yl)pyridin-3-yl)oxy)ethyl)phenyl)-3-fluoro-4-(methylthio)benzamide | 478 |
| 362 | 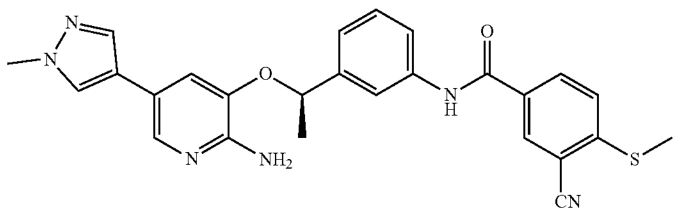 | (R)-N-(3-(1-((2-amino-5-(1-methyl-1H-pyrazol-4-yl)pyridin-3-yl)oxy)ethyl)phenyl)-3-cyano-4-(methylthio)benzamide | 485 |
| 363 | 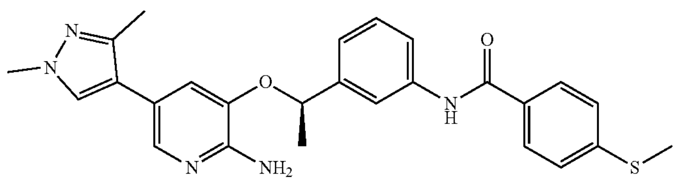 | 3-dimethyl-1H-pyrazol-4-yl)pyridin-3-yl)oxy)ethyl)phenyl)-4-(methylthio)benzamide | 474 |
| 364 | 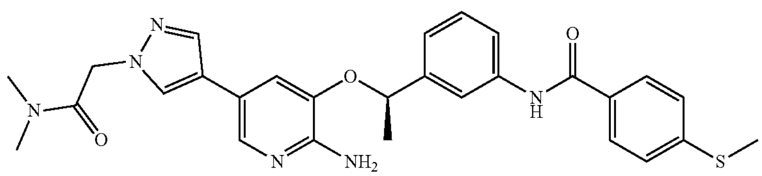 | (2-(dimethylamino)-2-oxo-ethyl)-1H-pyrazol-4-yl)pyridin-3-yl)oxy)ethyl)phenyl)-4-(methylthio)benzamide | 531 |
| 365 | 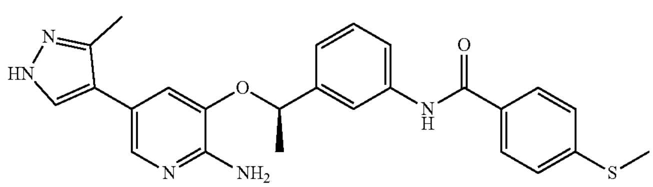 [SMILES: CSc1ccc(C(=O)Nc2cccc([C@@H](C)Oc3cc(-c4c[nH]nc4C)cnc3N)c2)cc1] | (R)-N-(3-(1-((2-amino-5-(3-methyl-1H-pyrazol-4-yl)pyridin-3-yl)oxy)ethyl)phenyl)-4-(methylthio)benzamide | 460 |
| 366 | 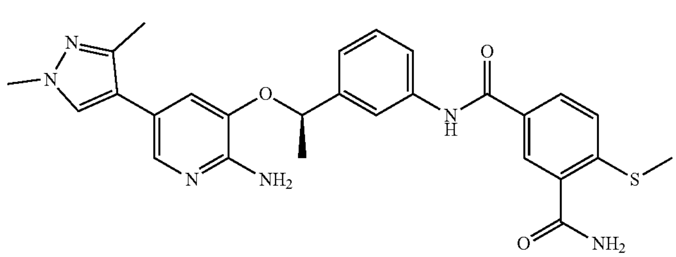 | (R)-N1-(3-(1-((2-amino-5-(1-methyl-1H-pyrazol-4-yl)pyridin-3-yl)oxy)ethyl)phenyl)-4-(methylthio)isophthalamide | 503 |

Example 51

Synthesis of N-(3-((R)-1-((2-amino-5-(1-methyl-1H-pyrazol-4-yl)pyridin-3-yl)oxy)ethyl)phenyl)-3-(methylsulfinyl)benzamide

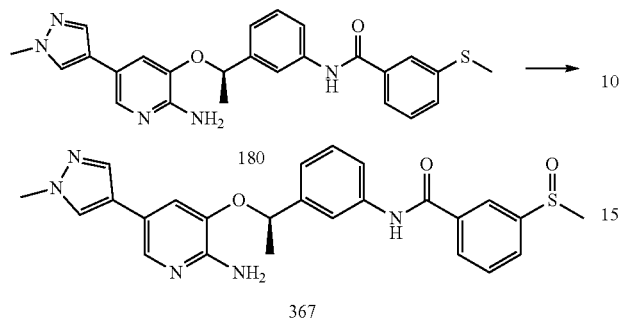

Compound 180 (100 mg, 0.22 mmol) was added to a 25 mL round bottom flask, then ethanol (10 mL) and hydrogen peroxide (30%, 2 mL) were added. The resulting mixture was stirred for overnight at room temperature. Brine was added and the mixture was extracted with DCM. The combined organic layers were dried, and concentrated in vacuo. The residue was purified by column chromatography (DCM:MeOH=40:1) to give the desired product as white solid. LC-MS[M+H]-m/z: 476.

Example 52

Synthesis of Compounds 368-373 was Similar Procedures to that of Example 7

TABLE 14

| Comps. No. | Compound structure | Compound name | MS [M + 1] |
|---|---|---|---|
| 368 | 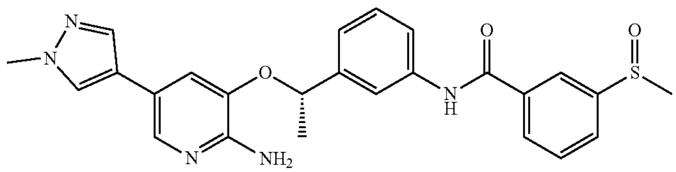 | N-(3-((S)-1-((2-amino-5-(1-methyl-1H-pyrazol-4-yl)pyridin-3-yl)oxy)ethyl)phenyl)-3-(methylsulfinyl)benzamide | 476 |
| 369 | 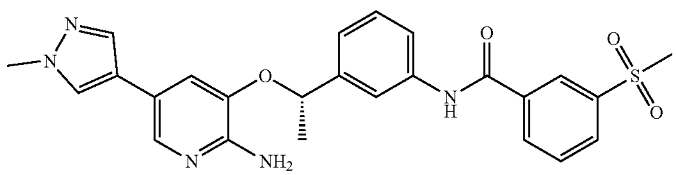 | (S)-N-(3-(1-((2-amino-5-(1-methyl-1H-pyrazol-4-yl)pyridin-3-yl)oxy)ethyl)phenyl)-3-(methylsulfonyl)benzamide | 492 |
| 370 | 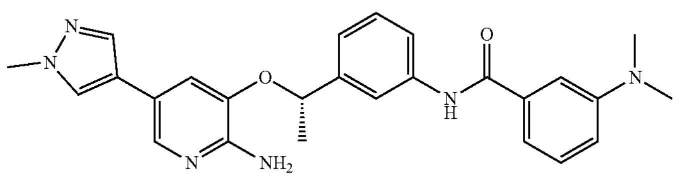 | (S)-N-(3-(1-((2-amino-5-(1-methyl-1H-pyrazol-4-yl)pyridin-3-yl)oxy)ethyl)phenyl)-3-(dimethylamino)benzamide | 457 |
| 371 | 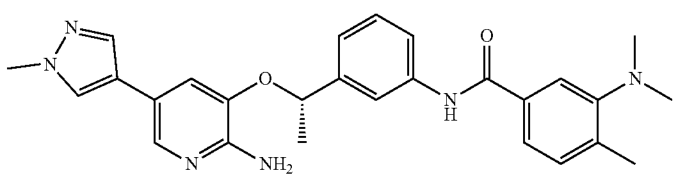 | (S)-N-(3-(1-((2-amino-5-(1-methyl-1H-pyrazol-4-yl)pyridin-3-yl)oxy)ethyl)phenyl)-3-(dimethylamino)-4-methyl-benzamide | 471 |
| 372 | 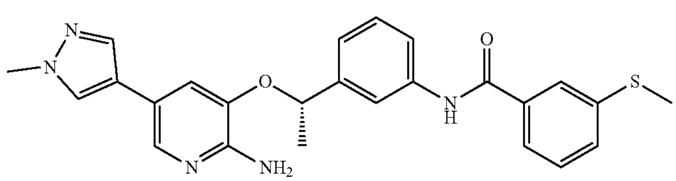 | (S)-N-(3-(1-((2-amino-5-(1-methyl-1H-pyrazol-4-yl)pyridin-3-yl)oxy)ethyl)phenyl)-3-(methylthio)benzamide | 460 |

TABLE 14-continued

| Comps. No. | Compound structure | Compound name | MS [M + 1] |
|---|---|---|---|
| 373 | 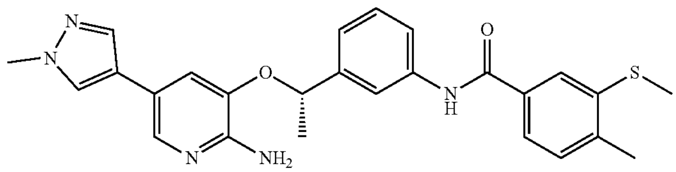 | (S)-N-(3-(1-((2-amino-5-(1-methyl-1H-pyrazol-4-yl)pyridin-3-yl)oxy)ethyl)phenyl)-4-methyl-3-(methylthio)benzamide | 474 |

Example 53: CSF-1R Kinase Assay

I. Materials and Instruments

2104 EnVision® Multilabel Reader (PerkinElmer)
OptiPlate-384, White Opaque 384-well MicroPlate (Cat.6007290, PerkinElmer)
HTRF kinEASE TK (Cat.62TKOPEC, Cisbio)
CSF-1R(Cat. PV3249, Invitrogen)
ATP 10 mM (Cat. PV3227, Invitrogen)
DTT 1 M (Cat. D5545, Sigma)
$MgCl_2$ 1 M (Cat. M8266, Sigma)
$MnCl_2$ 1 M (Cat.244589. Sigma)

II. Experimental Procedure

1. Reagent Preparing

TABLE 15

Kinase reaction system and concentration

| | TK | CSF-1R |
|---|---|---|
| Enzyme Concentration | Final concentration in enzyme reaction step (10 µL) | 0.012 ng/ul |
| ATP (µM) | | 2.5 uM |
| Substrate-TK | | 460 nM |
| Enzyme reaction time | | 40 min |
| Sa-XL665 | Final concentration in the end system (20 µL) | 28.75 nM |
| TK-Ab-Cryptate | | 1:100 dilution |

TABLE 16

1mL1 × Kinase Buffer component (µL):

| Kinase | 5 × Enzyme buffer | $MgCl_2$ | $MnCl_2$ | DTT | SEB | $ddH_2O$ |
|---|---|---|---|---|---|---|
| CSF-IR | 200 | 5 | 1 | 1 | 0 | 793 |

5×Substrate-TK and ATP Solution
The reaction concentration of Substrate-TK and ATP are shown in table 15.
Substrate-TK and ATP were diluted to 5 times of the reaction concentration by 1×Kinase Buffer.
5×Enzyme Solution
The reaction concentration of CSF1R enzyme is shown in table 15.
CSF1R enzyme was diluted to 5×enzyme solution by 1×kinase buffer.
4×Sa-XL665 Solution
The reaction concentration of Sa-XL665 is shown in table 15.
Sa-XL665 was diluted to 4×Sa-XL665 solution by Detection Buffer.

100×TK-Ab-Cryptate Solution
TK-Ab-Cryptate was diluted to 100×TK-Ab-Cryptate solution by Detection Buffer.

2. Experimental Procedure

After all reagents had been prepared according to the above method, except enzymes, the sample was added after equilibrium to room temperature.

a. Firstly, 2.5% DMSO solution was prepared by using 1×kinase buffer (the high concentration of DMSO will affect the reaction and control the final concentration of DMSO to 1%). Then the compounds were diluted by 2.5% DMSO solution corresponding to the enzyme. The screening concentration of the compounds was 4 times gradient dilution from 1000 nM, and 8 concentrations. In addition to the control pore, 4 microlitres of diluted solution containing 2.5% DMSO were added to the reaction pore and 4 microlitres of previously prepared solution containing 2.5% DMSO were added to the control pore.

b. 2 microlitres of previously prepared TK-biotin substrate solution was added to all reaction pore (the amount of substrate used for enzyme screening is shown in Table 15).

c. Adding 2 microlitres of CSF1R enzyme solution of corresponding concentration (the amount of enzyme is shown in Table 15) to all reaction pore except negative pore. The negative pore is supplemented with 2 microlitres of enzyme corresponding to 1 ×kinase buffer. After mixing, the compound and enzyme can be fully combined by incubating at room temperature for 10 minutes.

d. Enzyme reaction was initiated by adding 2 microlitres ATP solution of corresponding concentration to all reaction pore. The reaction time was 30 minutes (the corresponding ATP concentration and reaction time at enzyme screening were shown in Table 15).

e. Preparing the test solution 5 minutes before the end of kinase reaction. Streptavidin-XL665 and TK antibody europium cryptate (1:100) were prepared with detection buffer in the kit (the corresponding concentration of detection reagent for enzyme screening is shown in Table 15).

f. After the kinase reaction, 5 microlitres of diluted Streptavidin-XL665 were added to all reaction pore, mixing, and then the diluted TK antibody europium cryptate solution was added immediately.

g. After 1 hour reaction at room temperature, the fluorescence signals (320 nm stimulation, 665 nm, 615 nm emission) were detected by ENVISION (Perkinelmer) instrument. The inhibition rate of each pore was calculated by full active pore and background signal pore, and the average value of complex pore was obtained. Meanwhile, the half inhibitory activity ($IC_{50}$) of each compound was fitted by professional drawing analysis software PRISM 5.0.

The Flow Chart of the Experiment is as Follows:

TABLE 17

| Enzyme step (10 μL) | kinase assay Sample | Control Negative | Positive |
|---|---|---|---|
| Compounds | 4 μL | 4 μL 2.5% DMSO/ kinase buffer | 4 μL 2.5% DMSO/ kinase buffer |
| TK Substrate-biotin | 2 uL | 2 μL | 2 μL |
| Kinase | 2 μL | 2 μL Kinase buffer | 2 μL |
| Seal plate and incubate 10 min at RT | | | |
| ATP | 2 μL | 2 μL | 2 μL |
| Seal plate and incubate 40 min at RT | | | |
| Detection step(10 uL) | | | |
| Sa-XL665 | 5 uL | 5 μL | 5 μL |
| TK Ab-Cryptate | 5 μL | 5 μL | 5 μL |
| Seal plate and incubate 1 h at RT | | | |
| 320 nm Excitation, 665 nm, 615 nm Emission | | | |

3. Data Analysis

Emission Ratio (ER)=665 nm Emission signal/615 nm Emission signal

Inhibitory rate=(ERpositive−ERsample)/(ERpositive−ERnegative)*100%

Using Graphpad Prism 5 and log (inhibitor) vs. normalized response to fit $IC_{50}$ curve and calculate $IC_{50}$ value.

The $IC_{50}$ data of the compounds prepared in Representative Examples 3-52 are as follows (Table 18):

TABLE 18

| Comps. | In vitro inhibitory activity of CSF-1R $IC_{50}$ |
|---|---|
| 22 | +++ |
| 54 | +++ |
| 55 | +++ |
| 64 | +++ |
| 72 | +++ |
| 73 | +++ |
| 74 | +++ |
| 78 | +++ |
| 83 | +++ |
| 85 | +++ |
| 86 | +++ |
| 95 | ++ |
| 103 | + |
| 132 | +++ |
| 134 | +++ |
| 141 | ++ |
| 170 | +++ |
| 171 | +++ |
| 174 | +++ |
| 175 | +++ |
| 178 | +++ |
| 179 | +++ |
| 180 | +++ |
| 181 | +++ |
| 182 | +++ |
| 187 | +++ |
| 188 | +++ |
| 202 | +++ |
| 205 | +++ |
| 206 | +++ |
| 222 | ++ |
| 236 | ++ |
| 305 | ++ |
| 318 | ++ |
| 323 | ++ |
| 327 | ++ |

TABLE 18-continued

| Comps. | In vitro inhibitory activity of CSF-1R $IC_{50}$ |
|---|---|
| 331 | ++ |
| 348 | +++ |
| 367 | +++ |

Footnote:
+++: ≤50 nM;
++: 51-500 nM;
+: ≥500 nM, but <10 um

Example 54: NFS-60 Cell Assay

1. Experimental Materials
1.1 Cell Line
Mouse Myelogenous Leukemia Cells (NFS-60)
1.2 Compounds
Using DMSO to dissolve, and the required concentration was prepared with full culture medium without factors.
1.3 Main Reagents
Medium: RPMI Medium 1640, Gibco, No. 31800-022
Fetal Bovine Serum: PANSera. ES, No. 2602-P130707
Penicillin-streptomycin: TRANS
Trypsin: Gibco, No. 25300-062
PBS: Hyclone, No. SH30258.01
Mouse M-CSF/CSF-1 Protein: Sino Biological Inc, No. 51112-MNAH
M-CSF: Qilu Pharmaceutical co., Ltd.

2. Experimental Method
The logarithmic growth phase of NFS-60 cells (1640+10% FBS+40 ng/ml M-CSF+1% Penicillin-streptomycin) were centrifuged (1000 r/min) and cultured in a factor-free medium at 37° C., 5% $CO_2$ for 24 hours. Centrifugating (1000 r/min), the culture medium was replaced by new culture medium including 40 ng/mL factors, and inoculated on 96-well plate by $2*10^4$ cells/mL, 100 μL/hole. After 16 hours, the tested compounds were added 10 μL/hole, 3 duplicate holes per compound, 37° C., 5% $CO_2$, continue to cultured for 72 h. Then 10 μL CCK reagent was added to each hole. After incubation for 4 hours, the absorbance of each hole was measured at 450 nm wavelength.

According to Formula:

Inhibitory rate (%)=(1-OD value of test pore/OD value of solvent control pore)×100%

3. Experimental Results
The experimental results of the inhibition of NFS-60 cell proliferation by the compounds prepared in Example 3-52, 0.5 uM, are shown in the following table:

TABLE 19

| Comps. | inhibition ratio % |
|---|---|
| 54 | ++ |
| 70 | +++ |
| 72 | +++ |
| 74 | +++ |
| 126 | +++ |
| 132 | +++ |
| 134 | +++ |
| 137 | +++ |
| 150 | +++ |
| 168 | +++ |
| 169 | +++ |
| 178 | +++ |
| 179 | +++ |
| 180 | +++ |

TABLE 19-continued

| Comps. | inhibition ratio % |
|---|---|
| 181 | +++ |
| 182 | +++ |
| 199 | +++ |
| 200 | +++ |
| 205 | +++ |
| 206 | +++ |
| 212 | +++ |
| 367 | +++ |

Footnote:
+++: ≥50%;
++: 10%-50%;
+: <10%

Example 55: Animal Pharmacodynamics Experiment

In this study. MC-38 cell lines were inoculated in $C_{57}$ mice
Experimental animal: C57 mice, male, 5-6 weeks old (18-22 g)
Cell Lines: MC38
Inoculation: $2 \times 10^6$/0.1 mL, Matrigel is added in 3:1 ratio
PD1: InVivoMAb anti-mouse PD-1 (CD279). BioXCell
Group: On day 4 after inoculating, all the mice were divided into 13 groups, respectively model group, the anti-PD1 2 mg/kg group, anti-PD1 10 mg/kg group, testing compounds alone, and the tested compound combine with anti-PD1 10 mg/kg. Compounds were intragastrically administered daily at a dose of 30 mg/kg and anti-PD1 was intraperitoneally injected once every 3 days. The drug was administered continuously for 2 weeks. In model group, 80% glycerol+ 20% CMC-Na was given daily.

Results: The experimental results of anti-PD1 combined with the compounds prepared in the representative example 3-52 on the inhibition of tumor size of MC-38 transplanted tumors are as follows:

TABLE 20

| Groups | inhibition ratio | Groups | inhibition ratio |
|---|---|---|---|
| anti-PD1-2 mg/kg | + | | |
| anti-PD1-10 mg/kg | ++ | | |
| 72-30 mg/kg | + | 72-30 mg/kg + anti-PD1-10 mg/kg | ++ |
| 78-30 mg/kg | + | 78-30 mg/kg + anti-PD1-10 mg/kg | ++ |
| 83-30 mg/kg | + | 83-30 mg/kg + anti-PD1-10 mg/kg | +++ |
| 85-30 mg/kg | + | 85-30 mg/kg + anti-PD1-10 mg/kg | +++ |
| 86-30 mg/kg | + | 86-30 mg/kg + anti-PD1-10 mg/kg | +++ |
| 178-30 mg/kg | ++ | 178-30 mg/kg + anti-PD1-10 mg/kg | +++ |
| 179-30 mg/kg | ++ | 179-30 mg/kg + anti-PD1-10 mg/kg | +++ |
| 182-30 mg/kg | ++ | 182-30 mg/kg + anti-PD1-10 mg/kg | +++ |

Footnote:
+++: ≥30%;
++: 10%-30%;
+: <10%

Although the present invention has been described in considerable detail with reference to certain preferred versions thereof, other versions are possible. Therefore, the spirit and scope of the present invention should not be limited to the description of the preferred versions described herein. All features disclosed in the specification, including the abstract and drawings, and all the steps in any method or process disclosed, may be combined in any combination, except combinations where at least some of such features and/or steps are mutually exclusive. Each feature disclosed in the specification, including abstract and drawings, can be replaced by alternative features serving the same, equivalent or similar purpose, unless expressly stated otherwise. Thus, unless expressly stated otherwise, each feature disclosed is one example only of a generic series of equivalent or similar features. Various modifications of the invention, in addition to those described herein, will be apparent to those skilled in the art from the foregoing description. Such modifications are also intended to fall within the scope of the appended claims. Each reference cited in the present application is herein incorporated by reference in its entirety.

The invention claimed is:

1. A compound of Formula (Ib):

Formula (Ib)

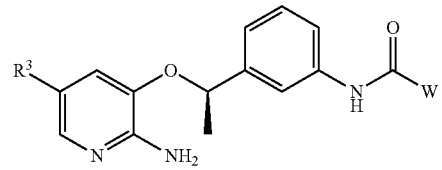

wherein $R^3$ is selected from H, halogen, $C_6$-$C_{10}$ phenyl, 5-10 membered heteroaryl, $C_3$-$C_6$ heterocycloalkyl; the hydrogens in $R^3$ are optionally substituted by one or more $R^7$ groups independently, and the adjacent $R^7$ groups can join to form a 5-7 membered ring;

W is selected from $C_6$-$C_{10}$ aryl, 5-10 membered heteroaryl, wherein the hydrogens on the rings may be substituted by one or more $R^7$ groups independently;

$R^7$ is selected from H, halogen, OH, $NO_2$, CN, $O(C_1$-$C_3)$ alkyl, $(C_1$-$C_5)$heteroalkyl, $O(C_3$-$C_6)$cycloalkyl, $O(C_3$-$C_6)$heterocycloalkyl, $C_1$-$C_5$ alkyl, C=C, C≡C, $C_3$-$C_6$ cycloalkyl, $C_3$-$C_6$ heterocycloalkyl, $NR^5R^6$, $C(O)(C_1$-$C_2)$alkyl, $C(O)O(C_1$-$C_2)$alkyl, $P(O)((C_1$-$C_2)$alkyl$)_2$, $SO_2$ cyclopropyl, $S(O)_n(C_1$-$C_3)$alkyl, wherein n=0, 1, or 2; and the two adjacent $R^7$ groups can join to form a 5-7 membered ring;

Each $R^5$ and $R^6$ is independently selected from H, $C_1$-$C_3$ alkyl, $C_3$-$C_6$ cycloalkyl, $C(O)C_1$-$C_3$ alkyl, $S(O)_2(C_1$-$C_3)$alkyl or $S(O)_2(C_3$-$C_6)$cycloalkyl; $R^5$ and $R^6$ can join to form a 3-6 membered ring.

2. The compound of claim 1, wherein $R^3$ is selected from H, halogen; W is selected from phenyl or 5-10 membered heteroaryl; wherein the hydrogens on the ring may be substituted by one or more $R^7$ groups independently, and the two adjacent R⁷ groups can join to form a 5-7 membered ring; $R^7$ is selected from halogen, OH, NO$_2$, CN, O(C$_1$-C$_3$) alkyl, (C$_1$-C$_5$) heteroalkyl, O(C$_3$-C$_6$)cycloalkyl, O(C$_3$-C$_6$) heterocycloalkyl, C$_1$-C$_5$ alkyl, C=C, C≡C, C$_3$-C$_6$ cycloalkyl, C$_3$-C$_6$ heterocycloalkyl, N((C$_1$-C$_2$)alkyl)$_2$, NH(C$_1$-C$_2$) alkyl, C(O)(C$_1$-C$_2$)alkyl, C(O)O(C$_1$-C$_2$)alkyl, P(O)((C$_1$-C$_2$) alkyl)$_2$, SO$_2$ cyclopropyl, S(O)$_n$(C$_1$-C$_3$)alkyl, wherein n=0, 1, or 2.

3. The compound of claim 1, wherein $R^3$ is selected from phenyl, 5-10 membered heteroaryl, C$_3$-C$_6$ heterocycloalkyl, wherein the hydrogens on the ring may be independently substituted by halogen, OH, NO$_2$, CN, O(C$_1$-C$_3$)alkyl, (C$_1$-C$_5$)heteroalkyl, O(C$_3$-C$_6$)cycloalkyl, O(C$_3$-C$_6$)heterocycloalkyl, C$_1$-C$_5$ alkyl, C=C, C≡C, C$_3$-C$_6$ cycloalkyl, C$_3$-C$_6$ heterocycloalkyl, N((C$_1$-C$_2$)alkyl)$_2$, NH(C$_1$-C$_2$)alkyl, C(O)(C$_1$-C$_2$)alkyl, C(O)O(C$_1$-C$_2$)alkyl, P(O)((C$_1$-C$_2$)alkyl)$_2$, SO$_2$ cyclopropyl, S(O)$_n$(C$_1$-C$_3$)alkyl, wherein n=0, 1, or 2; W is selected from phenyl or 5-10 membered heteroaryl, wherein the hydrogens on the ring may be substituted by one or more R⁷ groups independently, and one of the substituted groups should be selected from NH$_2$, N((C$_1$-C$_2$)alkyl)$_2$, NH(C$_1$-C$_2$)alkyl, C(O)(C$_1$-C$_2$)alkyl, C(O)O(C$_1$-C$_2$)alkyl, P(O)((C$_1$-C$_2$)alkyl)$_2$, SO$_2$ cyclopropyl, S(O)$_n$(C$_1$-C$_3$)alkyl, wherein n=0, 1, or 2, and the adjacent groups in R⁷ or W can join to form a 5-7 membered ring.

4. The compound of claim 3, wherein $R^3$ is selected from phenyl, pyrazolyl, pyridyl, wherein the hydrogens on the ring may be substituted by halogen, CN, O(C$_1$-C$_3$)alkyl, C$_1$-C$_3$ alkyl, C$_3$-C$_6$ cycloalkyl, (C$_1$-C$_5$)heteroalkyl, C$_3$-C$_6$ heterocycloalkyl, N((C$_1$-C$_2$)alkyl)$_2$, NH(C$_1$-C$_2$)alkyl; and the adjacent substituted groups in R³ can join to form a 5-7 membered ring.

5. The compound of claim 4, wherein $R^3$ is selected from pyrazolyl, pyridyl, wherein the hydrogens on the ring may be substituted by halogen, CN, C$_1$-C$_3$ alkyl, C$_3$-C$_6$ cycloalkyl, (C$_1$-C$_5$) heteroalkyl, C$_3$-C$_6$ heterocycloalkyl, and the adjacent substituted groups on R³ can join to form a 5-7 membered ring.

6. The compound of claim 3, wherein W is selected from phenyl, wherein the hydrogens on the ring is substituted by one or more R⁷ groups independently, and one of the substituted groups should be selected from N((C$_1$-C$_2$) alkyl)$_2$, C(O)(C$_1$-C$_2$) alkyl, C(O)O(C$_1$-C$_2$) alkyl, P(O)((C$_1$-C$_2$)alkyl)$_2$, SO$_2$ cyclopropyl, S(O)$_n$(C$_1$-C$_3$) alkyl, wherein n=0, 1, or 2, and the adjacent substituted groups in W can join to form a 5-7 membered ring.

7. The compound of claim 1, wherein the compound is selected from:
- (R)—N-(3-(1-((2-amino-5-chloropyridin-3-yl)oxy)ethyl) phenyl)-3-methylbenzamide
- (R)—N-(3-(1-((2-amino-5-chloropyridin-3-yl)oxy)ethyl) phenyl)-2-chloro-5-methylbenzamide
- (R)—N-(3-(1-((2-amino-5-chloropyridin-3-yl)oxy)ethyl) phenyl)-3-methoxybenzamide
- (R)—N-(3-(1-((2-amino-5-chloropyridin-3-yl)oxy)ethyl) phenyl)-3-cyanobenzamide
- (R)—N-(3-(1-((2-amino-5-chloropyridin-3-yl)oxy)ethyl) phenyl)-2,5-dichlorobenzamide
- (R)—N-(3-(1-((2-amino-5-chloropyridin-3-yl)oxy)ethyl) phenyl)-3-ethynylbenzamide
- (R)—N-(3-(1-((2-amino-5-chloropyridin-3-yl)oxy)ethyl) phenyl)-3-(methylsulfonyl)benzamide
- (R)—N-(3-(1-((2-amino-5-chloropyridin-3-yl)oxy)ethyl) phenyl)-3-(isopropylsulfonyl)benzamide
- (R)—N-(3-(1-((2-amino-5-chloropyridin-3-yl)oxy)ethyl) phenyl)-3-(cyclopropylsulfonyl)benzamide
- (R)—N-(3-(1-((2-amino-5-chloropyridin-3-yl)oxy)ethyl) phenyl)-3-(dimethylphosphoryl)benzamide
- (R)—N-(3-(1-((2-amino-5-chloropyridin-3-yl)oxy)ethyl) phenyl)-3-(dimethylamino)benzamide
- (R)—N-(3-(1-((2-amino-5-chloropyridin-3-yl)oxy)ethyl) phenyl)-5-methylnicotinamide
- (R)—N-(3-(1-((2-amino-5-chloropyridin-3-yl)oxy)ethyl) phenyl)-2-fluoro-5-methylbenzamide
- (R)—N-(3-(1-((2-amino-5-chloropyridin-3-yl)oxy)ethyl) phenyl)-2-chloro-3-methylbenzamide
- (R)—N-(3-(1-((2-amino-5-chloropyridin-3-yl)oxy)ethyl) phenyl)-3-cyclopropylbenzamide
- (R)—N-(3-(1-((2-amino-5-chloropyridin-3-yl)oxy)ethyl) phenyl)-3-isopropylbenzamide
- (R)—N-(3-(1-((2-amino-5-chloropyridin-3-yl)oxy)ethyl) phenyl)-3-isopropoxybenzamide
- (R)—N-(3-(1-((2-amino-5-chloropyridin-3-yl)oxy)ethyl) phenyl)-3-(ethylsulfonyl)benzamide
- (R)—N-(3-(1-((2-amino-5-chloropyridin-3-yl)oxy)ethyl) phenyl)-2-chloro-3-methoxybenzamide
- (R)—N-(3-(1-((2-amino-5-chloropyridin-3-yl)oxy)ethyl) phenyl)-3-(1-hydroxycyclopentyl)benzamide
- (R)—N-(3-(1-((2-amino-5-chloropyridin-3-yl)oxy)ethyl) phenyl)-4-(methylsulfonyl)benzamide
- (R)—N-(3-(1-((2-amino-5-chloropyridin-3-yl)oxy)ethyl) phenyl)-3-(1-hydroxycyclobutyl)benzamide
- (R)—N-(3-(1-((2-amino-5-chloropyridin-3-yl)oxy)ethyl) phenyl)-4-methylbenzamide
- (R)—N-(3-(1-((2-amino-5-chloropyridin-3-yl)oxy) ethyl)-4-chlorophenyl)-2-chloro-3-methylbenzamide
- N-(3-((R)-1-((2-amino-5-chloropyridin-3-yl)oxy)ethyl) phenyl)-3-((2-hydroxycyclohexyl)amino)benzamide
- (R)—N-(5-(1-((2-amino-5-chloropyridin-3-yl)oxy) ethyl)-2-fluorophenyl)-2-chloro-3-methylbenzamide
- (R)—N-(3-(1-((2-amino-5-chloropyridin-3-yl)oxy)ethyl) phenyl)-3-(1-hydroxycyclohexyl)benzamide
- (R)—N-(3-(1-((2-amino-5-chloropyridin-3-yl)oxy)ethyl) phenyl)-4-((4-methylpiperazin-1-yl)methyl)benzamide
- (R)—N-(3-(1-((2-amino-5-chloropyridin-3-yl)oxy)ethyl) phenyl)-3-(4-methylpiperazin-1-yl)benzamide
- (R)—N-(3-(1-((2-amino-5-chloropyridin-3-yl)oxy)ethyl) phenyl)-4-(4-methylpiperazin-1-yl)benzamide
- (R)—N-(3-(1-((2-amino-5-chloropyridin-3-yl)oxy)ethyl) phenyl)-2-methoxy-5-(methylsulfonyl)benzamide
- (R)—N-(3-(1-((2-amino-5-chloropyridin-3-yl)oxy)ethyl) phenyl)-3-((4-methylpiperazin-1-yl)methyl)benzamide
- (R)—N-(3-(1-((2-amino-5-chloropyridin-3-yl)oxy)ethyl) phenyl)-3-(cyclopropylsulfonyl)benzamide
- (R)—N-(3-(1-((2-amino-5-chloropyridin-3-yl)oxy)ethyl) phenyl)-3-(isopropylsulfonyl)benzamide
- (R)—N-(3-(1-((2-amino-5-chloropyridin-3-yl)oxy)ethyl) phenyl)-3-(cyclopentylsulfonyl)benzamide
- (R)—N-(3-(1-((2-amino-5-chloropyridin-3-yl)oxy)ethyl) phenyl)quinoline-3-carboxamide
- (R)—N-(3-(1-((2-amino-5-chloropyridin-3-yl)oxy)ethyl) phenyl)isoquinoline-6-carboxamide
- (R)—N-(3-(1-((2-amino-5-chloropyridin-3-yl)oxy)ethyl) phenyl)quinoline-6-carboxamide
- (R)—N-(3-(1-((2-amino-5-chloropyridin-3-yl)oxy)ethyl) phenyl)-3-(pyrrolidin-1-ylsulfonyl)benzamide
- (R)—N-(3-(1-((2-amino-5-chloropyridin-3-yl)oxy)ethyl) phenyl)-5-cyclopropylnicotinamide
- (R)—N-(5-(1-((2-amino-5-chloropyridin-3-yl)oxy)ethyl) pyridin-3-yl)-2-chloro-3-methylbenzamide
- (R)—N-(3-(1-((2-amino-5-chloropyridin-3-yl)oxy)ethyl) phenyl)-3-(1-cyanocyclopropyl)benzamide (R)—N-(3-(1-((2-amino-5-chloropyridin-3-yl)oxy)ethyl)phenyl)-3-cyclobutylbenzamide
(R)—N-(3-(1-((2-amino-5-chloropyridin-3-yl)oxy)ethyl)phenyl)-3-(trifluoromethyl)benzamide
(R)—N-(3-(1-((2-amino-5-chloropyridin-3-yl)oxy)ethyl)phenyl)-3-(pyrrolidin-1-yl)benzamide
(R)—N-(3-(1-((2-amino-5-chloropyridin-3-yl)oxy)ethyl)phenyl)-2,3-dihydrobenzo[b]thiophene-4-carboxamide 1,1-dioxide
(R)—N-(3-(1-((2-amino-5-chloropyridin-3-yl)oxy)ethyl)phenyl)-2,3-dihydrobenzo[b]thiophene-5-carboxamide 1,1-dioxide
(R)—N-(3-(1-((2-amino-5-chloropyridin-3-yl)oxy)ethyl)phenyl)benzo[d][1,3]dioxole-5-carboxamide
(R)—N-(3-(1-((2-amino-5-chloropyridin-3-yl)oxy)ethyl)phenyl)-5-fluoropicolinamide
(R)—N-(3-(1-((2-amino-5-chloropyridin-3-yl)oxy)ethyl)phenyl)-5-methylpicolinamide
(R)—N-(3-(1-((2-amino-5-chloropyridin-3-yl)oxy)ethyl)phenyl)-4-methylpicolinamide
(R)—N-(3-(1-((2-amino-5-chloropyridin-3-yl)oxy)ethyl)phenyl)-4-(trifluoromethyl)picolinamide
(R)—N-(3-(1-((2-amino-5-chloropyridin-3-yl)oxy)ethyl)phenyl)-5-(trifluoromethyl)picolinamide
(R)—N-(3-(1-((2-amino-5-chloropyridin-3-yl)oxy)ethyl)phenyl)-6-(trifluoromethyl)picolinamide
(R)—N-(3-(1-((2-amino-5-chloropyridin-3-yl)oxy)ethyl)phenyl)-4-methyl-3-(methylsulfonyl)benzamide
(R)—N-(5-(1-((2-amino-5-chloropyridin-3-yl)oxy)ethyl)-2-methylphenyl)-3-(trifluoromethyl)benzamide
(R)—N-(3-(1-((2-amino-5-chloropyridin-3-yl)oxy)ethyl)phenyl)-3-(difluoromethyl)benzamide
(R)—N-(3-(1-((2-amino-5-chloropyridin-3-yl)oxy)ethyl)phenyl)-6-methylpicolinamide
(R)—N-(3-(1-((2-amino-5-chloropyridin-3-yl)oxy)ethyl)phenyl)-4-chloro-3-methylbenzamide
(R)—N-(3-(1-((2-amino-5-chloropyridin-3-yl)oxy)ethyl)phenyl)-4-fluoro-3-methylbenzamide
(R)—N-(3-(1-((2-amino-5-chloropyridin-3-yl)oxy)ethyl)phenyl)-3,4-dimethylbenzamide
(R)—N-(3-(1-((2-amino-5-chloropyridin-3-yl)oxy)ethyl)phenyl)-2,3-dihydro-1H-indene-5-carboxamide
(R)—N-(3-(1-((2-amino-5-chloropyridin-3-yl)oxy)ethyl)phenyl)-2,3-dihydrobenzo[b]thiophene-6-carboxamide 1,1-dioxide
(R)—N-(3-(1-((2-amino-5-chloropyridin-3-yl)oxy)ethyl)phenyl)-3-fluoro-5-methylbenzamide
(R)—N-(3-(1-((2-amino-5-chloropyridin-3-yl)oxy)ethyl)phenyl)-3-chloro-5-methylbenzamide
(R)—N-(3-(1-((2-amino-5-chloropyridin-3-yl)oxy)ethyl)phenyl)-3,5-dimethylbenzamide
(R)—N-(5-(1-((2-amino-5-chloropyridin-3-yl)oxy)ethyl)-2-methylphenyl)-3-(methylsulfonyl)benzamide
(R)—N-(3-(1-((2-amino-5-chloropyridin-3-yl)oxy)ethyl)-4-fluorophenyl)-3-(methylsulfonyl)benzamide
(R)—N-(3-(1-((2-amino-5-chloropyridin-3-yl)oxy)ethyl)-4-chlorophenyl)-3-(methylsulfonyl)benzamide
(R)—N-(6-(1-((2-amino-5-chloropyridin-3-yl)oxy)ethyl)pyridin-2-yl)-3-methylbenzamide
(R)—N-(3-(1-((2-amino-5-chloropyridin-3-yl)oxy)ethyl)-4-methylphenyl)-3-(methylsulfonyl)benzamide
(R)—N-(3-(1-((2-amino-5-chloropyridin-3-yl)oxy)ethyl)-2-methylphenyl)-3-(methylsulfonyl)benzamide
(R)—N-(4-(1-((2-amino-5-chloropyridin-3-yl)oxy)ethyl)pyridin-2-yl)-3-methylbenzamide
(R)—N-(5-(1-((2-amino-5-chloropyridin-3-yl)oxy)ethyl)-2-chlorophenyl)-3-(methylsulfonyl)benzamide
(R)—N-(5-(1-((2-amino-5-chloropyridin-3-yl)oxy)ethyl)-2-fluorophenyl)-3-(methylsulfonyl)benzamide
(R)—N-(3-(1-((2-amino-5-chloropyridin-3-yl)oxy)ethyl)phenyl)-3-(methylsulfonyl)-4-(trifluoromethyl)benzamide
(R)—N-(3-(1-((2-amino-5-chloropyridin-3-yl)oxy)ethyl)phenyl)benzo[b]thiophene-5-carboxamide 1,1-dioxide
(R)—N-(3-(1-((2-amino-5-chloropyridin-3-yl)oxy)ethyl)phenyl)benzo[b]thiophene-6-carboxamide 1,1-dioxide
(R)—N-(3-(1-((2-amino-5-chloropyridin-3-yl)oxy)ethyl)phenyl)-3-(methylsulfonyl)-5-(trifluoromethyl)benzamide
(R)—N-(3-(1-((2-amino-5-chloropyridin-3-yl)oxy)ethyl)phenyl)-3,4-dimethyl-5-(methylsulfonyl)benzamide
(R)—N-(3-(1-((2-amino-5-chloropyridin-3-yl)oxy)ethyl)phenyl)-1,5-dimethyl-1H-pyrazole-3-carboxamide
(R)—N-(3-(1-((2-amino-5-chloropyridin-3-yl)oxy)ethyl)phenyl)-5-methylthiazole-2-carboxamide
(R)—N-(3-(1-((2-amino-5-chloropyridin-3-yl)oxy)ethyl)phenyl)-1-(tert-butyl)-1H-pyrazole-4-carboxamide
(R)—N-(3-(1-((2-amino-5-chloropyridin-3-yl)oxy)ethyl)phenyl)-1-isopropyl-1H-pyrazole-4-carboxamide
(R)—N-(3-(1-((2-amino-5-chloropyridin-3-yl)oxy)ethyl)phenyl)-1-methyl-1H-indazole-6-carboxamide
(R)—N-(3-(1-((2-amino-5-chloropyridin-3-yl)oxy)ethyl)phenyl)benzofuran-6-carboxamide
(R)—N-(3-(1-((2-amino-5-chloropyridin-3-yl)oxy)ethyl)phenyl)-1-methyl-1H-indole-6-carboxamide
(R)—N-(3-(1-((2-amino-5-chloropyridin-3-yl)oxy)ethyl)phenyl)-5-(tert-butyl)isoxazole-3-carboxamide
(R)—N-(3-(1-((2-amino-5-chloropyridin-3-yl)oxy)ethyl)phenyl)-1-methyl-2-oxo-1,2,3,4-tetrahydroquinoline-7-carboxamide
(R)—N-(3-(1-((2-amino-5-chloropyridin-3-yl)oxy)ethyl)phenyl)-1-methyl-1,2,3,4-tetrahydroquinoline-7-carboxamide
(R)—N-(3-(1-((2-amino-5-chloropyridin-3-yl)oxy)ethyl)phenyl)-1-methylindoline-6-carboxamide
(R)—N-(3-(1-((2-amino-5-chloropyridin-3-yl)oxy)ethyl)phenyl)-1-methyl-2-oxoindoline-6-carboxamide
(R)—N-(3-(1-((2-amino-5-chloropyridin-3-yl)oxy)ethyl)phenyl)-1,3-dihydroisobenzofuran-5-carboxamide
(R)—N-(3-(1-((2-amino-5-(1-methyl-1H-pyrazol-4-yl)pyridin-3-yl)oxy)ethyl)phenyl)-3-(methylsulfonyl)benzamide
(R)—N-(3-(1-((2-amino-5-(1-methyl-1H-pyrazol-4-yl)pyridin-3-yl)oxy)ethyl)phenyl)-3-(trifluoromethyl)benzamide
(R)—N-(3-(1-((2-amino-5-(1-methyl-1H-pyrazol-4-yl)pyridin-3-yl)oxy)ethyl)phenyl)-3,4-dimethylbenzamide
(R)—N-(3-(1-((2-amino-5-(1-methyl-1H-pyrazol-4-yl)pyridin-3-yl)oxy)ethyl)phenyl)-3,5-dimethylbenzamide
(R)—N-(3-(1-((2-amino-5-(1-methyl-1H-pyrazol-4-yl)pyridin-3-yl)oxy)ethyl)phenyl)-4-methyl-3-(methylsulfonyl)benzamide
(R)—N-(3-(1-((2-amino-5-(1-methyl-1H-pyrazol-4-yl)pyridin-3-yl)oxy)ethyl)phenyl)-2,3-dihydrobenzo[b]thiophene-6-carboxamide 1,1-dioxide
(R)—N-(3-(1-((2-amino-5-(1-methyl-1H-pyrazol-4-yl)pyridin-3-yl)oxy)ethyl)phenyl)-3-cyclopropylbenzamide
(R)—N-(3-(1-((2-amino-5-(1-methyl-1H-pyrazol-4-yl)pyridin-3-yl)oxy)ethyl)phenyl)-3-(methylsulfonyl)-4-(trifluoromethyl)benzamide (R)—N-(3-(1-((2-amino-5-(1-methyl-1H-pyrazol-4-yl)pyridin-3-yl)oxy)ethyl)phenyl)-3-(methylsulfonyl)-5-(trifluoromethyl)benzamide (R)—N-(3-(1-((2-amino-5-(1-methyl-1H-pyrazol-4-yl)pyridin-3-yl)oxy)ethyl)phenyl)-3,4-dimethyl-5-(methylsulfonyl)benzamide (R)—N-(3-(1-((2-amino-5-(1-methyl-1H-pyrazol-4-yl)pyridin-3-yl)oxy)ethyl)phenyl)-3-(dimethylamino)benzamide (R)—N-(3-(1-((2-amino-5-(1-methyl-1H-pyrazol-4-yl)pyridin-3-yl)oxy)ethyl)phenyl)-3-(dimethylamino)-4-methylbenzamide (R)—N-(3-(1-((2-amino-5-(1-methyl-1H-pyrazol-4-yl)pyridin-3-yl)oxy)ethyl)phenyl)-3-(methylthio)benzamide (R)—N-(3-(1-((2-amino-5-(1-methyl-1H-pyrazol-4-yl)pyridin-3-yl)oxy)ethyl)phenyl)-4-(methylthio)benzamide (R)—N-(3-(1-((2-amino-5-(1-methyl-1H-pyrazol-4-yl)pyridin-3-yl)oxy)ethyl)phenyl)-4-methyl-3-(methylthio)benzamide (R)—N-(3-(1-((2-amino-5-(1-methyl-1H-pyrazol-4-yl)pyridin-3-yl)oxy)ethyl)phenyl)-2',3'-dihydrospiro[cyclopropane-1,1'-indene]-6'-carboxamide (R)—N-(3-(1-((2-amino-5-(1-methyl-1H-pyrazol-4-yl)pyridin-3-yl)oxy)ethyl)phenyl)-1-methylindoline-6-carboxamide (R)—N-(3-(1-((2-amino-5-(1-methyl-1H-pyrazol-4-yl)pyridin-3-yl)oxy)ethyl)phenyl)-4-chloro-3-(dimethylamino)benzamide methyl (R)-3-((3-(1-((2-amino-5-(1-methyl-1H-pyrazol-4-yl)pyridin-3-yl)oxy)ethyl)phenyl)carbamoyl)benzoate (R)—N-(3-(1-((2-amino-5-(1-methyl-1H-pyrazol-4-yl)pyridin-3-yl)oxy)ethyl)phenyl)-3-isopropylbenzamide (R)—N-(3-(1-((2-amino-5-(1-methyl-1H-pyrazol-4-yl)pyridin-3-yl)oxy)ethyl)phenyl)-2,3-dihydro-1H-indene-5-carboxamide (R)—N-(3-(1-((2-amino-5-(1-methyl-1H-pyrazol-4-yl)pyridin-3-yl)oxy)ethyl)phenyl)-3-ethylbenzamide (R)—N-(3-(1-((2-amino-5-(1-methyl-1H-pyrazol-4-yl)pyridin-3-yl)oxy)ethyl)phenyl)-5-isopropylnicotinamide (R)—N-(3-(1-((2-amino-5-(1-methyl-1H-pyrazol-4-yl)pyridin-3-yl)oxy)ethyl)phenyl)-1-methyl-1H-indole-6-carboxamide (R)—N-(3-(1-((2-amino-5-(1-methyl-1H-pyrazol-4-yl)pyridin-3-yl)oxy)ethyl)phenyl)benzo[b]thiophene-6-carboxamide (R)—N-(3-(1-((2-amino-5-(1-methyl-1H-pyrazol-4-yl)pyridin-3-yl)oxy)ethyl)phenyl)-3,3-dimethyl-1,3-dihydroisobenzofuran-5-carboxamide (R)—N-(3-(1-((2-amino-5-(1-methyl-1H-pyrazol-4-yl)pyridin-3-yl)oxy)ethyl)phenyl)-2H-spiro[benzofuran-3,1'-cyclopropane]-5-carboxamide (R)—N-(3-(1-((2-amino-5-(1-methyl-1H-pyrazol-4-yl)pyridin-3-yl)oxy)ethyl)phenyl)-2,3-dihydrobenzofuran-5-carboxamide (R)—N-(3-(1-((6-amino-[3,3'-bipyridin]-5-yl)oxy)ethyl)phenyl)-3-(methylsulfonyl)benzamide (R)—N-(3-(1-((6-amino-[3,3'-bipyridin]-5-yl)oxy)ethyl)phenyl)-3-cyclopropylbenzamide (R)—N-(3-(1-((6-amino-[3,3'-bipyridin]-5-yl)oxy)ethyl)phenyl)-3-(trifluoromethyl)benzamide (R)—N-(3-(1-((6-amino-[3,3'-bipyridin]-5-yl)oxy)ethyl)phenyl)-3-methylbenzamide (R)—N-(3-(1-((6-amino-[3,3'-bipyridin]-5-yl)oxy)ethyl)phenyl)-3,4-dimethylbenzamide (R)—N-(3-(1-((6-amino-[3,3'-bipyridin]-5-yl)oxy)ethyl)phenyl)-3,5-dimethylbenzamide (R)—N-(3-(1-((6-amino-[3,3'-bipyridin]-5-yl)oxy)ethyl)phenyl)-3-(dimethylamino)benzamide (R)—N-(3-(1-((6-amino-[3,3'-bipyridin]-5-yl)oxy)ethyl)phenyl)-3-(dimethylamino)-4-methylbenzamide (R)—N-(3-(1-((6-amino-[3,3'-bipyridin]-5-yl)oxy)ethyl)phenyl)-3-(methylthio)benzamide (R)—N-(3-(1-((6-amino-[3,3'-bipyridin]-5-yl)oxy)ethyl)phenyl)-1-methylindoline-6-carboxamide (R)—N-(3-(1-((2-amino-5-(1-(piperidin-4-yl)-1H-pyrazol-4-yl)pyridin-3-yl)oxy)ethyl)phenyl)-3-cyclopropylbenzamide (R)—N-(3-(1-((2-amino-5-(1-cyclopropyl-1H-pyrazol-4-yl)pyridin-3-yl)oxy)ethyl)phenyl)-3-(dimethylamino)benzamide (R)—N-(3-(1-((2-amino-5-(1-ethyl-1H-pyrazol-4-yl)pyridin-3-yl)oxy)ethyl)phenyl)-3-(dimethylamino)benzamide (R)—N-(3-(1-((2-amino-5-(1-methylpiperidin-4-yl)pyridin-3-yl)oxy)ethyl)phenyl)-3-(dimethylamino)benzamide (R)—N-(3-(1-((2-amino-5-(4-hydroxy-3-methoxyphenyl)pyridin-3-yl)oxy)ethyl)phenyl)-3-(dimethylamino)benzamide (R)—N-(3-(1-((6-amino-6'-(4-methylpiperazin-1-yl)-[3,3'-bipyridin]-5-yl)oxy)ethyl)phenyl)-3-(dimethylamino)benzamide (R)—N-(3-(1-((6-amino-[3,4'-bipyridin]-5-yl)oxy)ethyl)phenyl)-3-(dimethylamino)benzamide (R)—N-(3-(1-((2-amino-5-(1-methyl-1H-pyrazol-5-yl)pyridin-3-yl)oxy)ethyl)phenyl)-4-(methylthio)benzamide (R)—N-(3-(1-((2-amino-5-(1-cyclopropyl-1H-pyrazol-4-yl)pyridin-3-yl)oxy)ethyl)phenyl)-4-(methylthio)benzamide (R)—N-(3-(1-((2-amino-5-(1H-pyrazol-4-yl)pyridin-3-yl)oxy)ethyl)phenyl)-4-(methylthio)benzamide (R)—N-(3-(1-((2-amino-5-(1-methyl-1H-pyrazol-4-yl)pyridin-3-yl)oxy)ethyl)phenyl)-3-chloro-4-(methylthio)benzamide (R)—N-(3-(1-((2-amino-5-(1-methyl-1H-pyrazol-4-yl)pyridin-3-yl)oxy)ethyl)phenyl)-3-fluoro-4-(methylthio)benzamide (R)—N-(3-(1-((2-amino-5-(1-methyl-1H-pyrazol-4-yl)pyridin-3-yl)oxy)ethyl)phenyl)-3-cyano-4-(methylthio)benzamide (R)—N-(3-(1-((2-amino-5-(1,3-dimethyl-1H-pyrazol-4-yl)pyridin-3-yl)oxy)ethyl)phenyl)-4-(methylthio)benzamide (R)—N-(3-(1-((2-amino-5-(1-(2-(dimethylamino)-2-oxoethyl)-1H-pyrazol-4-yl)pyridin-3-yl)oxy)ethyl)phenyl)-4-(methylthio)benzamide (R)—N-(3-(1-((2-amino-5-(3-methyl-1H-pyrazol-4-yl)pyridin-3-yl)oxy)ethyl)phenyl)-4-(methylthio)benzamide (R)—N1-(3-(1-((2-amino-5-(1-methyl-1H-pyrazol-4-yl)pyridin-3-yl)oxy)ethyl)phenyl)-4-(methylthio)isophthalamide N-(3-((R)-1-((2-amino-5-(1-methyl-1H-pyrazol-4-yl)pyridin-3-yl)oxy)ethyl)phenyl)-3-(methylsulfinyl)benzamide.

8. A pharmaceutical composition, comprising a therapeutically effective amount of at least one compound according to claim 1, and at least one pharmaceutically acceptable excipient, adjuvant or carrier.

9. A method of treating abnormal cell growth in a mammal subject, the method comprising administering to the subject a therapeutically effective amount of a compound of claim 1, wherein the abnormal cells growth is tumor.

10. A method of treating CSF-1R kinase-mediated melanoma, ovarian, uterine, breast, colon, stomach, liver, and non-small cell lung cancer in a subject, the method comprising administering to the subject a therapeutically effective amount of a compound of claim 1.

* * * * *